(12) United States Patent
Dopps et al.

(10) Patent No.: US 6,867,346 B1
(45) Date of Patent: Mar. 15, 2005

(54) ABSORBENT COMPOSITE HAVING FIBROUS BANDS

(75) Inventors: Melissa I. Dopps, Seattle, WA (US); Richard A. Edmark, Seattle, WA (US); David G. Marsh, Federal Way, WA (US); Peter A. Graef, Puyallup, WA (US)

(73) Assignee: Weyerhaeuser Company, Federal Way, WA (US)

( * ) Notice: Subject to any disclaimer, the term of this patent is extended or adjusted under 35 U.S.C. 154(b) by 0 days.

(21) Appl. No.: 09/666,213

(22) Filed: Sep. 21, 2000

Related U.S. Application Data

(60) Provisional application No. 60/155,464, filed on Sep. 21, 1999.

(51) Int. Cl.$^7$ .............................................. A61F 13/15
(52) U.S. Cl. ..................... 604/378; 604/374; 604/367; 604/375; 604/384; 442/411; 442/417; 442/366
(58) Field of Search ................................. 604/378, 374, 604/375, 367, 370, 385.01, 384; 428/114, 137, 163, 167, 171, 179, 191, 196, 297.4, 298.1, 398.4; 442/417, 366, 411, 413

(56) References Cited

U.S. PATENT DOCUMENTS

| | | | |
|---|---|---|---|
| 3,525,338 A | * | 8/1970 | Bernardin .................... 604/374 |
| 3,716,449 A | | 2/1973 | Gatward et al. |
| 3,868,287 A | | 2/1975 | Lewyckyj |
| 3,871,952 A | | 3/1975 | Robertson |
| 3,897,784 A | | 8/1975 | Fitzgerald |
| 3,938,782 A | | 2/1976 | Robertson |
| 4,100,324 A | * | 7/1978 | Anderson et al. ........... 442/344 |
| 4,354,901 A | | 10/1982 | Kopolow |
| 4,364,992 A | | 12/1982 | Ito et al. |
| 4,372,312 A | * | 2/1983 | Fendler et al. .............. 604/370 |
| 4,425,126 A | * | 1/1984 | Butterworth et al. ....... 604/366 |

(List continued on next page.)

FOREIGN PATENT DOCUMENTS

| | | | |
|---|---|---|---|
| EP | 0 339 461 B1 | 2/1989 | |
| EP | 0515750 A2 * | 2/1992 | .......... C08G/69/48 |
| EP | 0 528 248 | 2/1993 | |
| EP | 0 437 816 B1 | 7/1995 | |
| EP | 0 685 212 | 12/1995 | |
| EP | 0 719 531 A1 | 3/1996 | |
| EP | 0 724 870 A2 | 7/1996 | |
| EP | 0 528 248 B1 | 10/1996 | |
| EP | 748 894 A2 | 12/1996 | |
| EP | 0217666 A2 | 4/1997 | |
| FR | 2468689 | 8/1981 | |
| GB | 2 060 018 A | 4/1981 | |
| GB | 2 120 696 A | 7/1983 | |
| GB | 2 254 255 A | 7/1992 | |
| GB | 2284831 A | 6/1995 | |
| GB | 2 301 362 A | 4/1996 | |
| JP | 09 156012 | 6/1997 | |
| JP | 09156013 | 6/1997 | |
| WO | WO 93/06804 | 4/1993 | |
| WO | WO 95 13778 | 5/1995 | |
| WO | WO 97/05839 | 2/1997 | |
| WO | WO 97/18783 | 5/1997 | |
| WO | WO 97/21453 | 6/1997 | |
| WO | WO 98/24392 | 6/1998 | |
| WO | WO 98/37846 | 9/1998 | |
| WO | WO 98/47455 | 10/1998 | |
| WO | WO 99/32721 | 7/1999 | |
| WO | WO 00/41882 | 7/2000 | |
| WO | WO 00/47153 | 8/2000 | |

*Primary Examiner*—Jacqueline Stephens
(74) *Attorney, Agent, or Firm*—Christensen O'Connor Johnson Kindness PLLC

(57) ABSTRACT

An absorbent composite having fibrous bands is described. The composite includes one or more fibrous bands in a fibrous base. The base includes a fibrous matrix and absorbent material. The fibrous bands are substantially free of absorbent material. Absorbent articles that include the composite and methods for forming the composite are also disclosed.

41 Claims, 26 Drawing Sheets

U.S. PATENT DOCUMENTS

| | | |
|---|---|---|
| 4,443,297 A | 4/1984 | Cheshire et al. |
| 4,480,000 A * | 10/1984 | Watanabe et al. ............. 428/76 |
| 4,527,989 A * | 7/1985 | Karami .................. 604/385.25 |
| 4,546,027 A * | 10/1985 | Holvoet et al. ............. 428/109 |
| 4,551,142 A | 11/1985 | Kopolow |
| 4,559,050 A | 12/1985 | Iskra |
| 4,568,341 A | 2/1986 | Mitchell et al. |
| 4,605,401 A | 8/1986 | Chmelir et al. |
| 4,636,209 A * | 1/1987 | Lassen ....................... 604/378 |
| 4,676,784 A * | 6/1987 | Erdman et al. ............. 604/368 |
| 4,685,914 A | 8/1987 | Holtman |
| 4,704,116 A | 11/1987 | Enloe |
| 4,798,603 A | 1/1989 | Meyer et al. |
| 4,885,204 A | 12/1989 | Bither et al. |
| 4,988,344 A | 1/1991 | Reising et al. |
| 4,988,345 A | 1/1991 | Reising |
| 5,061,259 A | 10/1991 | Goldman et al. |
| 5,102,597 A | 4/1992 | Roe et al. |
| 5,134,007 A | 7/1992 | Reising et al. |
| 5,137,537 A | 8/1992 | Herron et al. |
| 5,147,343 A | 9/1992 | Kellenberger |
| 5,147,345 A | 9/1992 | Young et al. |
| 5,149,335 A | 9/1992 | Kellenberger et al. |
| 5,183,707 A * | 2/1993 | Herron et al. ............... 428/364 |
| 5,215,627 A | 6/1993 | Willis et al. |
| 5,217,445 A | 6/1993 | Young et al. |
| 5,277,915 A | 1/1994 | Provonchee et al. |
| 5,281,207 A | 1/1994 | Chmielewski et al. |
| 5,284,610 A | 2/1994 | Tai |
| 5,324,561 A | 6/1994 | Rezai et al. |
| 5,330,822 A | 7/1994 | Berg et al. |
| 5,350,370 A | 9/1994 | Jackson et al. |
| 5,354,290 A | 10/1994 | Gross |
| 5,360,420 A | 11/1994 | Cook et al. |
| 5,364,382 A | 11/1994 | Latimer et al. |
| 5,372,877 A | 12/1994 | Kannankeril |
| 5,415,643 A | 5/1995 | Kolb |
| 5,422,169 A | 6/1995 | Roe |
| 5,425,725 A | 6/1995 | Tanzer et al. |
| 5,429,629 A | 7/1995 | Latimer et al. |
| 5,436,066 A * | 7/1995 | Chen .......................... 442/398 |
| 5,486,167 A | 1/1996 | Dragoo et al. |
| 5,505,718 A | 4/1996 | Roe et al. |
| 5,509,915 A | 4/1996 | Hanson et al. |
| 5,522,810 A | 6/1996 | Allen, Jr. et al. |
| H1565 H | 7/1996 | Brodof et al. |
| 5,531,728 A | 7/1996 | Lash |
| 5,562,646 A | 10/1996 | Goldman et al. |
| 5,597,873 A | 1/1997 | Chambers et al. |
| 5,599,335 A | 2/1997 | Goldman et al. |
| 5,601,542 A | 2/1997 | Melius et al. |
| 5,607,550 A | 3/1997 | Akers |
| 5,613,962 A * | 3/1997 | Kenmochi et al. .......... 604/378 |
| 5,637,105 A | 6/1997 | Tanaka et al. |
| 5,649,916 A * | 7/1997 | DiPalma et al. ............ 604/378 |
| 5,651,862 A | 7/1997 | Anderson et al. |
| 5,653,702 A | 8/1997 | Brohammer et al. |
| 5,669,894 A | 9/1997 | Goldman et al. |
| 5,698,078 A | 12/1997 | Mizukami et al. |
| 5,733,273 A * | 3/1998 | Ahr ............................. 604/378 |
| 5,736,219 A | 4/1998 | Suehr et al. |
| 5,741,400 A | 4/1998 | Kwak |
| 5,788,684 A | 8/1998 | Abuto et al. |
| 5,792,129 A | 8/1998 | Johansson et al. |
| 5,792,513 A | 8/1998 | Koslow et al. |
| 5,795,439 A | 8/1998 | Euripides et al. |
| 5,821,179 A | 10/1998 | Masaki et al. |
| 5,830,202 A | 11/1998 | Bogdanski et al. |
| 5,836,929 A | 11/1998 | Bewick-Sonntag et al. |
| 5,843,059 A | 12/1998 | Niemeyer et al. |
| 5,843,063 A | 12/1998 | Anderson et al. |
| 5,843,575 A | 12/1998 | Wang et al. |
| 5,843,852 A | 12/1998 | Dutkiewicz et al. |
| 5,849,000 A | 12/1998 | Anjur et al. |
| 5,849,405 A | 12/1998 | Wang et al. |
| 5,851,672 A | 12/1998 | Wang et al. |
| 5,853,867 A | 12/1998 | Harada et al. |
| 5,855,572 A | 1/1999 | Schmidt |
| 5,858,535 A | 1/1999 | Wang et al. |
| 5,868,724 A | 2/1999 | Dierckes, Jr. et al. |
| 5,873,867 A | 2/1999 | Coles et al. |
| 5,891,120 A | 4/1999 | Chmielewski |
| 5,895,379 A | 4/1999 | Litchholt et al. |
| 5,925,439 A | 7/1999 | Haubach |
| 5,941,862 A | 8/1999 | Haynes et al. |
| 5,941,863 A | 8/1999 | Guidotti et al. |
| 5,972,487 A | 10/1999 | Duenk et al. |
| 5,977,014 A | 11/1999 | Plischke et al. |
| 6,015,608 A | 1/2000 | Koslow |
| 6,080,909 A | 6/2000 | Österdahl et al. |
| 6,086,950 A | 7/2000 | Masaki et al. |
| 6,129,717 A | 10/2000 | Fujioka et al. |
| 6,177,605 B1 | 1/2001 | Trombetta et al. |
| 6,562,742 B2 * | 5/2003 | Dutkiewicz et al. ........ 442/375 |

* cited by examiner

ABSORBENT COMPOSITE HAVING FIBROUS BANDS

CROSS-REFERENCE TO RELATED APPLICATION

This application claims the benefit of the priority of the filing date of copending U.S. application No. 60/155,464, filed Sep. 21, 1999, which is expressly incorporated herein by reference in its entirety.

FIELD OF THE INVENTION

The present invention relates to an absorbent composite and more particularly, to an absorbent composite that includes superabsorbent material and fibrous bands.

BACKGROUND OF THE INVENTION

Cellulose fibers derived from wood pulp are used in a variety of absorbent articles, for example, diapers, incontinence products, and feminine hygiene products. It is desirable for the absorbent articles to have a high absorbent capacity for liquid as well as to have good dry and wet strength characteristics for durability in use and effective fluid management. The absorbent capacity of articles made from cellulose fibers is often enhanced by the addition of superabsorbent materials, such as superabsorbent polymers. Superabsorbent polymers known in the art have the capability to absorb liquids in quantities from 5 to 100 times or more their weight. Thus, the presence of superabsorbent polymers greatly increases the liquid holding capacity of absorbent articles made from cellulose.

Because superabsorbent polymers absorb liquid and swell upon contact with liquid, superabsorbent polymers have heretofore been incorporated primarily in cellulose mats that are produced by the conventional dry, air-laid methods. Wet-laid processes for forming cellulose mats have not been used commercially because superabsorbent polymers tend to absorb liquid and swell during formation of the absorbent mats, thus requiring significant energy for their complete drying.

Cellulose structures formed by the wet-laid process typically exhibit certain properties that are superior to those of an air-laid structure. The integrity, fluid distribution, and the wicking characteristics of wet-laid cellulosic structures are superior to those of air-laid structures. Attempts to combine the advantages of wet-laid composites with the high absorbent capacity of superabsorbent materials has led to the formation of various wet-laid absorbent composites that include superabsorbent materials. Generally, these structures include superabsorbent materials distributed as a layer within a multilayered composite. In these structures the superabsorbent polymer is relatively localized and not uniformly distributed throughout the absorbent structure and thus renders these composites susceptible to gel blocking. Upon liquid absorption, superabsorbent materials tend to coalesce and form a gelatinous mass that prevents the wicking of liquid to unwetted portions of the composite. By preventing distribution of acquired liquid from a composite's unwetted portions, get blocking precludes the effective and efficient use of superabsorbent materials in fibrous composites. The diminished capacity of such fibrous composites results from narrowing of capillary acquisition and distribution channels that accompanies superabsorbent material swelling. The diminution of absorbent capacity and concomitant loss of capillary distribution channels for conventional absorbent cores that include superabsorbent material are manifested by decreased liquid acquisition rates and far from ideal liquid distribution on successive liquid insults.

Accordingly, there exists a need for an absorbent composite that includes superabsorbent material and that effectively acquires and wicks liquid throughout the composite and distributes the acquired liquid to absorbent material where the liquid is efficiently absorbed and retained without gel blocking. A need also exists for an absorbent composite that continues to acquire and distribute liquid throughout the composite on successive liquid insults. In addition, there exists a need for an absorbent composition containing superabsorbent materials that exhibits the advantages associated with wet-laid composites including wet strength, absorbent capacity and acquisition, liquid distribution, softness, and resilience. The present invention seeks to fulfill these needs and provides further related advantages.

SUMMARY OF THE INVENTION

The present invention relates to a reticulated fibrous absorbent composite containing absorbent material. The absorbent composite is a fibrous matrix that includes absorbent material and a three-dimensional network of channels or capillaries. The composite's reticulated nature enhances liquid distribution, acquisition, and wicking, while the absorbent material provides high absorbent capacity. Wet strength agents can be incorporated into the composite to provide wet integrity and also to assist in securing the absorbent material in the composite.

The absorbent composite formed in accordance with the present invention includes a stable three-dimensional network of fibers and channels that afford rapid acquisition and wicking of liquid. The fibers and channels distribute the acquired liquid throughout the composite and direct liquid to absorbent material present in the composite where the liquid is ultimately absorbed. The composite maintains its integrity before, during, and after liquid is introduced. In one embodiment, the composite is a densified composite that can recover its original volume on wetting.

In one aspect, the present invention provides an absorbent composite having a fibrous matrix that includes absorbent material. The fibrous matrix defines voids and passages between the voids, which are distributed throughout the composite. Absorbent material is located within some of the voids. The absorbent material located in these voids is expandable into the void.

In one embodiment, the reticulated absorbent composite includes at least one fibrous stratum. For such an embodiment, the composite includes a reticulated core and a fibrous stratum adjacent and coextensive with an outward facing surface of the core. In another embodiment, the composite includes strata on opposing outward facing surfaces of the core. The composite's strata can be composed of any suitable fiber or combination of fibers and can be formed from fibers that are the same as or different from the fibers used for forming the reticulated core.

In another embodiment, the absorbent composite includes fibrous bands.

In another aspect of the invention, absorbent articles that include the reticulated composite are provided. The absorbent articles include consumer absorbent products such as diapers, feminine care products, and adult incontinence products.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein.

DETAILED DESCRIPTION OF THE PREFERRED EMBODIMENT

Figure 1:
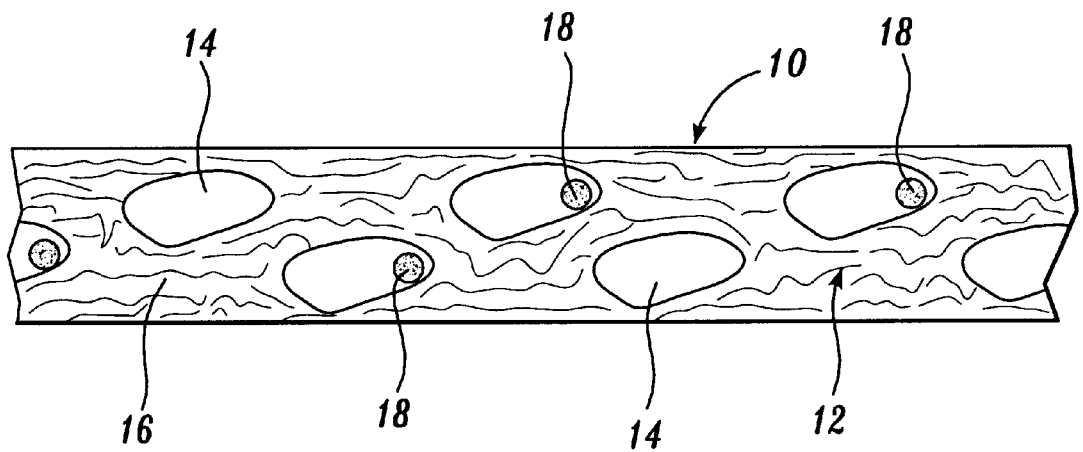
FIG. 1 is a cross-sectional view of a portion of a reticulated absorbent composite formed in accordance with the present invention.

The absorbent composite formed in accordance with the present invention is a reticulated fibrous composite that includes absorbent material. The absorbent material is distributed substantially throughout the fibrous composite and serves to absorb and retain liquid acquired by the composite.

In a preferred embodiment, the absorbent material is a superabsorbent material. In addition to forming a matrix for the absorbent material, the composite's fibers provide a stable three-dimensional network of channels or capillaries that serve to acquire liquid contacting the composite and to distribute the acquired liquid to the absorbent material. The composite optionally includes a wet strength agent that further increases tensile strength and structural integrity to the composite.

The composite is a fibrous matrix that includes absorbent material. The fibrous matrix defines voids and passages between the voids, which are distributed throughout the composite. Absorbent material is located within some of the voids. The absorbent material located in these voids is expandable into the void.

The absorbent composite can be advantageously incorporated into a variety of absorbent articles such as diapers and training pants; feminine care products including sanitary napkins, tampons, and pant liners; adult incontinence products; toweling; surgical and dental sponges; bandages; food tray pads; and the like.

Because the composite is highly absorbent having a high liquid storage capacity, the composite can be incorporated into an absorbent article as a liquid storage core. In such a construct, the composite can be combined with one or more other composites or layers including, for example, an acquisition and/or distribution layer. In a preferred embodiment, an absorbent article, such as a diaper, includes an acquisition layer overlying a reticulated storage core and having a liquid pervious facing sheet and a liquid impervious backing sheet. Because of the composite's capacity to rapidly acquire and distribute liquid, the composite can serve as a liquid management layer that acquires and transfers a portion of the acquired liquid to an underlying storage layer. Thus, in another embodiment, the absorbent composite can be combined with a storage layer to provide an absorbent core that is useful in absorbent articles.

The absorbent composite formed in accordance with the present invention is a reticulated absorbent composite. As used herein, the term "reticulated" refers to the composite's open and porous nature characterized as having a stable three-dimensional network of fibers (i.e., fibrous matrix) that create channels or capillaries that serve to rapidly acquire and distribute liquid throughout the composite, ultimately delivering acquired liquid to the absorbent material that is distributed throughout the composite.

The reticulated composite is an open and stable structure. The fibrous composite's open and stable structure includes a network of capillaries or channels that are effective in acquiring and distributing liquid throughout the composite. In the composite, fibers form relatively dense bundles that direct fluid throughout the composite and to absorbent material distributed throughout the composite. The composite's wet strength agent serves to stabilize the fibrous structure by providing interfiber bonding. The interfiber bonding assists in providing a composite having a stable structure in which the composite's capillaries or channels remain open before, during, and after liquid insult. The composite's stable structure provides capillaries that remain open after initial liquid insult and that are available for acquiring and distributing liquid on subsequent insults.

Referring to FIG. 1, a representative reticulated absorbent composite indicated generally by reference numeral 10 formed in accordance with the present invention is a fibrous matrix that includes fibrous regions 12 substantially composed of fibers 16 and defining voids 14. Some voids include absorbent material 18. Voids 14 are distributed throughout composite 10.

Figure 2:
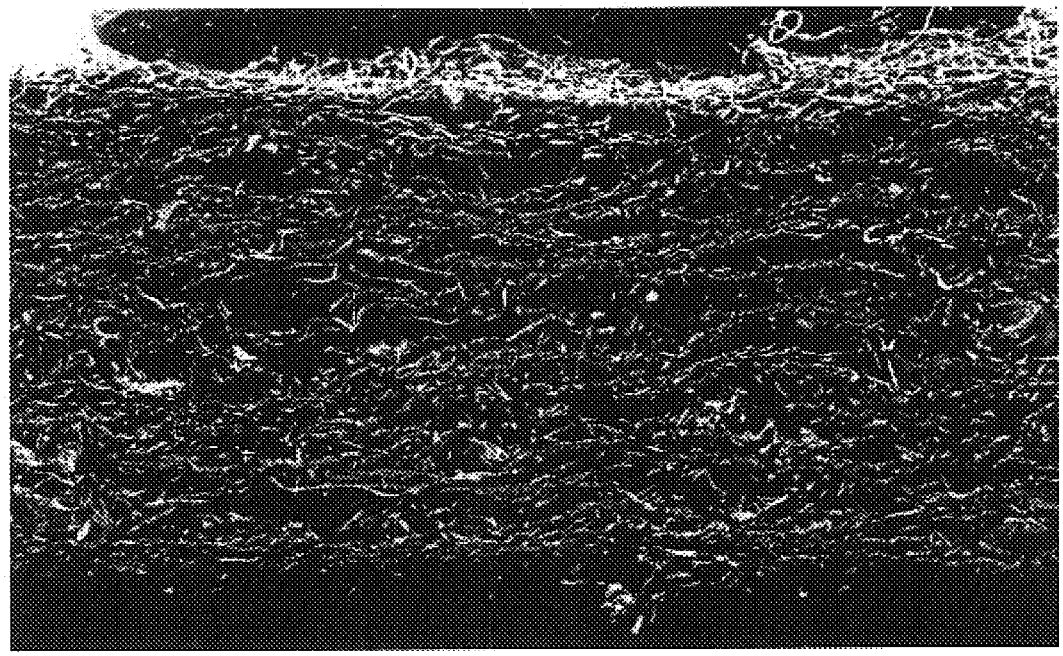
FIG. 2 is a photomicrograph of a cross section of a representative reticulated absorbent composite formed by a wet-laid method in accordance with the present invention at 12 times magnification.
Figure 3:
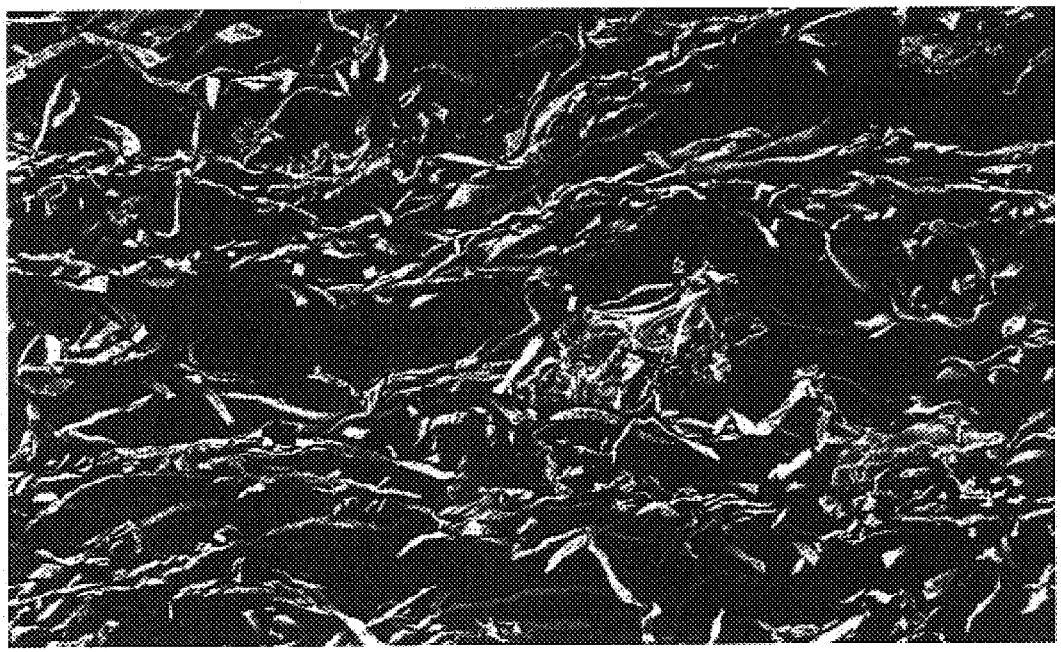
FIG. 3 is a photomicrograph of the wet-laid composite of FIG. 2 at 40 times magnification.
Figure 4:
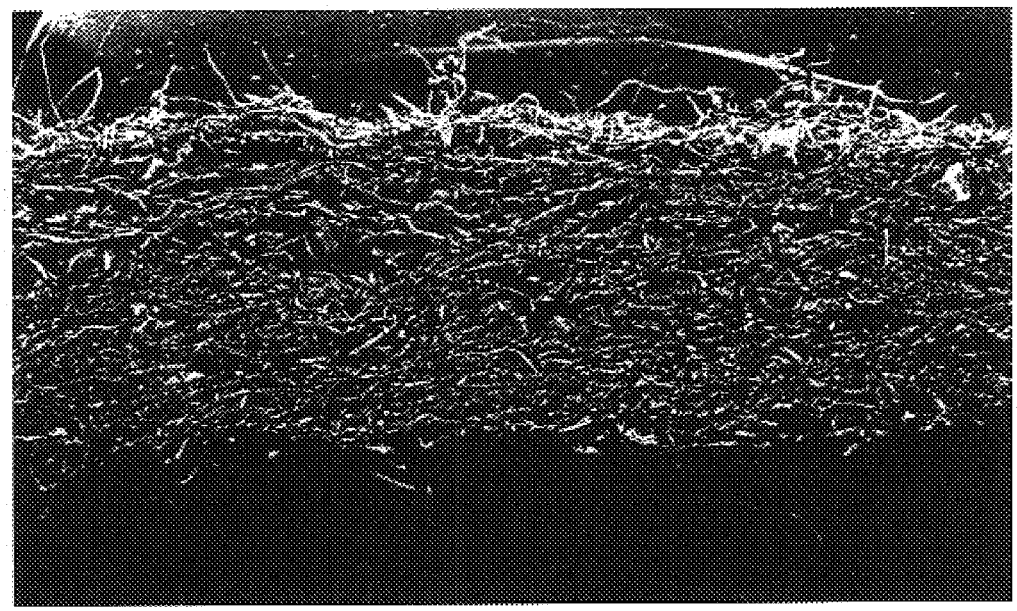
FIG. 4 is a photomicrograph of a cross section of a representative reticulated absorbent composite formed by a foam method in accordance with the present invention at 12 times magnification.
Figure 5:
FIG. 5 is a photomicrograph of the foam-formed composite of FIG. 4 at 40 times magnification.

Representative reticulated composites formed in accordance with the invention are shown in FIGS. 2–9. These composites include 48 percent by weight matrix fibers (i.e., southern pine commercially available from Weyerhaeuser Co. under the designation NB416), 12 percent by weight resilient fibers (i.e., polymaleic acid crosslinked fibers), 40 percent by weight absorbent material (i.e., superabsorbent material commercially available from Stockhausen), and about 0.5 percent by weight wet strength agent (i.e., polyamide-epichlorohydrin resin commercially available from Hercules under the designation Kymene®). FIG. 2 is a photomicrograph of a cross section of a representative composite formed by a wet-laid process at 12× magnification. FIG. 3 is a photomicrograph of the same cross section at 40× magnification. FIG. 4 is a photomicrograph of a cross section of a representative composite formed by a foam process at 12× magnification. FIG. 5 is a photomicrograph of the same cross section at 40× magnification. The reticulated nature of the composites is shown in these figures. Referring to FIG. 3, fibrous regions extend throughout the composite creating a network of channels. Void regions, including those that include absorbent material, appear throughout the composite and are in fluid communication with the composite's fibrous regions. Absorbent material appears in the composite's voids, generally surrounded by dense fiber bundles.

Figure 6:
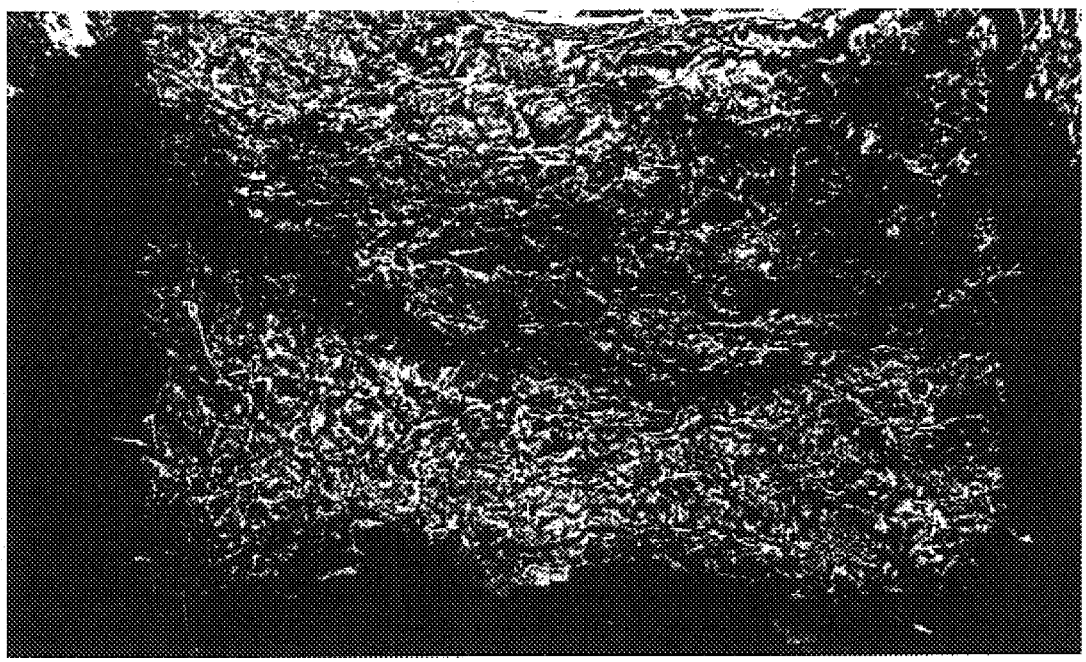
FIG. 6 is a photomicrograph of a cross section of a representative reticulated absorbent composite formed by a wet-laid method in accordance with the present invention in a wetted state at 8 times magnification.
Figure 7:
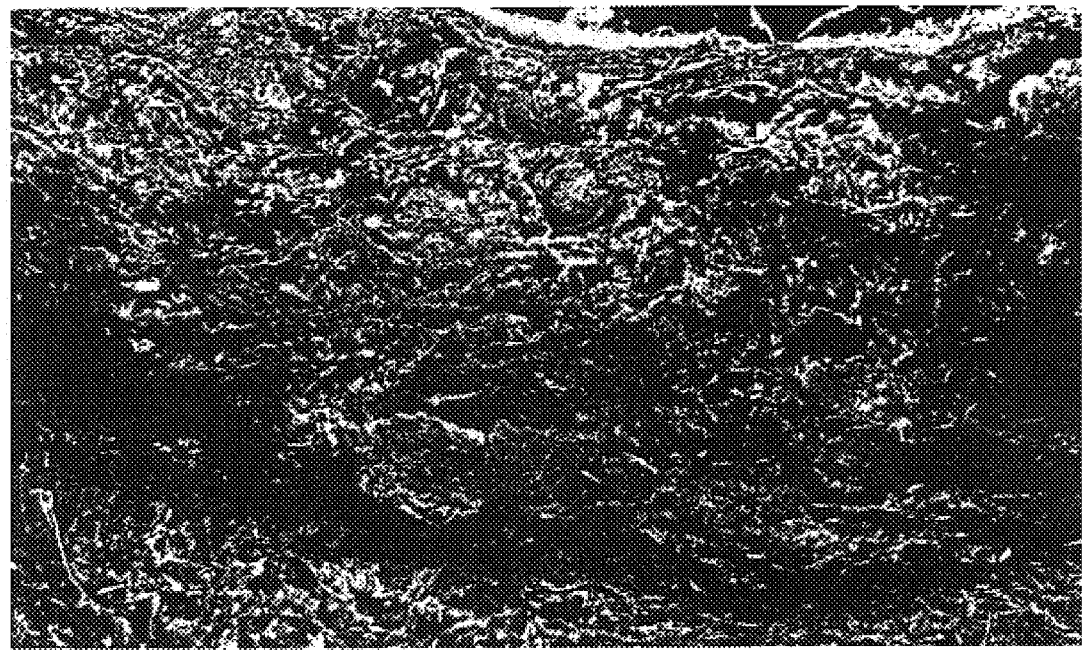
FIG. 7 is a photomicrograph of the wet-laid composite of FIG. 6 at 12 times magnification.
Figure 8:
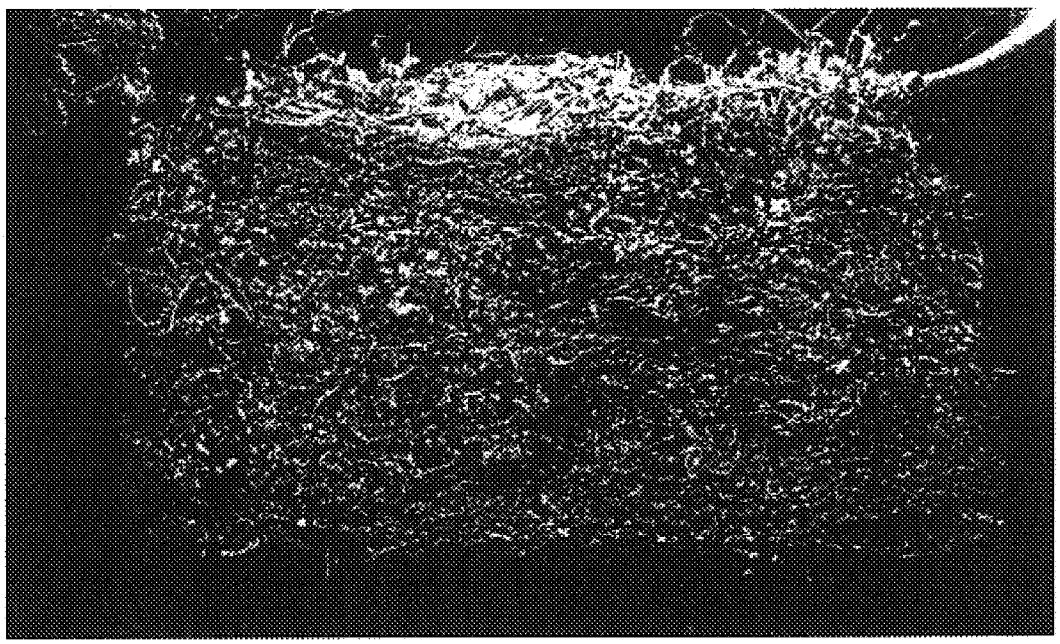
FIG. 8 is a photomicrograph of a cross section of a representative reticulated absorbent composite formed by a foam method in accordance with the present invention in a wetted state at 8 times magnification.
Figure 9:
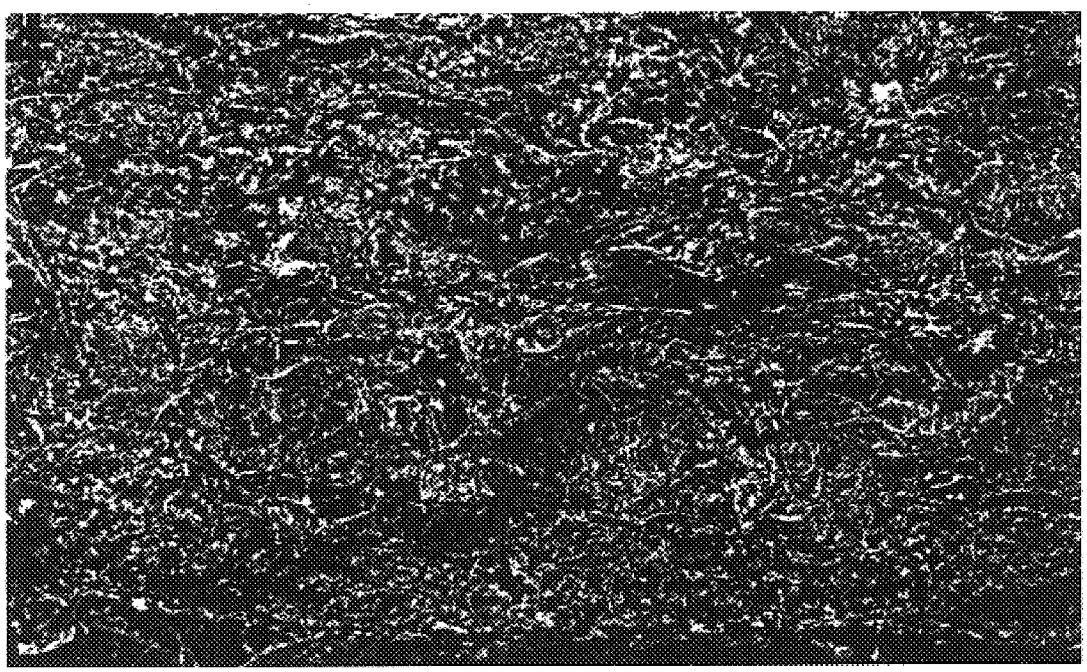
FIG. 9 is a photomicrograph of the foam-formed composite of FIG. 8 at 12 times magnification.

Photomicrographs of the representative composites shown in FIGS. 2–5 in a wetted state are illustrated in FIGS. 6–9, respectively. These photomicrographs were obtained by sectioning freeze-dried composites that had acquired synthetic urine under free swell conditions. FIGS. 6 and 7 are photomicrographs of the wetted wet-laid composite at 8× and 12× magnification, respectively. FIGS. 8 and 9 are photomicrographs of the wetted foam-formed composite at 8× and 12× magnification, respectively. Referring to FIG. 6, absorbent material in the wetted composite has swollen and increased in size to more fully occupy voids that the absorbent material previously occupied in the dry composite.

The composite's fibrous matrix is composed primarily of fibers. Generally, fibers are present in the composite in an amount from about 20 to about 90 weight percent, preferably from about 50 to about 70 weight percent, based on the total weight of the composite. Fibers suitable for use in the present invention are known to those skilled in the art and include any fiber from which a wet composite can be formed.

The composite includes resilient fibers. As used herein, the term "resilient fiber" refers to a fiber present in the composite that imparts reticulation to the composite. Generally, resilient fibers provide the composite with bulk and resiliency. The incorporation of resilient fibers into the composite allows the composite to expand on absorption of liquid without structural integrity loss. Resilient fibers also impart softness to the composite. In addition, resilient fibers offer advantages in the composite's formation processes. Because of the porous and open structure resulting from wet composites that include resilient fibers, these composites drain water relatively easily and are therefore dewatered and dried more readily than wet composites that do not include resilient fibers. Preferably, the composite includes resilient fibers in an amount from about 5 to about 60 percent by weight, more preferably from about 10 to 40 percent by weight, based on the total weight of the composite.

Resilient fibers include cellulosic and synthetic fibers. Preferred resilient fibers include chemically stiffened fibers, anfractuous fibers, chemithermomechanical pulp (CTMP), and prehydrolyzed kraft pulp (PHKP).

The term "chemically stiffened fiber" refers to a fiber that has been stiffened by chemical means to increase fiber stiffness under dry and wet conditions. Fibers can be stiffened by the addition of chemical stiffening agents that can coat and/or impregnate the fibers. Stiffening agents include the polymeric wet strength agents including resinous agents such as, for example, polyamide-epichlorohydrin and polyacrylamide resins described below. Fibers can also be stiffened by modifying fiber structure by, for example, chemical crosslinking. Preferably, the chemically stiffened fibers are intrafiber crosslinked cellulosic fibers.

Resilient fibers can include noncellulosic fibers including, for example, synthetic fibers such as polyolefin, polyamide, and polyester fibers. In a preferred embodiment, the resilient fibers include crosslinked cellulosic fibers.

As used herein, the term "anfractuous fiber" refers to a cellulosic fiber that has been chemically treated. Anfractuous fibers include, for example, fibers that have been treated with ammonia.

In addition to resilient fibers, the composite includes matrix fibers. As used herein, the term "matrix fiber" refers to a fiber that is capable of forming hydrogen bonds with other fibers. Matrix fibers are included in the composite to impart strength to the composite. Matrix fibers include cellulosic fibers such as wood pulp fibers, highly refined cellulosic fibers, and high surface area fibers such as expanded cellulose fibers. Other suitable cellulosic fibers include cotton linters, cotton fibers, and hemp fibers, among others. Mixtures of fibers can also be used. Preferably, the composite includes matrix fibers in an amount from about 10 to about 60 percent by weight, more preferably from about 20 to about 50 percent by weight, based on the total weight of the composite.

The composite preferably includes a combination of resilient and matrix fibers. In one preferred embodiment, the composite includes resilient fibers in an amount from about 5 to about 20 percent by weight and matrix fibers in an amount from about 20 to about 60 percent by weight based on the total weight of the composite. In a more preferred embodiment, the composite includes from about 10 to about 15 percent by weight resilient fibers, preferably crosslinked cellulosic fibers, and from about 40 to about 50 percent by weight matrix fibers, preferably wood pulp fibers, based on the total weight of the composite.

Cellulosic fibers are a basic component of the absorbent composite. Although available from other sources, cellulosic fibers are derived primarily from wood pulp. Suitable wood pulp fibers for use with the invention can be obtained from well-known chemical processes such as the kraft and sulfite processes, with or without subsequent bleaching. The pulp fibers may also be processed by thermomechanical, chemithermomechanical methods, or combinations thereof. The preferred pulp fiber is produced by chemical methods. Ground wood fibers, recycled or secondary wood pulp fibers, and bleached and unbleached wood pulp fibers can be used. Softwoods and hardwoods can be used. Details of the selection of wood pulp fibers are well known to those skilled in the art. These fibers are commercially available from a number of companies, including Weyerhaeuser Company, the assignee of the present invention. For example, suitable cellulose fibers produced from southern pine that are usable with the present invention are available from Weyerhaeuser Company under the designations CF416, NF405, PL416, FR516, and NB416.

The wood pulp fibers can also be pretreated prior to use with the present invention. This pretreatment may include physical treatment, such as subjecting the fibers to steam, or chemical treatment, for example, crosslinking the cellulose fibers using any one of a variety of crosslinking agents. Crosslinking increases fiber bulk and resiliency, and thereby can improve the fibers' absorbency. Generally, crosslinked fibers are twisted or crimped. The use of crosslinked fibers allows the composite to be more resilient, softer, bulkier, have better wicking, and be easier to densify than a composite that does not include crosslinked fibers. Suitable crosslinked cellulose fibers produced from southern pine are available from Weyerhaeuser Company under the designation NHB416. Crosslinked cellulose fibers and methods for their preparation are disclosed in U.S. Pat. Nos. 5,437,418 and 5,225,047 issued to Graef et al., expressly incorporated herein by reference.

Intrafiber crosslinked cellulosic fibers are prepared by treating cellulose fibers with a crosslinking agent. Suitable cellulose crosslinking agents include aldehyde and urea-based formaldehyde addition products. See, for example, U.S. Pat. Nos. 3,224,926; 3,241,533; 3,932,209; 4,035,147; 3,756,913; 4,689,118; 4,822,453; U.S. Pat. No. 3,440,135, issued to Chung; U.S. Pat. No. 4,935,022, issued to Lash et al.; U.S. Pat. No. 4,889,595, issued to Herron et al.; U.S. Pat. No. 3,819,470, issued to Shaw et al.; U.S. Pat. No. 3,658,613, issued to Steijer et al.; and U.S. Pat. No. 4,853,086, issued to Graef et al., all of which are expressly incorporated herein by reference in their entirety. Cellulose fibers have also been crosslinked by carboxylic acid crosslinking agents including polycarboxylic acids. U.S. Pat. Nos. 5,137,537; 5,183,707; and 5,190,563, describe the use of $C_2$–$C_9$ polycarboxylic acids that contain at least three carboxyl groups (e.g., citric acid and oxydisuccinic acid) as crosslinking agents.

Suitable urea-based crosslinking agents include methylolated ureas, methylolated cyclic ureas, methylolated lower alkyl cyclic ureas, methylolated dihydroxy cyclic ureas, dihydroxy cyclic ureas, and lower alkyl substituted cyclic ureas. Specific preferred urea-based crosslinking agents include dimethyldihydroxyethylene urea (DMeDHEU, 1,3-dimethyl-4,5-dihydroxy-2-imidazolidinone), dimethyloldihydroxyethylene urea (DMDHEU, 1,3-dihydroxymethyl-4,5-dihydroxy-2-imidazolidinone), dimethylol urea (DMU, bis[N-hydroxymethyl]urea), dihydroxyethylene urea (DHEU, 4,5-dihydroxy-2-imidazolidinone), and dimethylolethylene urea (DMEU, 1,3-dihydroxymethyl-2-imidazolidinone).

Suitable polycarboxylic acid crosslinking agents include citric acid, tartaric acid, malic acid, succinic acid, glutaric acid, citraconic acid, itaconic acid, tartrate monosuccinic acid, and maleic acid. Other polycarboxylic acid crosslinking agents include polymeric polycarboxylic acids such as poly(acrylic acid), poly(methacrylic acid), poly(maleic acid), poly(methylvinylether-co-maleate) copolymer, poly(methylvinylether-co-itaconate) copolymer, copolymers of acrylic acid, and copolymers of maleic acid. The use of polymeric polycarboxylic acid crosslinking agents such as polyacrylic acid polymers, polymaleic acid polymers, copolymers of acrylic acid, and copolymers of maleic acid is described in U.S. patent application Ser. No. 08/989,697, filed Dec. 12, 1997, and assigned to Weyerhaeuser Company. Mixtures or blends of crosslinking agents can also be used.

The crosslinking agent can include a catalyst to accelerate the bonding reaction between the crosslinking agent and cellulose fiber. Suitable catalysts include acidic salts, such as ammonium chloride, ammonium sulfate, aluminum chloride, magnesium chloride, and alkali metal salts of phosphorous-containing acids.

Although not to be construed as a limitation, examples of pretreating fibers include the application of surfactants or other liquids that modify the surface chemistry of the fibers. Other pretreatments include incorporation of antimicrobials, pigments, dyes and densification or softening agents. Fibers pretreated with other chemicals, such as thermoplastic and thermosetting resins, also may be used. Combinations of pretreatments also may be employed. Similar treatments can also be applied after the composite formation in post-treatment processes.

Cellulosic fibers treated with particle binders and/or densification/softness aids known in the art can also be employed in accordance with the present invention. The particle binders serve to attach other materials, such as cellulosic fiber superabsorbent polymers, as well as others, to the cellulosic fibers. Cellulosic fibers treated with suitable particle binders and/or densification/softness aids and the process for combining them with cellulose fibers are disclosed in the following U.S. patents: (1) U.S. Pat. No. 5,543,215, entitled "Polymeric Binders for Binding Particles to Fibers"; (2) U.S. Pat. No. 5,538,783, entitled "Non-Polymeric Organic Binders for Binding Particles to Fibers"; (3) U.S. Pat. No. 5,300,192, entitled "Wet Laid Fiber Sheet Manufacturing With Reactivatable Binders for Binding Particles to Binders"; (4) U.S. Pat. No. 5,352,480, entitled "Method for Binding Particles to Fibers Using Reactivatable Binders"; (5) U.S. Pat. No. 5,308,896, entitled "Particle Binders for High-Bulk Fibers"; (6) U.S. Pat. No. 5,589,256, entitled "Particle Binders that Enhance Fiber Densification"; (7) U.S. Pat. No. 5,672,418, entitled "Particle Binders"; (8) U.S. Pat. No. 5,607,759, entitled "Particle Binding to Fibers"; (9) U.S. Pat. No. 5,693,411, entitled "Binders for Binding Water Soluble Particles to Fibers"; (10) U.S. Pat. No. 5,547,745, entitled "Particle Binders"; (11) U.S. Pat. No. 5,641,561, entitled "Particle Binding to Fibers"; (12) U.S. Pat. No. 5,308,896, entitled "Particle Binders for High-Bulk Fibers"; (13) U.S. Pat. No. 5,498,478, entitled "Polyethylene Glycol as a Binder Material for Fibers"; (14) U.S. Pat. No. 5,609,727, entitled "Fibrous Product for Binding Particles"; (15) U.S. Pat. No. 5,571,618, entitled "Reactivatable Binders for Binding Particles to Fibers"; (16) U.S. Pat. No. 5,447,977, entitled "Particle Binders for High Bulk Fibers"; (17) U.S. Pat. No. 5,614,570, entitled "Absorbent Articles Containing Binder Carrying High Bulk Fibers; (18) U.S. Pat. No. 5,789,326, entitled "Binder Treated Fibers"; and (19) U.S. Pat. No. 5,611,885, entitled "Particle Binders", all expressly incorporated herein by reference.

In addition to natural fibers, synthetic fibers including polymeric fibers, such as polyolefin, polyamide, polyester, polyvinyl alcohol, and polyvinyl acetate fibers may also be used in the absorbent composite. Suitable polyolefin fibers include polyethylene and polypropylene fibers. Suitable polyester fibers include polyethylene terephthalate fibers. Other suitable synthetic fibers include, for example, nylon fibers. The absorbent composite can include combinations of natural and synthetic fibers.

In one preferred embodiment, the absorbent composite includes a combination of wood pulp fibers (e.g., Weyerhaeuser designation NB416) and crosslinked cellulosic fibers (e.g., Weyerhaeuser designation NHB416). Wood pulp fibers are present in such a combination in an amount from about 10 to about 85 weight percent by weight based on the total weight of fibers.

When incorporated into an absorbent article, the reticulated absorbent composite can serve as a storage layer for acquired liquids. To effectively retain acquired liquids, the absorbent composite includes absorbent material. As used herein, the term "absorbent material" refers to a material that absorbs liquid and that generally has an absorbent capacity greater than the cellulosic fibrous component of the composite. Preferably, the absorbent material is a water-swellable, generally water-insoluble polymeric material capable of absorbing at least about 5, desirably about 20, and preferably about 100 times or more its weight in saline (e.g., 0.9 percent saline). The absorbent material can be swellable in the dispersion medium utilized in the method for forming the composite. In one embodiment, the absorbent material is untreated and swellable in the dispersion medium. In another embodiment, the absorbent material is a coated absorbent material that is resistant to absorbing water during the composite formation process.

The amount of absorbent material present in the composite can vary greatly depending on the composite's intended use. The amount of absorbent material present in an absorbent article, such as an absorbent core for an infant's diaper, is suitably present in the composite in an amount from about 5 to about 60 weight percent, preferably from about 30 to about 50 weight percent, based on the total weight of the composite.

The absorbent material may include natural materials such as agar, pectin, and guar gum, and synthetic materials, such as synthetic hydrogel polymers. Synthetic hydrogel polymers include, for example, carboxymethyl cellulose, alkaline metal salts of polyacrylic acid, polyacrylamides, polyvinyl alcohol, ethylene maleic anhydride copolymers, polyvinyl ethers, hydroxypropyl cellulose, polyvinyl morpholinone, polymers and copolymers of vinyl sulphonic acid, polyacrylates, polyacrylamides, and polyvinyl pyridine among others. In a preferred embodiment, the absorbent material is a superabsorbent material. As used herein, a "superabsorbent material" refers to a polymeric material that is capable of absorbing large quantities of fluid by swelling and forming a hydrated gel (i.e., a hydrogel). In addition to absorbing large quantities of fluids, superabsorbent materials can also retain significant amounts of bodily fluids under moderate pressure.

Superabsorbent materials generally fall into three classes: starch graft copolymers, crosslinked carboxymethylcellulose derivatives, and modified hydrophilic polyacrylates. Examples of such absorbent polymers include hydrolyzed starch-acrylonitrile graft copolymers, neutralized starch-acrylic acid graft copolymers, saponified acrylic acid ester-vinyl acetate copolymers, hydrolyzed acrylonitrile copolymers or acrylamide copolymers, modified crosslinked polyvinyl alcohol, neutralized self-crosslinking polyacrylic acids, crosslinked polyacrylate salts, carboxylated cellulose, and neutralized crosslinked isobutylene-maleic anhydride copolymers.

Superabsorbent materials are available commercially, for example, polyacrylates from Clariant of Portsmouth, Va. These superabsorbent polymers come in a variety of sizes, morphologies, and absorbent properties (available from Clariant under trade designations such as IM 3500 and IM 3900). Other superabsorbent materials are marketed under the trademarks SANWET (supplied by Sanyo Kasei Kogyo Kabushiki Kaisha), and SXM77 (supplied by Stockhausen of Greensboro, N.C.). Other superabsorbent materials are described in U.S. Pat. No. 4,160,059; U.S. Pat. No. 4,676,784; U.S. Pat. No. 4,673,402; U.S. Pat. No. 5,002,814; U.S. Pat. No. 5,057,166; U.S. Pat. No. 4,102,340; and U.S. Pat. No. 4,818,598, all expressly incorporated herein by reference. Products such as diapers that incorporate superabsorbent materials are described in U.S. Pat. No. 3,699,103 and U.S. Pat. No. 3,670,731.

Suitable superabsorbent materials useful in the absorbent composite include superabsorbent particles and superabsorbent fibers.

In a preferred embodiment, the absorbent composite includes a superabsorbent material that swells relatively slowly for the purposes of composite manufacturing and yet swells at an acceptable rate so as not to adversely affect the absorbent characteristics of the composite or any construct containing the composite. Generally, the smaller the absorbent material, the more rapidly the material absorbs liquid.

The absorbent composite can optionally include a wet strength agent. The wet strength agent provides increased strength to the absorbent composite and enhances the composite's wet integrity. In addition to increasing the composite's wet strength, the wet strength agent can assist in binding the absorbent material, for example, superabsorbent material, in the composite's fibrous matrix.

Suitable wet strength agents include cationic modified starch having nitrogen-containing groups (e.g., amino groups) such as those available from National Starch and Chemical Corp., Bridgewater, N.J.; latex; wet strength resins such as polyamide-epichlorohydrin resin (e.g., Kymene® 557LX, Hercules, Inc., Wilmington, Del.), polyacrylamide resin (described, for example, in U.S. Pat. No. 3,556,932 issued Jan. 19, 1971 to Coscia et al.; also, for example, the commercially available polyacrylamide marketed by American Cyanamid Co., Stanford, Conn., under the trade name Parez™ 631 NC); urea formaldehyde and melamine formaldehyde resins, and polyethylenimine resins. A general discussion on wet strength resins utilized in the paper field, and generally applicable in the present invention, can be found in TAPPI monograph series No. 29, "Wet Strength in Paper and Paperboard", Technical Association of the Pulp and Paper Industry (New York, 1965).

Generally, the wet strength agent is present in the composition in an amount from about 0.01 to about 2 weight percent, preferably from about 0.1 to about 1 weight percent, and more preferably from about 0.3 to about 0.7 weight percent, based on the total weight of the composite. In a preferred embodiment, the wet strength agent useful in forming the composite is a polyamide-epichlorohydrin resin commercially available from Hercules, Inc. under the designation Kymene®. The wet and dry tensile strengths of an absorbent composite formed in accordance with the present invention will generally increase with an increasing the amount of wet strength agent. The tensile strength of a representative composite is described in Example 7.

The absorbent composite generally has a basis weight from about 50 to about 1000 g/m$^2$, preferably from about 200 to about 800 g/m$^2$. In a more preferred embodiment, the absorbent composite has a basis weight from about 300 to about 600 g/m$^2$. The absorbent composite generally has a density from about 0.02 to about 0.7 g/cm$^3$, preferably from about 0.04 to about 0.3 g/cm$^3$. In a more preferred embodiment, the absorbent composite has a density of about 0.15 g/cm$^3$.

In one embodiment, the absorbent composite is a densified composite. Densification methods useful in producing the densified composites are well known to those in the art. See, for example, U.S. Pat. No. 5,547,541 and patent application Ser. No. 08/859,743, filed May 21, 1997, entitled "Softened Fibers and Methods of Softening Fibers," assigned to Weyerhaeuser Company, both expressly incorporated herein by reference. Post-dryer densified absorbent reticulated storage composites generally have a density from about 0.1 to about 0.5 g/cm$^3$, and preferably about 0.15 g/cm$^3$. Predryer densification can also be employed. Preferably, the absorbent composite is densified by either a heated or room temperature calender roll method. See, for example, U.S. Pat. Nos. 5,252,275 and 5,324,575, both expressly incorporated herein by reference.

The composition of the reticulated absorbent composite can be varied to suit the needs of the desired end product in which it can be incorporated. In one preferred embodiment, the absorbent composite includes about 60 weight percent cellulosic fibers (about 48 percent by weight wood pulp fibers and about 12 percent by weight crosslinked cellulosic fibers), about 40 percent by weight absorbent material (e.g., superabsorbent particles), and about 0.5 percent by weight wet strength agent (e.g., polyamide-epichlorohydrin resin, Kymene®, about 10 pounds resin per ton fiber) based on the total weight of the composite.

The reticulated absorbent composite can be formed by wet-laid and foam processes known to those of ordinary skill in the pulp processing art. A representative example of a wet-laid process is described in U.S. Pat. No. 5,300,192, issued Apr. 5, 1994, entitled "Wet-laid Fiber Sheet Manufacturing with Reactivatable Binders for Binding Particles to Fibers", expressly incorporated herein by reference. Wet-laid processes are also described in standard texts, such as Casey, PULP AND PAPER, 2nd edition, 1960, Volume II, Chapter VIII—Sheet Formation. Representative foam processes useful in forming the composite are known in the art and include those described in U.S. Pat. Nos. 3,716,449; 3,839,142; 3,871,952; 3,937,273; 3,938,782; 3,947,315; 4,166,090; 4,257,754; and 5,215,627, assigned to Wiggins Teape and related to the formation of fibrous materials from foamed aqueous fiber suspensions, and "The Use of an Aqueous Foam as a Fiber-Suspending Medium in Quality Papermaking," Foams, Proceedings of a Symposium organized by the Society of Chemical Industry, Colloid and Surface Chemistry Group, R. J. Akers, Ed., Academic Press, 1976, which describes the Radfoam process, all expressly incorporated herein by reference.

In the methods, the absorbent material is incorporated into the composite during the formation of the composite. Generally, the methods for forming the reticulated absorbent composite include combining the components of the composite in a dispersion medium (e.g., an aqueous medium) to form a slurry and then depositing the slurry onto a foraminous support (e.g., a forming wire) and dewatering to form a wet composite. Drying the wet composite provides the reticulated composite.

As noted above, the reticulated composite is prepared from a combination of fibers, absorbent material, and optionally a wet strength agent in a dispersion medium. In one embodiment of the method, a slurry is formed by directly combining fibers, absorbent material, and wet strength agent in a dispersion medium. In another embodiment, the slurry is prepared by first combining fibers and the wet strength agent in a dispersion medium to provide a fibrous slurry to which is then added absorbent material in a second step. In yet another embodiment, a fibrous slurry is combined with a second slurry containing absorbent material, the combined slurry then being deposited onto the support. Alternatively, individual slurries, for example, a fibrous slurry and a slurry containing absorbent material, can be deposited onto the foraminous support through the use of a divided headbox, for example, a twin slice headbox that deposits two slurries onto a support simultaneously.

In one embodiment, the slurry or slurries containing the composite's components in a dispersion medium are deposited onto a foraminous support. Once deposited onto the support the dispersion medium begins to drain from the deposited fibrous slurry. Removal of the dispersion medium (e.g., dewatering) from the deposited fibrous slurry continues through, for example, the application of heat, pressure, vacuum, and combinations thereof, and results in the formation of a wet composite.

The reticulated absorbent composite is ultimately produced by drying the wet composite. Drying removes the remaining dispersion medium and provides an absorbent composite having the desired moisture content. Generally, the composite has a moisture content less than about 20 percent and preferably has a moisture content in the range from about 6 to about 10 percent by weight based on the total weight of the composite. Suitable composite drying methods include, for example, the use of drying cans, air floats, and through air dryers. Other drying methods and apparatus known in the pulp and paper industry may also be used. Drying temperatures, pressures, and times are typical for the equipment and methods used, and are known to those of ordinary skill in the art in the pulp and paper industry. A representative wet-laid method for forming a reticulated absorbent composite is described in Example 1.

For foam methods, the fibrous slurry is a foam dispersion that further includes a surfactant. Suitable surfactants include ionic, nonionic, and amphoteric surfactants known in the art. A representative foam method for forming a reticulated absorbent composite is described in Example 2.

The deposition of the components of the absorbent composite onto the foraminous support, followed by dewatering, results in the formation of a wet composite that includes absorbent material that may have absorbed water and, as a result, swollen in size. The wet composite containing the water-swollen absorbent material is distributed onto a support from which water (i.e., the dispersion medium) can be withdrawn and the wet composite dried. Drying causes the water-swollen absorbent material to dehydrate and decrease in size, thereby creating voids in the composite surrounding the absorbent material.

In the methods, the absorbent material preferably absorbs less than about 20 times its weight in the dispersion medium, more preferably less than about 10 times, and even more preferably less than about 5 times its weight in the dispersion medium.

Foam methods are advantageous for forming the absorbent composite for several reasons. Generally, foam methods provide fibrous webs that possess both relatively low density and relatively high tensile strength. For webs composed of substantially the same components, foam-formed webs generally have densities greater than air-laid webs and lower than wet-laid webs. Similarly, the tensile strength of foam-formed webs is substantially greater than for air-laid webs and approach the strength of wet-laid webs. Also, the use of foam forming technology allows better control of pore and void size, void size to be maximized, the orientation and uniform distribution of fibers, and the incorporation of a wide range of materials (e.g., long and synthetic fibers that cannot be readily incorporated into wet-laid processes) into the composite.

For fabrication, the reticulated absorbent composite can be formed by a foam process, preferably a process by Ahlstrom Company (Helsinki, Finland). The process encompasses desirable manufacturing efficiencies while producing a product with desirable performance characteristics.

The formation of a reticulated absorbent composite by representative wet-laid and foam processes is described in Examples 1 and 2, respectively. Absorbent properties (i.e., rewet, acquisition time, liquid distribution, dry strength, and resilience) for representative reticulated absorbent composites are described in Examples 3 and 4. Wicking and liquid distribution for a representative absorbent composite are described in Examples 5 and 6, respectively. The tensile strength of representative composites formed in accordance with the present invention is described in Example 7. The softness (i.e., Taber stiffness) of representative wet-laid and foam-formed composites is described in Example 8.

One variable that affects the absorbent composite's performance characteristics including, for example, liquid acquisition and distribution rate and absorbent capacity, is the extent of swelling of the absorbent material in the composite. The methods allow for control and variation of absorbent material swelling. Absorbent material swelling generally depends on the degree of crosslinking (e.g., surface and internal crosslinking) and the amount of water absorbed by the absorbent material. The extent of swelling depends on a number of factors, including the type of absorbent material, the concentration of absorbent material in an aqueous environment (e.g., the dispersion medium and the wet composite), and the period of time that the absorbent material remains in contact with such an environment. Generally, the lower the concentration of the absorbent material in an aqueous medium and the longer the contact time, the greater the swelling of an absorbent material. Absorbent material swelling can be minimized by dispensing the absorbent in chilled water.

In general, the greater the initial swelling of the absorbent material, the greater the void volume and, consequently, the lower the density of the resulting absorbent composite. The greater the void volume of a composite, the greater its liquid acquisition rate and, generally, the greater the composite's absorbent capacity.

As noted above, the composite's voids are formed by the hydration and swelling of absorbent material (i.e., during wet composite formation) and the subsequent dehydration and decrease in size of the absorbent material (i.e., during wet composite drying). Ultimately, the density of the composite depends on the extent to which the absorbent material absorbs liquid and swells during the formation of the wet composite, and the conditions and extent to which the wet composite incorporating the swollen absorbent material is dried. Water absorbed by the absorbent material during wet composite formation is removed from the absorbent material, decreasing its size, on drying the wet composite. The dehydration of the swollen absorbent material defines some of the voids in the fibrous composite.

Figure 10:
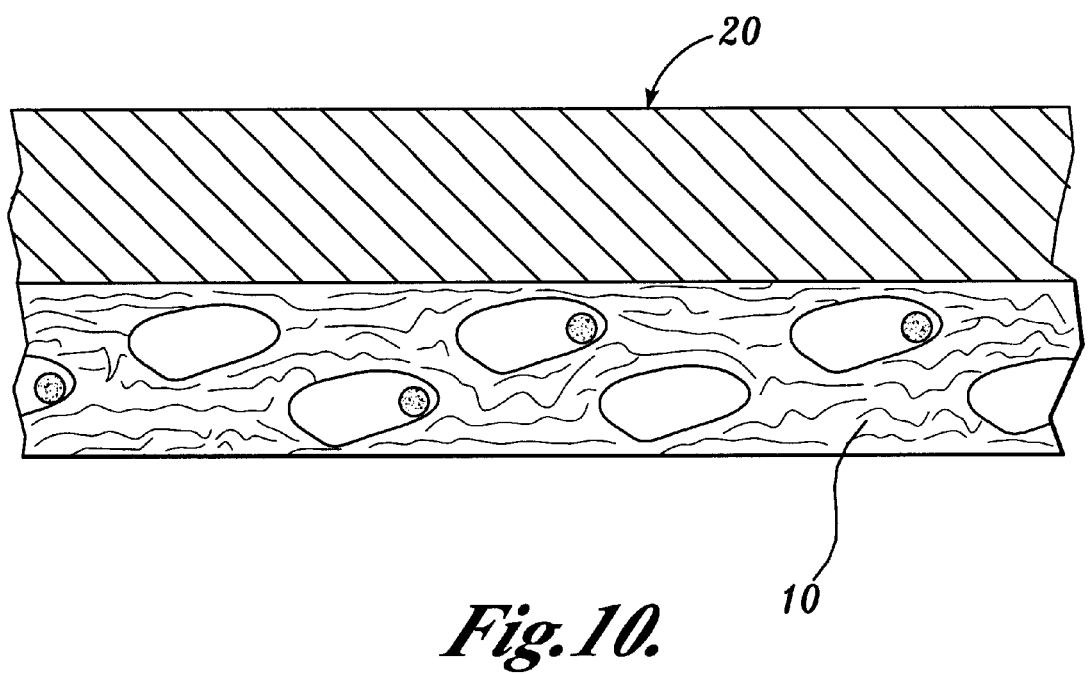
FIG. 10 is a cross-sectional view of a portion of an absorbent construct incorporating a reticulated absorbent composite formed in accordance with the present invention.
Figure 11:
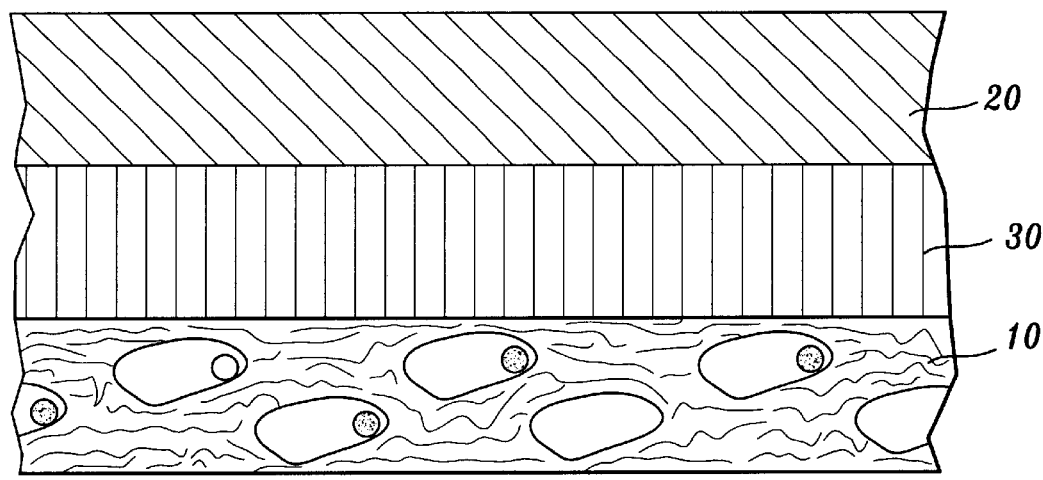
FIG. 11 is a cross-sectional view of a portion of another absorbent construct incorporating a reticulated absorbent composite formed in accordance with the present invention.

The reticulated absorbent composite can be incorporated as an absorbent core or storage layer in an absorbent article including, for example, a diaper or feminine care product. The absorbent composite can be used alone or, as illustrated in FIGS. 10 and 11, can be used in combination with one or more other layers. In FIG. 10, absorbent composite 10 is employed as a storage layer in combination with upper acquisition layer 20. As illustrated in FIG. 11, a third layer 30 (e.g., distribution layer) can also be employed, if desired, with absorbent composite 10 and acquisition layer 20.

A variety of suitable absorbent articles can be produced from the absorbent composite. The most common include absorptive consumer products, such as diapers, feminine hygiene products such as feminine napkins, and adult incontinence products. For example, referring to FIG. 12, absorbent article 40 comprises absorbent composite 10 and overlying acquisition layer 20. A liquid pervious facing sheet 22 overlies acquisition composite 20, and a liquid impervious backing sheet 24 underlies absorbent composite 10. The absorbent composite will provide advantageous liquid absorption performance for use in, for example, diapers. The reticulated structure of the absorbent composite will aid in fluid transport and absorption in multiple wettings. For absorbent articles that incorporate the composite and that are suitable for use as diapers or as incontinence products, the articles can further include leg gathers.

Figure 12A:
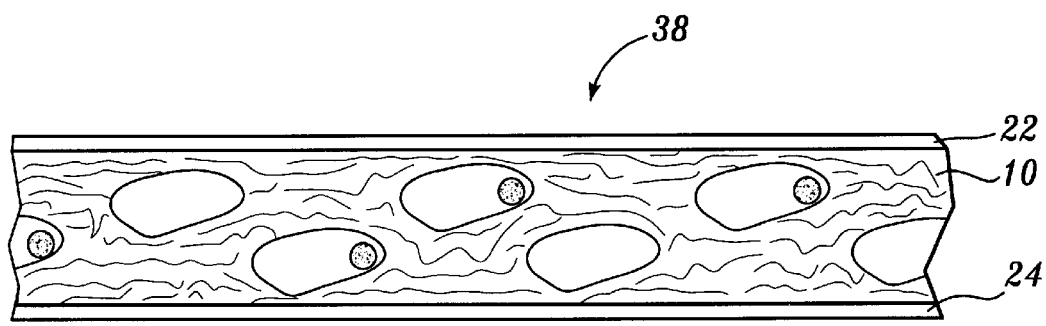
FIG. 12 is a cross-sectional view of a portion of an absorbent article incorporating a reticulated absorbent composite formed in accordance with the present invention.
Figure 12B:
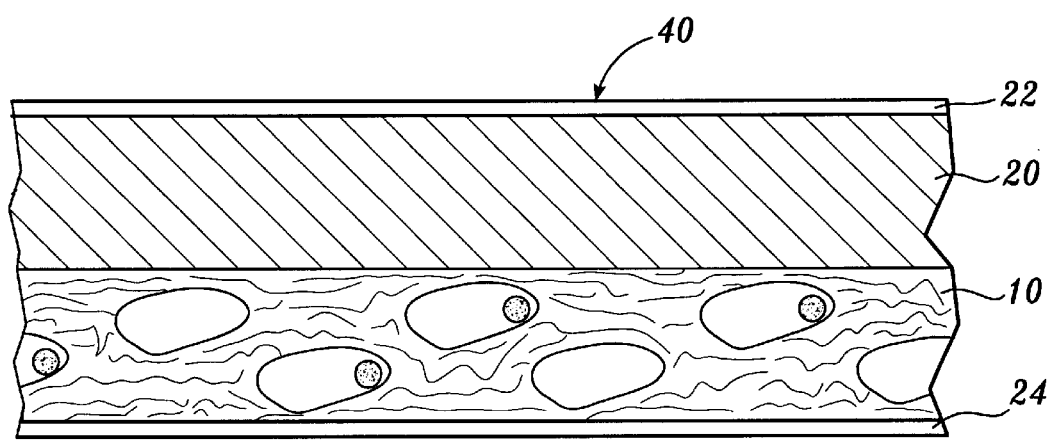
Figure 13:
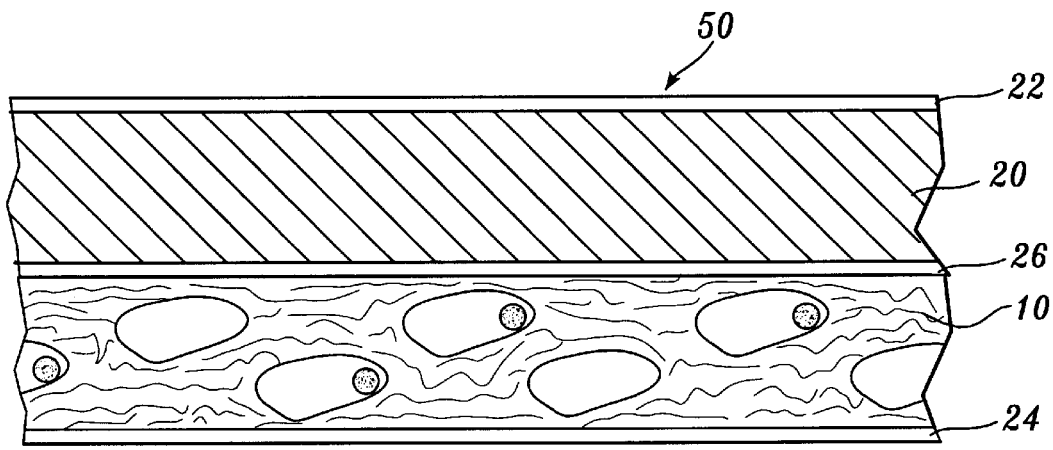
FIG. 13 is a cross-sectional view of a portion of another absorbent article incorporating a reticulated absorbent composite formed in accordance with the present invention.

The construct in FIG. 12 is shown for purposes of exemplifying a typical absorbent article, such as a diaper or feminine napkin. One of ordinary skill will be able to make a variety of different constructs using the concepts taught herein. The example, a typical construction of an adult incontinence absorbent structure is shown in FIG. 13. The article 50 comprises a facing sheet 22, acquisition layer 20, absorbent composite 10, and a backing sheet 24. The facing sheet 22 is pervious to liquid while the backing sheet 24 is impervious to liquid. In this construct, a liquid pervious tissue 26 composed of a polar, fibrous material is positioned between absorbent composite 10 and acquisition layer 20.

Figure 14:
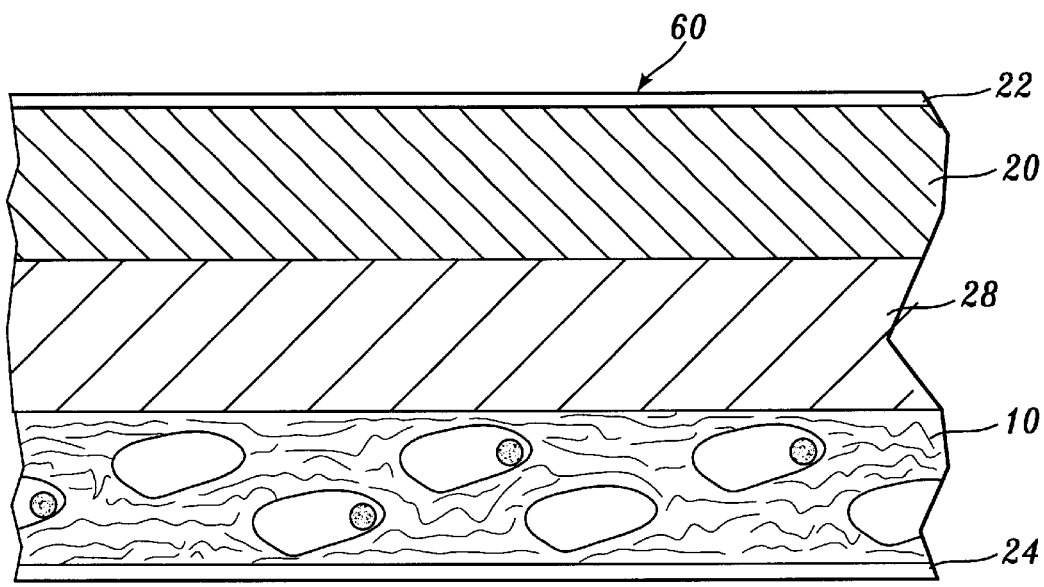
FIG. 14 is a cross-sectional view of a portion of another absorbent article incorporating a reticulated absorbent composite formed in accordance with the present invention.

Referring to FIG. 14, another absorbent article includes a facing sheet 22, an acquisition layer 20, an intermediate layer 28, absorbent composite 10, and a backing sheet 24. The intermediate layer 28 contains, for example, a densified fibrous material such as a combination of cellulose acetate and triacetin, which are combined prior to forming the article. The intermediate layer 28 can thus bond to both absorbent composite 10 and acquisition layer 20 to form an absorbent article having significantly more integrity than one in which the absorbent composite and acquisition layer are not bonded to each other. The hydrophilicity of layer 28 can be adjusted in such a way as to create a hydrophilicity gradient among layers 10, 28, and 20.

Figure 15:
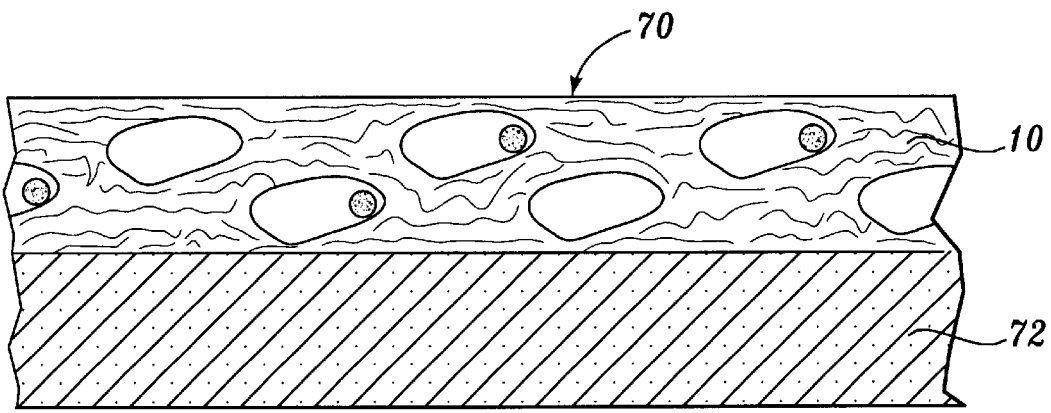
FIG. 15 is a cross-sectional view of a portion of an absorbent construct incorporating a reticulated absorbent composite formed in accordance with the present invention.

The reticulated absorbent composite can also be incorporated as a liquid management layer in an absorbent article such as a diaper. In such an article, the composite can be used in combination with a storage core or layer. In the combination, the liquid management layer can have a top surface area that is smaller, the same size, or greater than the top surface area of the storage layer. Representative absorbent constructs that incorporate the reticulated absorbent composite in combination with a storage layer are shown in FIG. 15. Referring to FIG. 15, absorbent construct 70 includes reticulated composite 10 and storage layer 72. Storage layer 72 is preferably a fibrous layer that includes absorbent material. The storage layer can be formed by any method, including air-laid, wet-laid, and foam-forming methods. The storage layer can be a reticulated composite.

Figure 16:
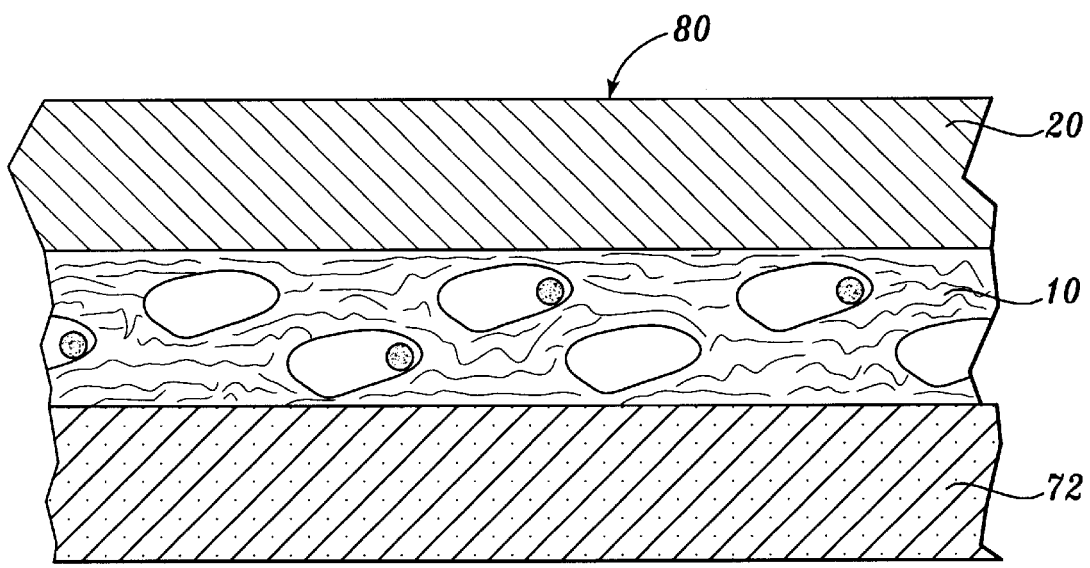
FIG. 16 is a cross-sectional view of a portion of another absorbent construct incorporating a reticulated absorbent composite formed in accordance with the present invention.
Figure 17:
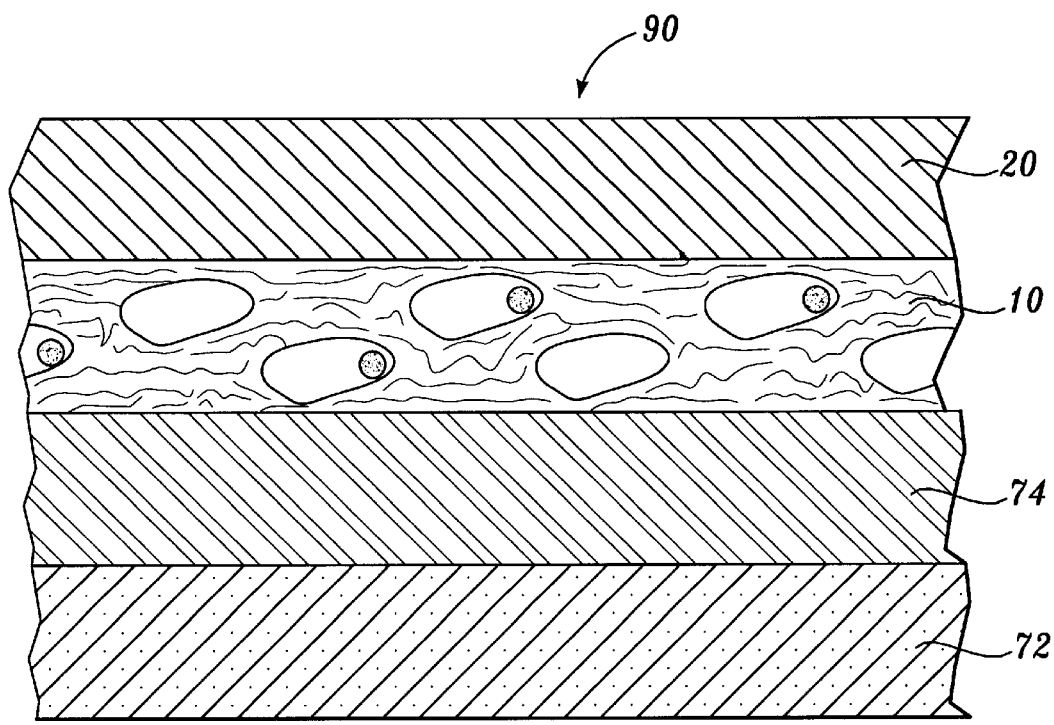
FIG. 17 is a cross-sectional view of a portion of another absorbent construct incorporating a reticulated absorbent composite formed in accordance with the present invention.

An acquisition layer can be combined with the reticulated composite and storage layer. FIG. 16 illustrates absorbent construct 80 having acquisition layer 20 overlying composite 10 and storage layer 72. Construct 80 can further include intermediate layer 74 to provide construct 90 shown in FIG. 17. Intermediate layer 74 can be, for example, a tissue layer, a nonwoven layer, an air-laid or wet-laid pad, or a reticulated composite.

Figure 18:
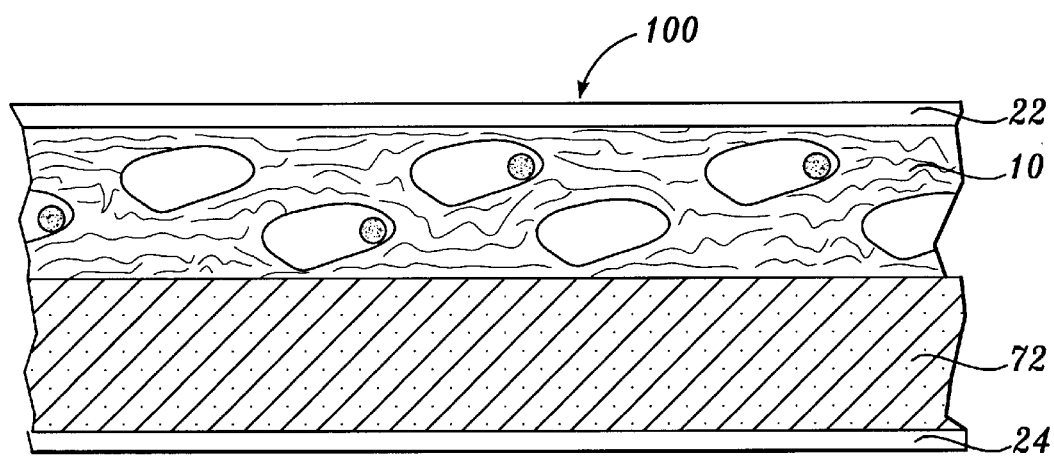
FIG. 18 is a cross-sectional view of a portion of an absorbent article incorporating a reticulated absorbent composite formed in accordance with the present invention.
Figure 19:
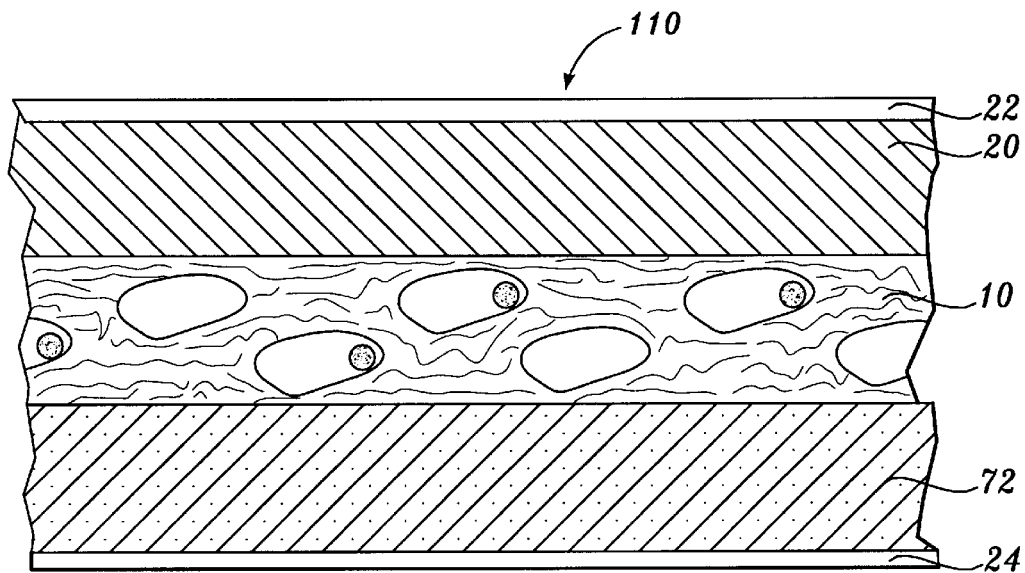
FIG. 19 is a cross-sectional view of a portion of another absorbent article incorporating a reticulated absorbent composite formed in accordance with the present invention.
Figure 20:
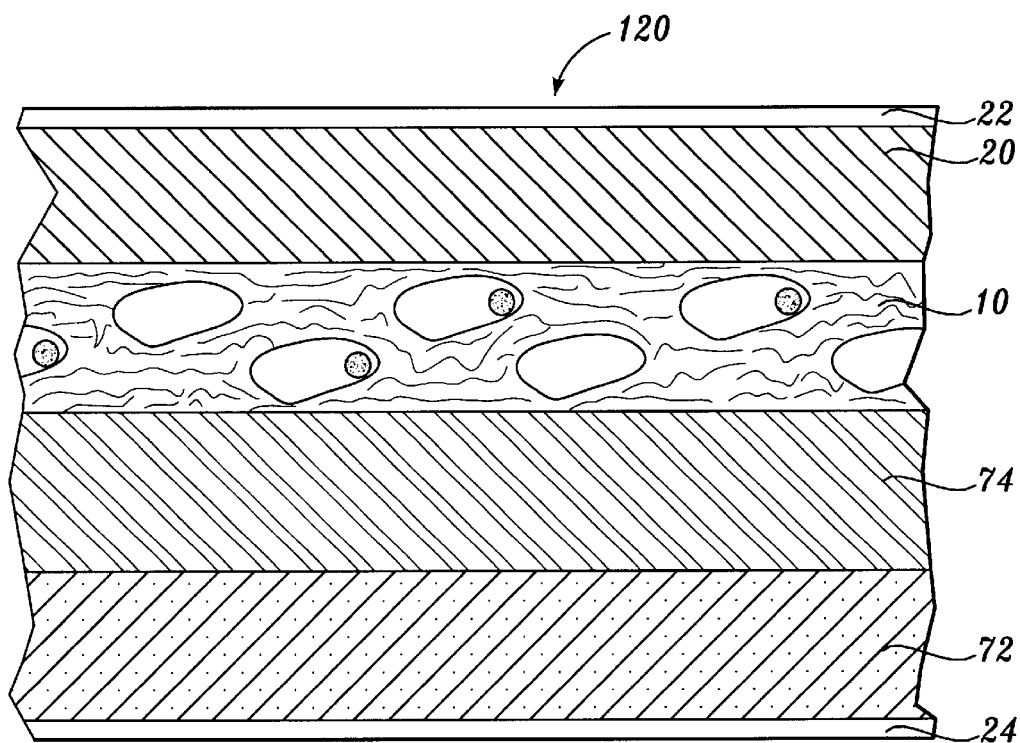
FIG. 20 is a cross-sectional view of a portion of another absorbent article incorporating a reticulated absorbent composite formed in accordance with the present invention.

Constructs 70, 80, and 90 can be incorporated into absorbent articles. Generally, absorbent articles 100, 110, and 120, shown in FIGS. 18–20, respectively, include a liquid pervious facing sheet 22, a liquid impervious backing sheet 24, and constructs 70, 80, and 90, respectively. In such absorbent articles, the facing sheet is joined to the backing sheet.

Figure 21A:
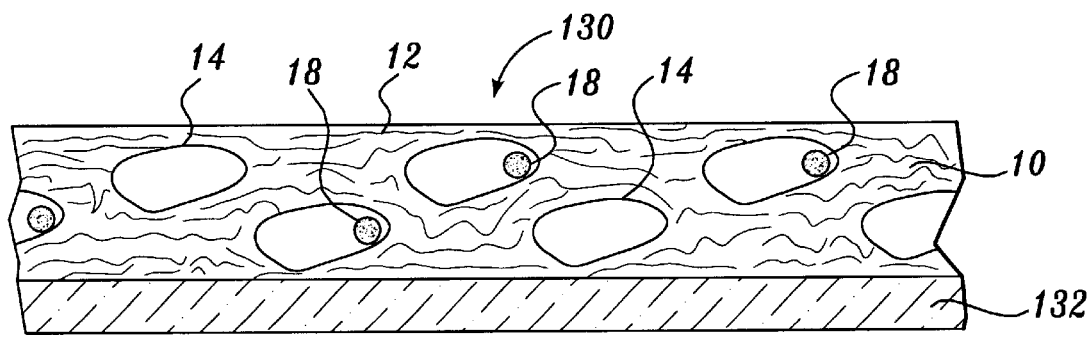
FIGS. 21A and B are cross-sectional views of portions of reticulated absorbent composites formed in accordance with the present invention.
Figure 21B:
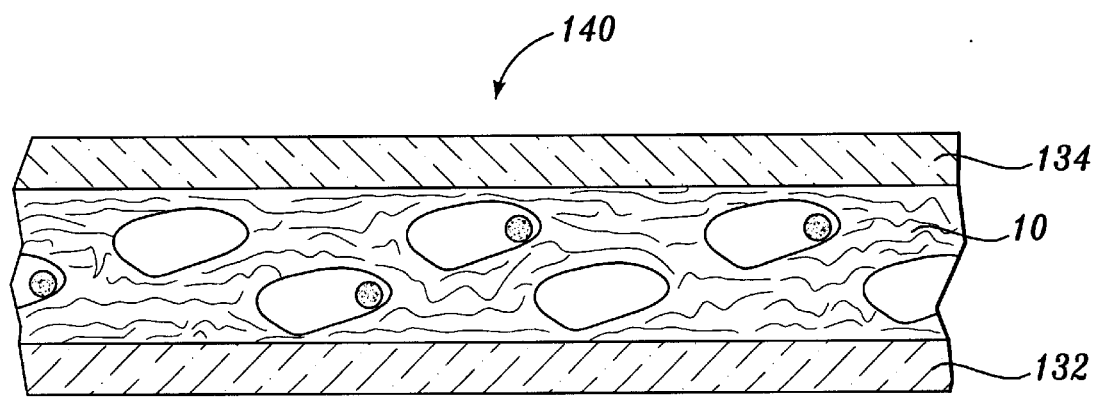

In another embodiment, the reticulated absorbent composite formed in accordance with the present invention further includes a fibrous stratum. In this embodiment, the composite includes a reticulated core and a fibrous stratum adjacent an outward facing surface of the core. The fibrous stratum is integrally formed with the reticulated core to provide a unitary absorbent composite. Generally, the stratum is coextensive with an outward facing surface (i.e., an upper and/or lower surface) of the composite. Preferably, the composite includes first and second strata adjacent each of the core's outward facing surfaces (i.e., the strata are coextensive with opposing surfaces of the core). A representative absorbent composite having a fibrous stratum is shown in FIG. 21A and a representative composite having fibrous strata is shown in FIG. 21B. Referring to FIG. 21A, absorbent composite 130 includes reticulated core 10 and stratum 132 and, as shown in FIG. 21B, composite 140 includes reticulated core 10 intermediate strata 132 and 134. As noted above, core 10 is a fibrous matrix that includes fibrous regions 12 defining voids 14, some of which include absorbent material 18.

The stratum or strata of the composite are fibrous and can be composed of any suitable fiber or combination of fibers noted above. The stratum's fibrous composition can be widely varied. The stratum can be formed from fibers that are the same as or different from the fibers used for forming the reticulated core. The stratum can be formed from resilient fibers, matrix fibers, or combinations of resilient and matrix fibers. The stratum can optionally include a wet or dry strength agent. Suitable strata can be formed from a single fiber type, for example, a stratum composed of 100 percent wood pulp fibers (e.g.; southern pine fibers). Alternatively, the stratum can be formed from fibrous blends, such as an 80:20 blend of wood pulp fibers and crosslinked fibers, and synthetic blends, and blends of synthetic and cellulosic fibers.

The stratum composition can be varied to provide a composite having desired characteristics. For example, to provide a stratum having high liquid wicking capacity, the stratum preferably has a relatively high wood pulp fiber content. Thus, for liquid distribution, the stratum is preferably composed of wood pulp fibers such as southern pine fibers. However, such a stratum has a lower liquid acquisition rate compared to a similarly constituted stratum containing relatively less wood pulp fiber and, for example, greater amounts of crosslinked fibers. Conversely, to provide a stratum having a high liquid acquisition rate, the stratum preferably has a relatively high crosslinked or synthetic fiber content. However, as a consequence of its high crosslinked fiber content, such a stratum provides less liquid distribution than a comparable stratum that includes relatively less crosslinked fiber. For liquid acquisition, the stratum is preferably a blend of crosslinked fibers and pulp fibers, for example, the stratum can include from about 30 to about 50 percent by weight crosslinked fibers and from about 50 to about 70 percent by weight pulp fibers. Alternatively, strata having high liquid acquisition rates can also include, in combination with cellulosic fibers, a relatively high synthetic fiber content (e.g., PET fibers or a blend of PET and thermobondable fibers). Optionally, one or both strata can include synthetic fibers.

Because the composite's stratum is formed with the reticulated core to provide an integrated unitary structure, the overall characteristics of the composite can be optimized by appropriate selection of the individual core and stratum components. To further optimize the performance of the composite, the nature of first and second strata can be selectively and independently controlled and varied. The compositions of the first and second strata need not be the same. The strata can be formed from the same or different fiber furnishes. For compositions formed by foam methods, stratum basis weight can also be independently controlled and varied. Stratum basis weight can also be varied with respect to the core's basis weight. In a foam method, basis weight can be varied by adjusting the rate at which the fibrous furnish is supplied to and deposited on the forming support. For example, varying pump speed for a specific furnish effectively controls the basis weight of that portion of the composite. Accordingly, in one embodiment, the absorbent composite includes a reticulated core intermediate first and second strata, each stratum having a different basis weight. Stratum basis weights can also be varied for absorbent composites formed by wet-laid methods.

The stratum can be integrally formed with the reticulated core by wet-laid and foam methods. Generally, the composite including the reticulated core and strata can be formed by substantially simultaneously depositing fibrous slurries that include the core and stratum components. The deposition of more than a single fibrous slurry onto a forming support can be accomplished by standard devices known in the art including, for example, divided and/or multislice headboxes.

Representative absorbent composites can be formed using conventional papermaking machines including, for example, Rotoformer, Fourdrinier, and twin-wire machines. Absorbent composites having a single stratum can be formed by Rotoformer and Fourdrinier machines, and composites that include two strata can be formed by twin-wire machines. A representative method for forming the absorbent composite using a Rotoformer machine is described in Example 9. The performance characteristics of representative absorbent composites formed by the method are described in Examples 10–15. Absorbent composites formed using the Rotoformer machine include a wire-side fibrous stratum. The stratum thickness and overall composite structure can be controlled by the position of headbox spargers, which deliver absorbent material to and effectively mix the absorbent material with the fiber stock. Generally, the deeper the sparger introduces the absorbent material into the fiber stock at the Rotoformer drum, the thinner the resulting stratum. Conversely, a relatively thicker stratum can be formed by introducing absorbent material into the fiber stock at a greater distance from the drum.

Figure 22:
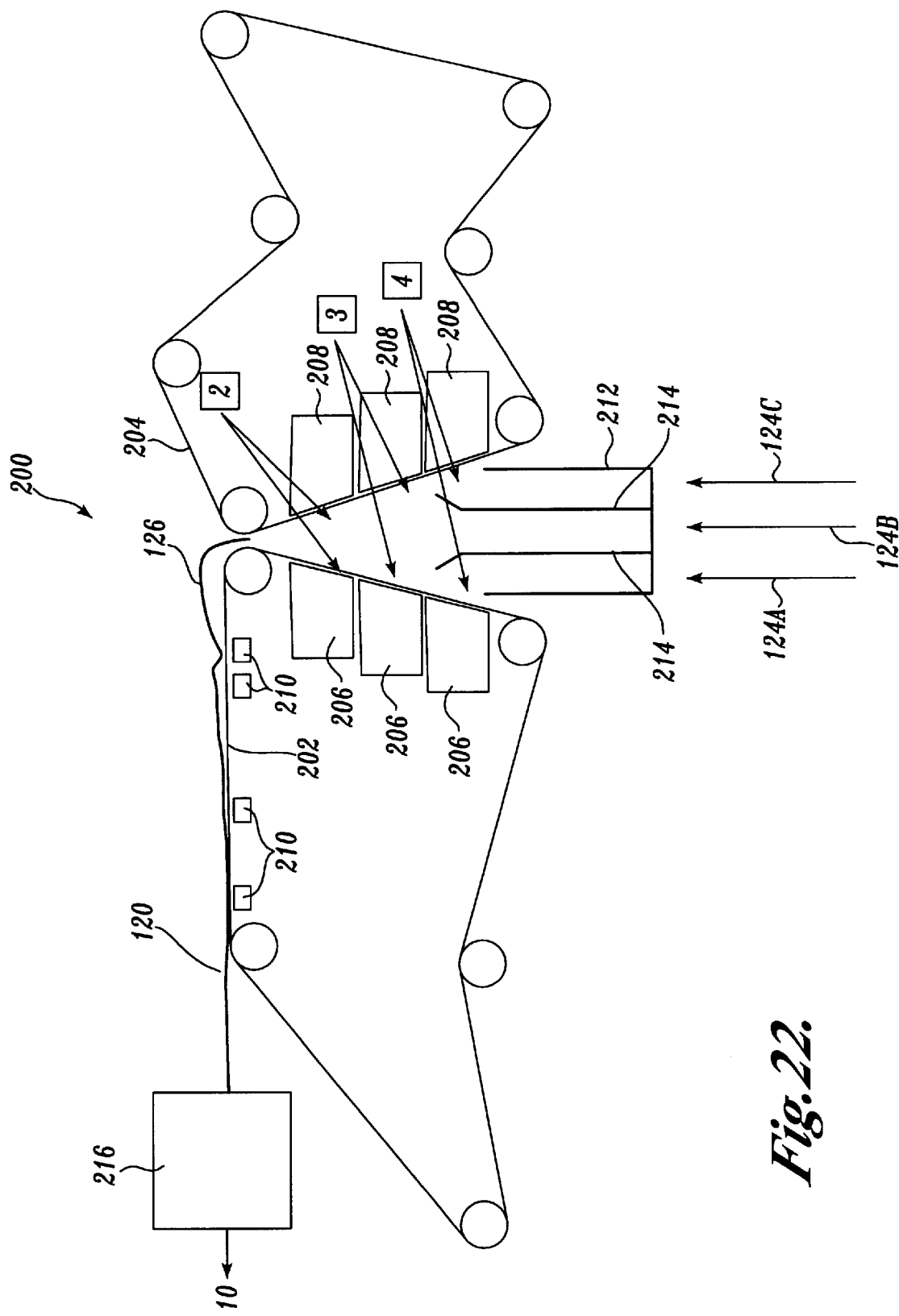
FIG. 22 is a diagrammatic view illustrating a twin-wire device and method for forming the composite of the present invention.

The absorbent composite can be formed by devices and processes that include a twin-wire configuration (i.e., twin-forming wires). A representative twin-wire machine for forming composites is shown in FIG. 22. Referring to FIG. 22, machine 200 includes twin-forming wires 202 and 204 onto which the composite's components are deposited. Basically, fibrous slurry 124 is introduced into headbox 212 and deposited onto forming wires 202 and 204 at the headbox exit. Vacuum elements 206 and 208 dewater the fibrous slurries deposited on wires 202 and 204, respectively, to provide partially dewatered webs that exit the twin-wire portion of the machine as partially dewatered web 126. Web 126 continues to travel along wire 202 and continues to be dewatered by additional vacuum elements 210 to provide wet composite 120 which is then dried by drying means 216 to provide composite 10.

Absorbent material can be introduced into the fibrous web at any one of several positions in the twin-wire process depending on the desired product configuration. Referring to FIG. 22, absorbent material 122 can be injected into the partially dewatered web at positions 2, 3, or 4, or other positions along wires 202 and 204 where the web has been at least partially dewatered. Absorbent material can be introduced into the partially dewatered web formed and traveling along wire 202 and/or 204. Absorbent material can be injected into the partially dewatered fibrous webs by nozzles spaced laterally across the width of the web. The nozzles are connected to an absorbent material supply. The nozzles can be positioned in various positions (e.g., positions 1, 2, or 3 in FIG. 22) as described above. For example, referring to FIG. 22, nozzles can be located at positions 2 to inject absorbent material into partially dewatered webs on wires 202 and 204.

Depending on the position of absorbent material introduction, the twin-wire method for forming the composite can provide a composite having a fibrous stratum.

The composite can include integrated phases having fibrous strata coextensive with the outward surfaces of the composite. These fibrous composites can be formed from multilayered inclined formers or twin-wire formers with sectioned headboxes. These methods can provide stratified or phased composites having strata or phases having specifically designed properties and containing components to attain composites having desired properties.

Basically, the position of the absorbent material in the composite's z-direction effectively defines the fibrous stratum covering the band. For a formation method that includes a single fiber furnish, the band position can be adjusted by positioning the absorbent material injection system (e.g., nozzle set) in relation to the forming wire. For methods that include multiple furnishes, the upper and lower strata can be composed of the same or different components and introduced into a sectioned headbox.

Referring to FIG. 22, composite 10 having strata 11 can be formed by machine 200. For composites in which strata 11 comprise the same components, a single fiber furnish 124 is introduced into headbox 212. For forming composites having strata 11 comprising different components, headbox 212 includes one or more baffles 214 for the introduction of fiber furnishes (e.g., 124a, 124b, and 124c) having different compositions. In such a method, the upper and lower strata can be formed to include different components and have different basis weights and properties.

Preferably, the reticulated composite is formed by a foam-forming method using the components described above. In the foam-forming method, fibrous webs having multiple strata and including absorbent material can be formed from multiple fibrous slurries. In a preferred embodiment, the foam-forming method is practiced on a twin-wire former.

The method can provide a variety of multiple strata composites including, for example, composites having three strata. A representative composite having three strata includes a first stratum formed from fibers (e.g., synthetic fibers, cellulosic, and/or binder fibers); an intermediate stratum formed from fibers and/or other absorbent material such as superabsorbent material; and a third stratum formed from fibers. The method of the invention is versatile in that such a composite can have relatively distinct and discrete strata or, alternatively, have gradual transition zones from stratum-to-stratum.

A representative method for forming a fibrous web having an intermediate stratum generally includes the following steps:

(a) forming a first fibrous slurry comprising fibers and a surfactant in an aqueous dispersion medium;

(b) forming a second fibrous slurry comprising fibers and a surfactant in an aqueous dispersion medium;

(c) moving a first foraminous element (e.g., a forming wire) in a first path;

(d) moving a second foraminous element in a second path;
(e) passing the first slurry into contact with the first foraminous element moving in a first path;
(f) passing the second slurry into contact with the second foraminous element moving in the second path;
(g) passing a third material between the first and second slurries such that the third material does not contact either of the first or second foraminous elements; and
(h) forming a fibrous web from the first and second slurries and third material by withdrawing liquid from the slurries through the first and second foraminous elements.

As noted above, the method is suitably carried out on a twin-wire former, preferably a vertical former, and more preferably, a vertical downflow twin-wire former. In the vertical former, the paths for the foraminous elements are substantially vertical.

Figure 23:
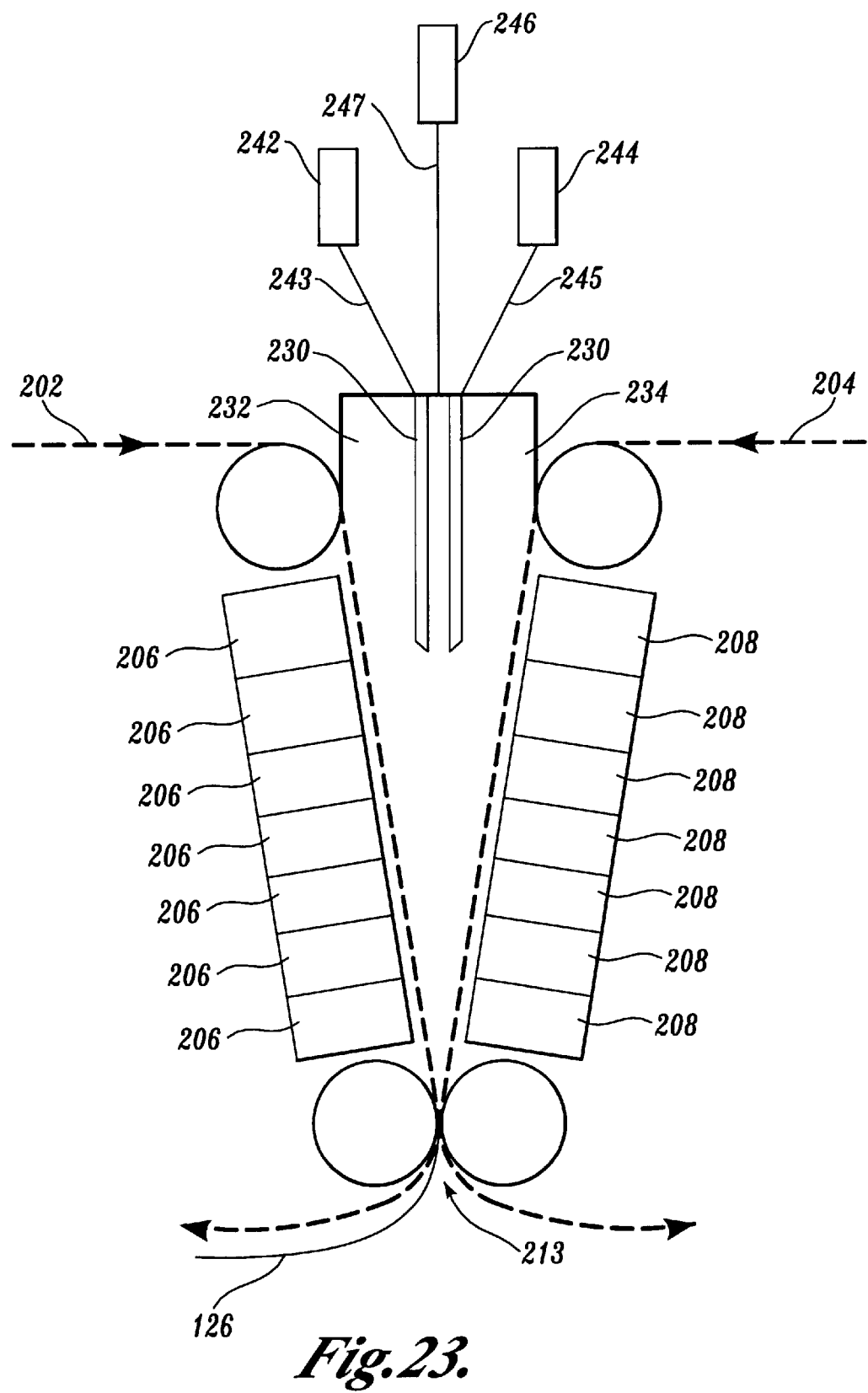
FIG. 23 is a diagrammatic view illustrating a representative headbox assembly and method for forming the composite of the present invention.

A representative vertical downflow twin-wire former useful in practicing the method of the invention is illustrated in FIG. 23. Referring to FIG. 23, the former includes a vertical headbox assembly having a former with a closed first end (top), closed first and second sides and an interior volume. A second end (bottom) of the former is defined by moving first and second foraminous elements, 202 and 204, and forming nip 213. The interior volume defined by the former's closed first end, closed first and second sides, and first and second foraminous elements includes an interior structure 230 extending from the former first end and toward the second end. The interior structure defines a first volume 232 on one side thereof and a second volume 234 on the other side thereof. The former further includes supply 242 and means 243 for introducing a first fiber slurry into the first volume, supply 244 and means 245 for introducing a second fiber slurry into the second volume, and supply 246 and means 247 for introducing a third material into the interior structure. Means for withdrawing liquid (and/or foam) (e.g., suction boxes 206 and 208) from the first and second slurries through the foraminous elements to form a web are also included in the headbox assembly.

In the method, the twin-wire former includes a means for introducing at least a third material through the interior structure. Preferably, the introducing means include at least a first plurality of conduits having a first effective length. A second plurality of conduits having a second effective length different from the first length may also be used. More than two sets of conduits can also be used.

Figure 24:
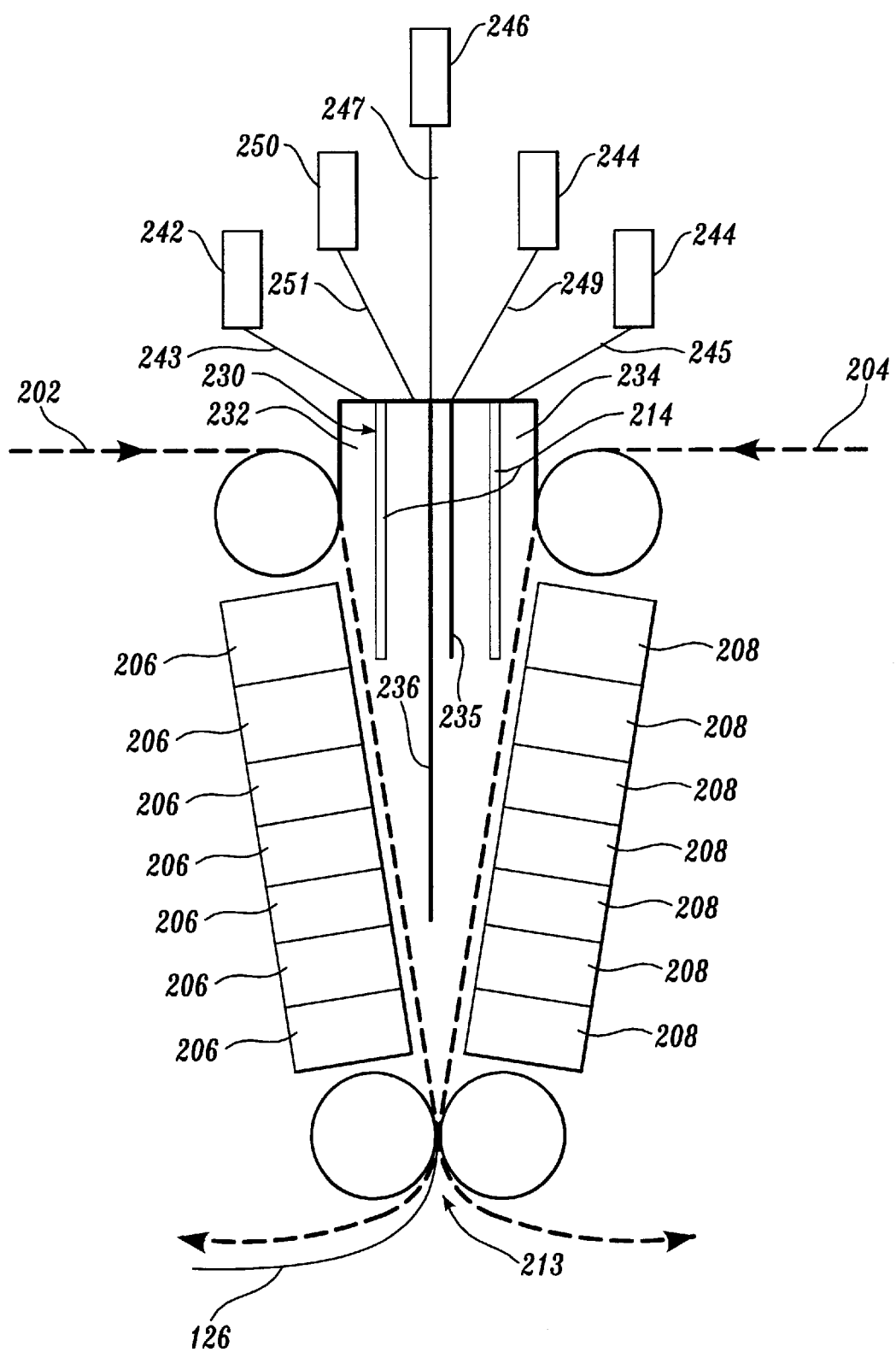
FIG. 24 is a diagrammatic view illustrating a representative headbox assembly and method for forming the composite of the present invention.

Another representative vertical downflow twin-wire former useful in practicing the forming method is illustrated in FIG. 24. Referring to FIG. 24, the former includes a vertical headbox assembly having an interior volume defined by the former's closed first end, closed first and second sides, and first and second foraminous elements, 202 and 204, and includes an interior structure 230 extending from the former first end and toward the second end. In this embodiment, interior structure 230 includes plurality of conduits 235 and 236, and optional divider walls 214.

The interior structure defines a first volume 232 on one side thereof and a second volume 234 on the other side thereof. The former further includes supply 242 and means 243 for introducing a first fiber slurry into the first volume, supply 244 and means 245 for introducing a second fiber slurry into the second volume, supply 246 and means 247 for introducing a third material into plurality of conduits 236, supply 248 and means 249 for introducing a third material into plurality of conduits 235, and supply 250 and means 251 for introducing another material, such as a foam slurry, within the volume defined by walls 214.

Figure 25:
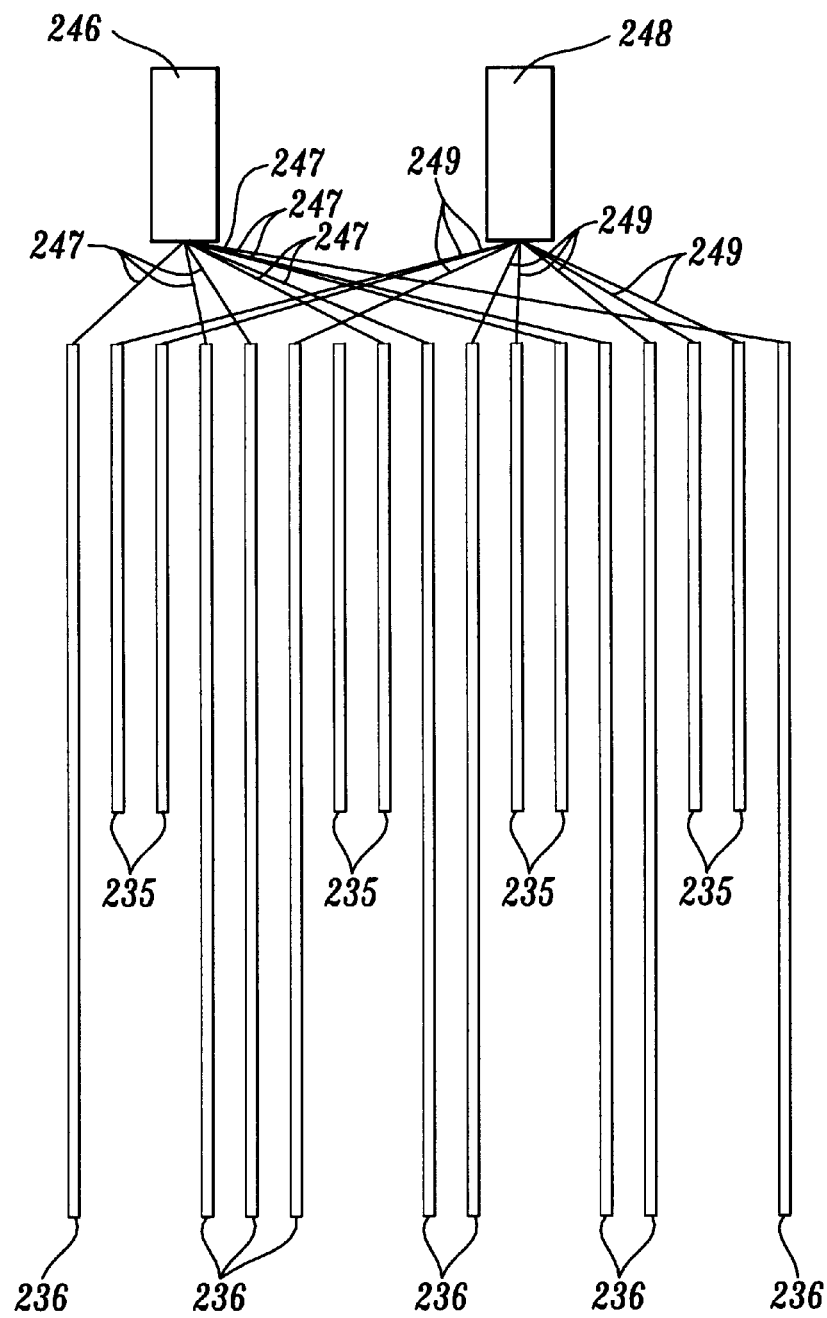
FIG. 25 is a view illustrating representative conduits for introducing absorbent material into a fibrous web in accordance with the present invention.

Plurality of conduits 235 can have an effective length different from plurality of conduits 236. The third material can be introduced through conduits 235 and 236, or, alternatively, a third material can be introduced through conduits 235 and a fourth material can be introduced through conduits 236. Preferably, the ends of conduits 235 and 236 terminate at a position beyond where the suction boxes begin withdrawing foam from the slurries in contact with the foraminous elements (i.e., beyond the point where web formation begins). Plurality of conduits 235 and/or 236 are suitable for introducing stripes or bands of third material in fibrous webs formed in accordance with the present invention. Plurality of conduits 235 and 236 can be moved in a first dimension toward and away from nip 213, and also in a second dimension substantially perpendicular to the first, closer to one forming wire or the other. Representative plurality of conduits 235 and 236 are illustrated in FIG. 25.

Generally, the former's interior structure (i.e., structure 230 in FIGS. 23 and 24) is positioned with respect to the foraminous elements such that material introduced through the interior structure will not directly contact the first and second foraminous elements. Accordingly, material is introduced through the interior structure between the first and second slurries after the slurries have contacted the foraminous elements and withdrawal of foam and liquid from those slurries has commenced. Such a configuration is particularly advantageous for introducing superabsorbent materials and for forming stratified structures in which the third material is a foam/fiber slurry. Depending upon the nature of the composite to be formed, the first and second fiber slurries may be the same, or different, from each other and from the third material.

In a preferred embodiment, the method includes introducing the third material at a plurality of different points. The positions of at least some of the plurality of different points for introducing the third material into the headbox can be adjusted when it is desired to adjust the introduction point in a first dimension toward and away from the headbox exit (i.e., nip 213 in FIGS. 23 and 24); and to adjust at least some of the plurality of points in a second dimension substantially perpendicular to the first dimension, closer to one forming wire or the other.

The method can also include utilizing a plurality of distinct conduits, the conduits being of at least two different lengths, for introducing the third material into the headbox. The method can also be utilized in headboxes having dividing walls that extend part of the length of the conduits toward the headbox exit. Such headboxes are illustrated in FIGS. 22 and 24.

The means for introducing first and second slurries into the first and second volumes can include any conventional type of conduit, nozzle, orifice, header, or the like. Typically, these means include a plurality of conduits are provided disposed on the first end of the former and facing the second end.

The means for withdrawing liquid and foam from the first and second slurries through the foraminous elements to form a web on the foraminous elements are also included in the headbox assembly. The means for withdrawing liquid and foam can include any conventional means for that purpose, such as suction rollers, pressing rollers, or other conventional structures. In a preferred embodiment, first and second suction box assemblies are provided and mounted on the opposite sides of the interior structure from the foraminous elements (see boxes 206 and 208 in FIGS. 22, 23, and 24).

In another embodiment, the composite of the invention includes one or more fibrous bands in a fibrous base. The base includes a fibrous matrix and absorbent material. Suitable fibrous bases are as described above. The fibrous bands are substantially free of absorbent material. In one embodiment, the fibrous band or bands extend along the machine direction of the composite. The number of bands in a particular composite is not particularly critical, and will depend upon the nature of the absorbent article into which the composite is incorporated. In one embodiment, the composite includes two fibrous bands, and in other embodiments, the composite includes more than two bands, for example, from three to about six bands.

Figure 31:
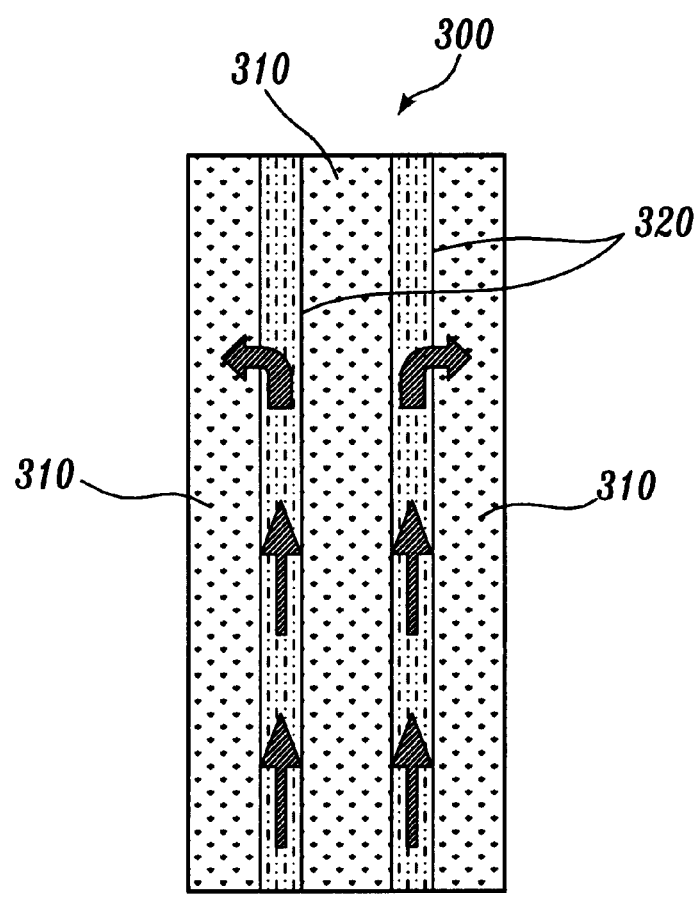
FIG. 31 is a schematic illustration of a representative composite having fibrous bands formed in accordance with the present invention.

A representative composite of the invention having two fibrous bands is illustrated schematically in FIG. 31. Referring to FIG. 31, composite 300 includes base matrix 310 and fibrous bands 320. For embodiments of the composite in which the base matrix includes absorbent material, the fibrous bands conduct fluid along the composite's length distributing fluid throughout the composite and to absorbent material in the base matrix where the fluid is ultimately stored. In the FIG. 31, fluid movement is indicated by the arrows.

Representative composites having fibrous bands and their performance characteristics are described in Examples 18, 19, and 21. A representative composite having two fibrous bands is described in Example 19. For this composite, wicking height at 15 minutes, capacity at 15 cm, and wetted zone capacity for representative composites are presented graphically in FIG. 32. Representative foam-formed composites having two fibrous bands are described in Example 21. For these composites, ring crush and tensile strength for are correlated graphically in FIG. 33; unrestrained vertical wicking height and saturation capacity are correlated graphically in FIG. 34; ring crush and tensile strength are compared graphically in FIG. 35; and unrestrained vertical wicking height and saturation capacity are compared graphically in FIG. 36.

The fibrous bands can include any of the fibrous materials described above including blends of fibers. For example, the fibrous band can include matrix fibers, resilient fibers, and blends of matrix and resilient fibers. In certain embodiments, the fibrous band includes crosslinked cellulosic fibers and/or matrix fibers. The fibrous band can include crosslinked fibers in an amount from about 15 percent to about 90 percent by weight based on the total weight of fibers in the band. In one embodiment, the fibrous band includes crosslinked fibers in an amount from about 20 percent to about 80 percent by weight based on the total weight of fibers in the band. In another embodiment, the fibrous band includes crosslinked fibers in an amount from about 40 percent to about 60 percent by weight based on the total weight of fibers in the band. The fibrous band can include matrix fibers in an amount from about 10 percent to about 85 percent by weight based on the total weight of fibers in the band. In one embodiment, the fibrous band includes matrix fibers in an amount from about 20 percent to about 80 percent by weight based on the total weight of fibers in the band. In another embodiment, the fibrous band includes matrix fibers in an amount from about 40 percent to about 60 percent by weight based on the total weight of fibers in the band.

As noted above, in one embodiment, the fibrous band includes a blend of crosslinked and matrix fibers. In one embodiment, the weight ratio of matrix fibers to crosslinked cellulosic fibers is about 1:1, in another embodiment the ratio is about 1:4, and in another embodiment the ratio is about 4:1.

The absorbent composite having fibrous bands offers advantages over other composites that lack fibrous bands. Among other advantages, the fibrous band or bands act as liquid distribution paths or channels within the composite's fibrous matrix that includes absorbent material. Thus, liquid acquired by the composite is rapidly distributed along the fibrous band and is absorbed out of these bands and into the surrounding fibrous matrix where the liquid is ultimately absorbed and retained by absorbent material. The composites including fibrous bands offer advantages associated with liquid wicking, total liquid absorbed, the rate of liquid uptake, and liquid flux, among other advantageous properties. For example, as described below, a representative absorbent composite having fibrous bands has an unrestrained vertical wicking height at 30 minutes of at least about 10 cm and, preferably, at least about 12 cm. The composite also has an unrestrained vertical wicking total fluid absorbed value at 30 minutes of at least about 30 g and, preferably, at least about 40 g. The composite also has an unrestrained vertical wicking uptake rate at 12 cm of at least about 1.0 g/g/min and, preferably, at least about 2.0 g/g/min. The composite also has an unrestrained vertical wicking flux at 12 cm of at least about $2.0/g/cm^2/min$ and, preferably, at least about $3.0 g/cm^2/min$.

The composite having fibrous bands also provides strength and softness advantages. Fibrous bands running the length of a composite will generally increase the softness of the composite across its width.

Fibrous bands also offer advantages related to composite processing. For example, the relatively porous fibrous band increases composite drying efficiency. Also, fibrous bands can impart breathability to the composite when utilized in an absorbent article.

Although the composite has been described as having bands of fibrous material, it will be appreciated that other configurations of fiber-only regions are within the scope of the invention. Representative configurations include circular, annular, ring, star, cross, and rectangular shapes, among others. The width of the band or other configuration can also be varied to suit a particular need. Wide bands have greater capacity than thin bands. The band or other configuration can also be tapered to facilitate, for example, fluid movement. In addition to having a tapered or changing length or width, the band or other configuration can also have a tapered or changing thickness (i.e., in direction of composite thickness).

The fibrous band can also be located in the fibrous base in various positions (e.g., variation in composite length, width, and thickness) to provide composites having a variety of fluid movement properties.

The absorbent composite having fibrous bands can be formed by wetlaid and foam-forming methods described above. The fibrous bands can be incorporated into the fibrous matrix to provide the composite by the methods described above. Fibrous bands can be formed by introducing fibers as the third (or fourth) material in the above-described method. Blends of fibers can also be introduced as the third material. In such forming methods, absorbent material can be introduced into the composite through other conduits, for example, as the fourth (or third) material, as described above.

The absorbent composite formed in accordance with the present invention can be incorporated as an absorbent core or storage layer into an absorbent article such as a diaper. The composite can be used alone or combined with one or more other layers, such as acquisition and/or distribution layers, to provide useful absorbent constructs as illustrated herein. In the figures illustrating constructs and articles, reference numeral 10 refers to all of the embodiments of the composites of the invention.

Figure 26A:
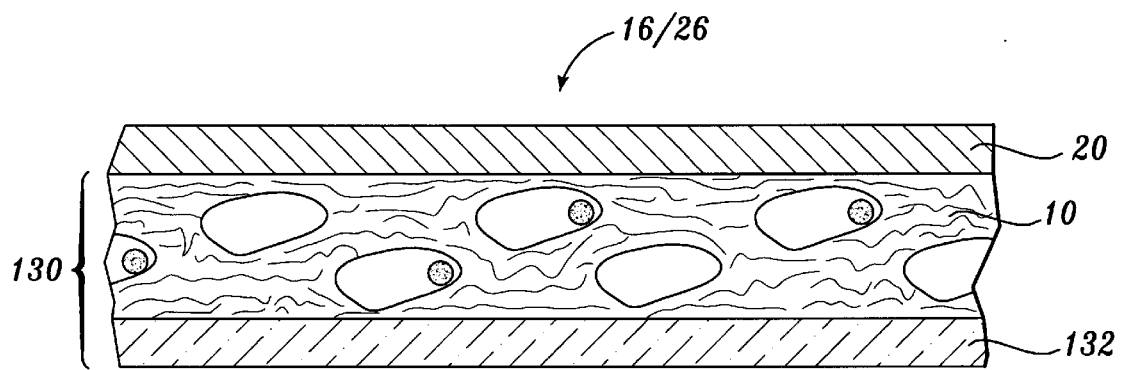
FIGS. 26A–C are cross-sectional views of portions of absorbent constructs incorporating an acquisition layer and a reticulated absorbent composite formed in accordance with the present invention.
Figure 26B:
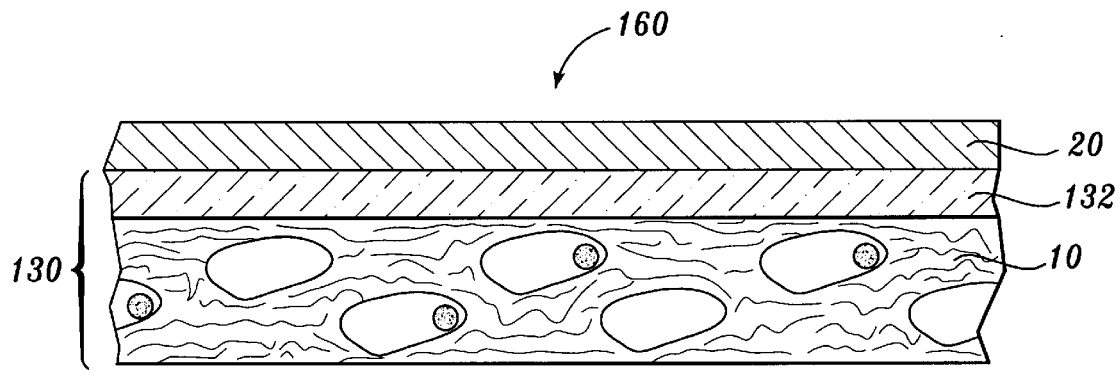
Figure 26C:
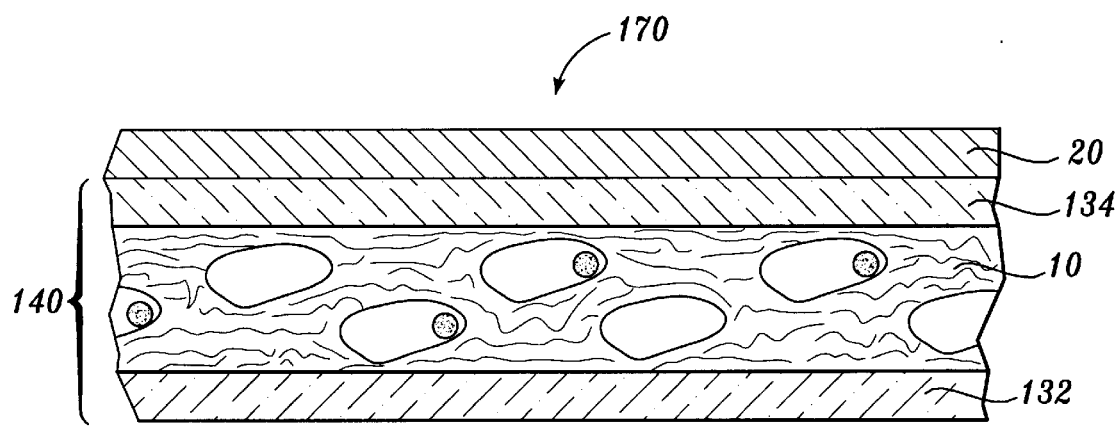

Representative absorbent constructs incorporating the absorbent composite having a reticulated core and fibrous strata are shown in FIGS. 26A–C and 27A–C. Referring to FIG. 26A, construct 150 includes composite 130 (i.e., reticulated core 10 and stratum 132) employed as a storage layer in combination with an upper acquisition layer 20. FIG. 26B illustrates construct 160, which includes composite 130 and acquisition layer 20 with stratum 132 adjacent acquisition layer 20. Construct 170, including acquisition layer 20 and composite 140, is illustrated in FIG. 26C.

Figure 27A:
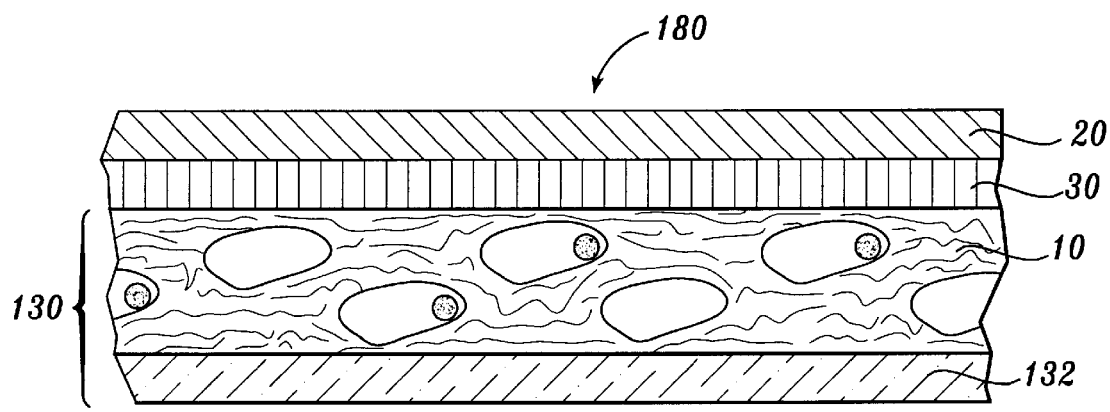
FIGS. 27A–C are cross-sectional views of portions of absorbent constructs incorporating an acquisition layer, intermediate layer, and a reticulated absorbent composite formed in accordance with the present invention.
Figure 27B:
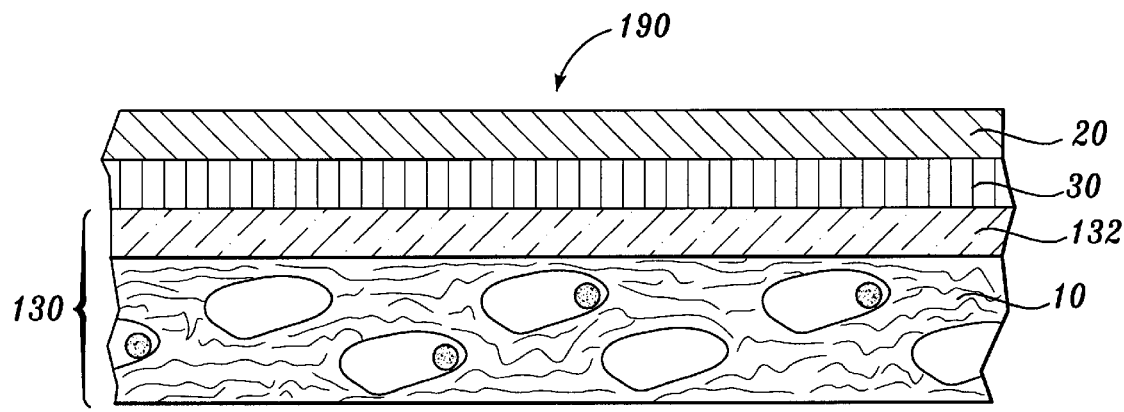
Figure 27C:
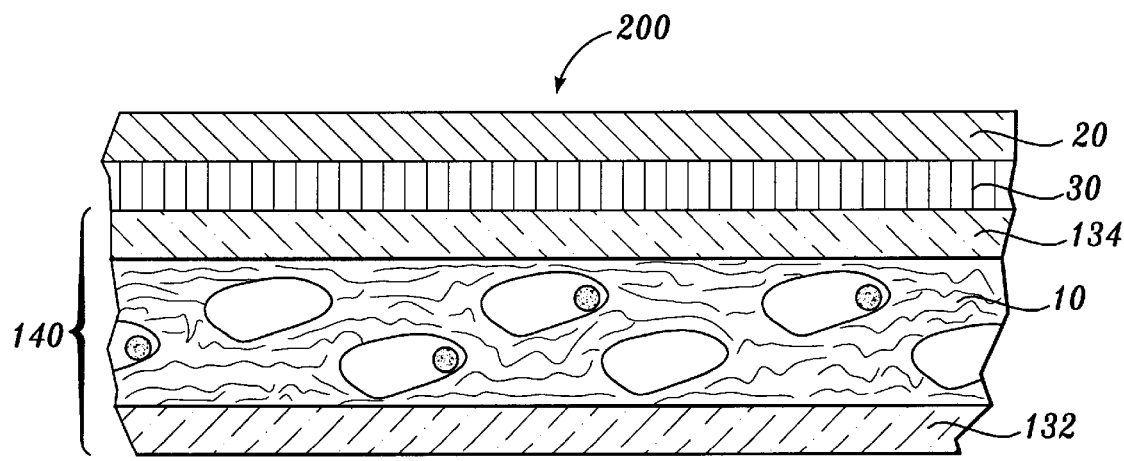

In addition to the constructs noted above that include the combination of absorbent composite and acquisition layer, further constructs can include a distribution layer intermediate the acquisition layer and composite. FIG. 27A illustrates construct 180 having intermediate layer 30 (e.g., distribution layer) interposed between acquisition layer 20 and composite 130. Similarly, FIGS. 27B and 23C illustrate constructs 190 and 200 having layer 30 intermediate acquisition layer 20 and composites 130 and 140, respectively.

Figure 28A:
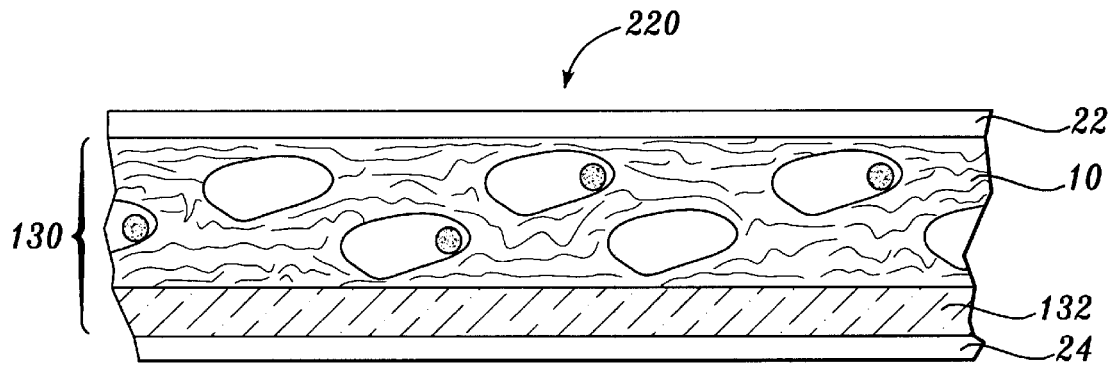
FIGS. 28A–C are cross-sectional views of portions of absorbent articles incorporating a reticulated absorbent composite formed in accordance with the present invention.
Figure 28B:
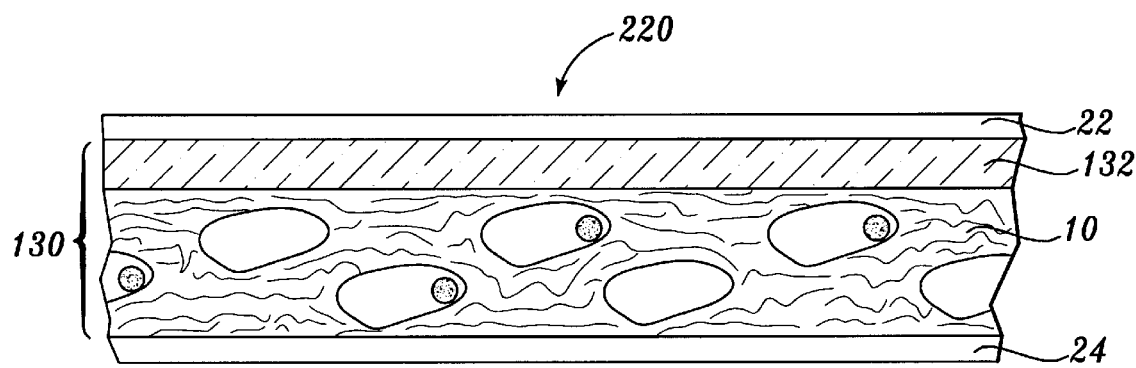
Figure 28C:
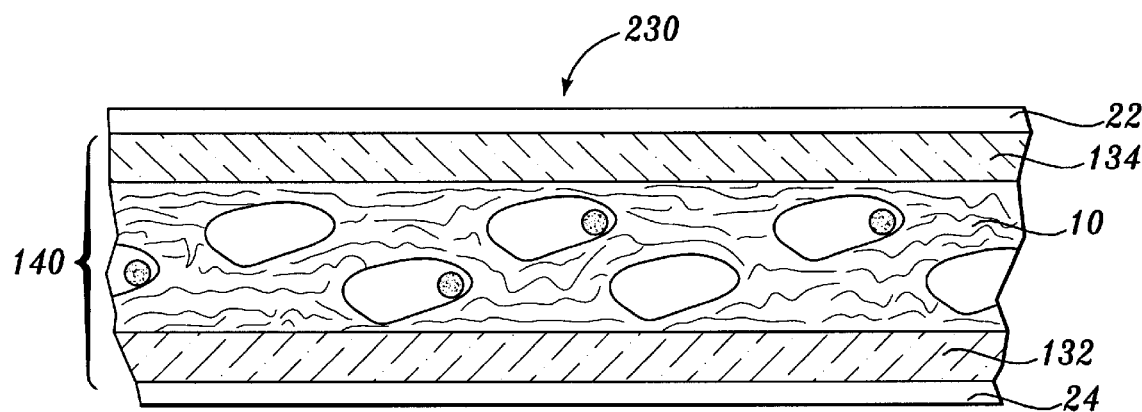
Figure 29A:
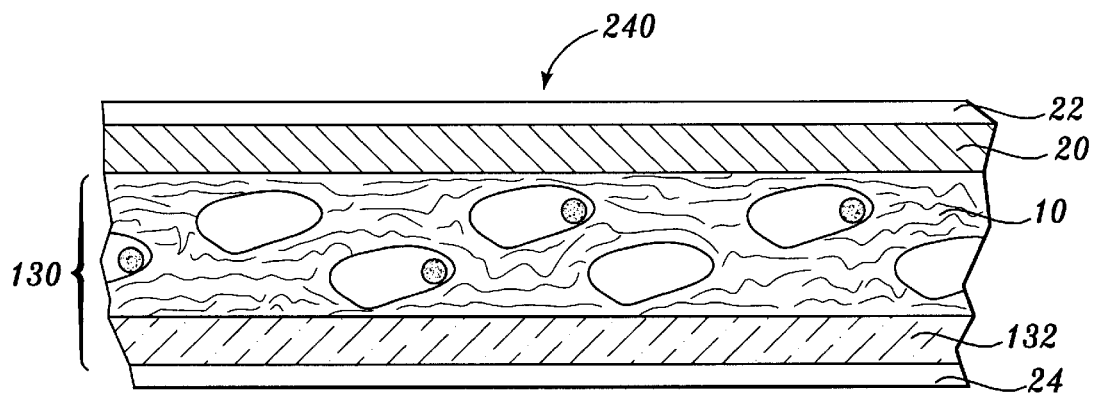
FIGS. 29A–C are cross-sectional views of portions of absorbent articles incorporating an acquisition layer and a reticulated absorbent composite formed in accordance with the present invention.
Figure 29B:
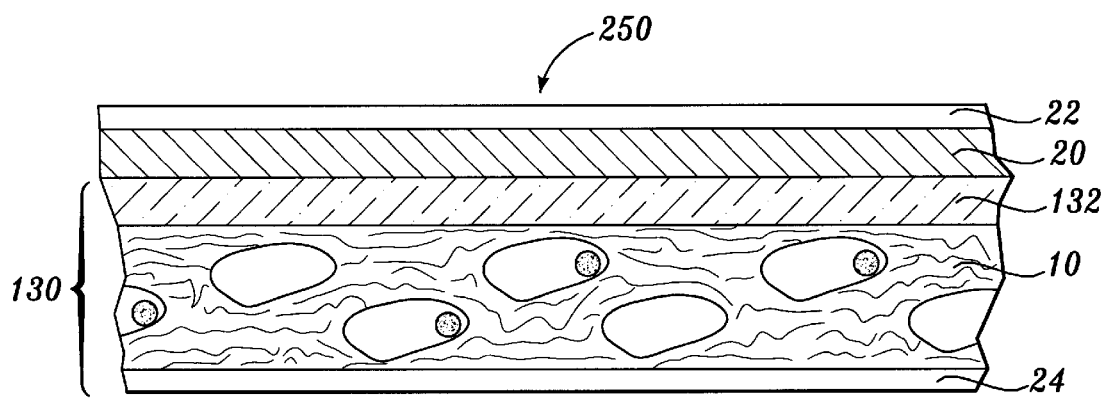
Figure 29C:
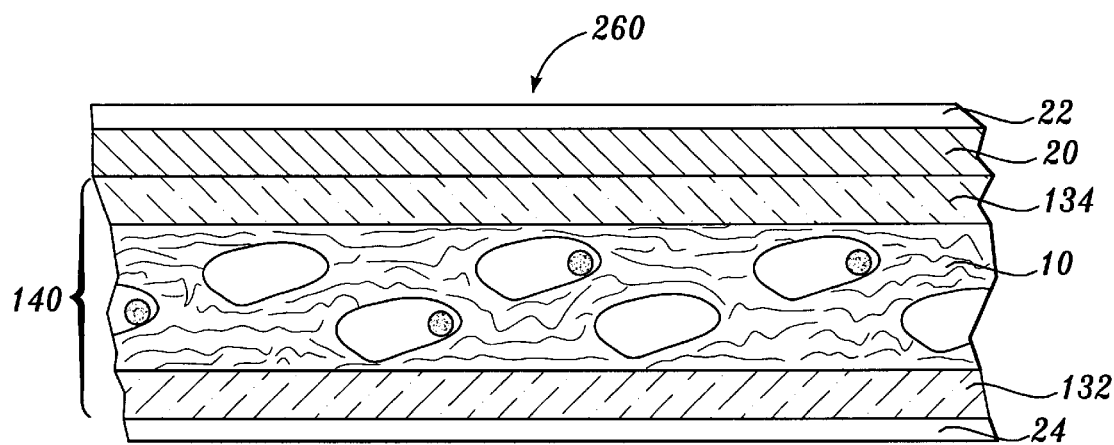
Figure 30A:
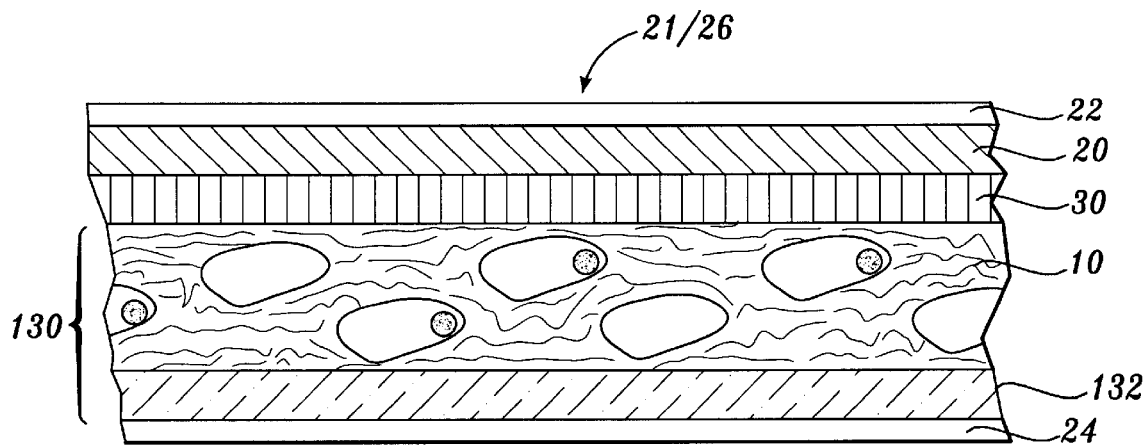
FIGS. 30A–C are cross-sectional views of portions of absorbent articles incorporating an acquisition layer, intermediate layer, and a reticulated absorbent composite formed in accordance with the present invention.
Figure 30B:
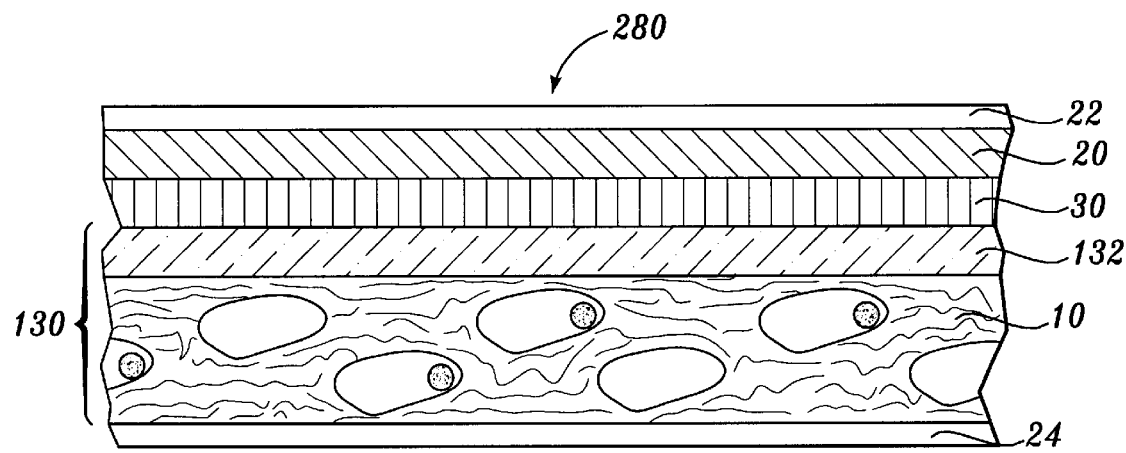
Figure 30C:
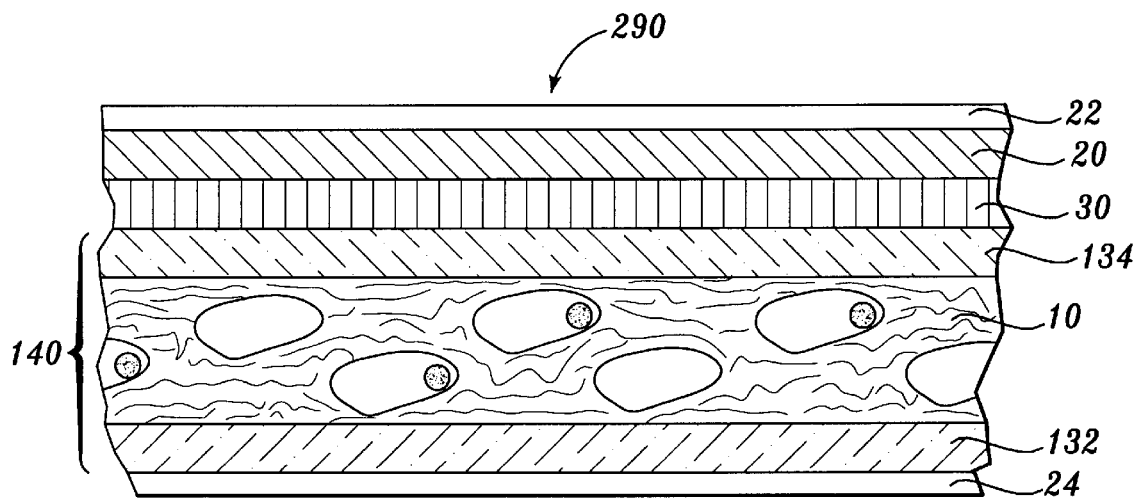

Composites 130 and 140 and constructs 150, 160, 170, 180, 190, and 200 can be incorporated into absorbent articles. Generally, absorbent articles 210, 220, and 230 shown in FIGS. 28A–C, respectively; absorbent articles 240, 250, and 260 shown in FIGS. 29A–C, respectively; and absorbent articles 270, 280, and 290 shown in FIGS. 30A–C, respectively, include liquid pervious facing sheet 22, liquid impervious backing sheet 24, and composites 130, 140, and constructs 150, 160, 170, 180, 190, and 200, respectively. In such absorbent articles, the facing sheet is joined to the backing sheet.

The following examples are provided for the purposes of illustration, and not imitation.

EXAMPLES

Example 1

Reticulated Absorbent Composite Formation: Representative Wet-laid Method

This example illustrates a wet-laid method for forming a representative absorbent composite.

A wet-laid composite formed in accordance with the present invention is prepared utilizing standard wet-laid apparatus known to those in the art. A slurry of a mixture of standard wood pulp fibers and crosslinked pulp fibers (48 and 12 percent by weight, respectively, based on total weight of dried composite) in water having a consistency of about 0.25 to 3 percent is formed. Consistency is defined as the weight percent of fibers present in the slurry, based on the total weight of the slurry. A wet strength agent such as Kymene® (0.5 percent based on total composite weight) is then added to the fibrous mixture. Finally, absorbent material (40 percent by weight based on total weight of dried composite) is added to the slurry, the slurry is thoroughly mixed, and then distributed onto a wire mesh to form a wet composite. The wet composite is dried to a moisture content of about 9 to about 15 weight percent based on total composite weight to form a representative reticulated absorbent composite.

Absorbent composites having a variety of basis weights can be prepared from the composite formed as described above by pre- or post-drying densification methods known to those in the art.

Example 2

Reticulated Absorbent Composite Formation: Representative Foam Method

This example illustrates a foam method for forming a representative absorbent composite.

A lab-size Waring blender is filled with 4 L of water and pulp fibers are added. The mixture is blended for a short time. Crosslinked cellulose fibers are then added to the pulp fibers and blended for at least one minute to open the crosslinked fibers and effect mixing of the two fibers. The resulting mixture may contain from 0.07 to 12 percent by weight of solids.

The mixture is placed in a container and blended for a few seconds with an air-entrapping blade. A surfactant (Incronan 30, Croda, Inc.) is added to the blended mixture. Approximately 1 g of active surfactant solids per gram of fiber is added. The mixture is blended while slowly raising the mixer blade height from the rising foam. After about one minute, the mixing is terminated, superabsorbent is added, and the mixing is restarted for another one-half minute at constant mixer blade height. The resulting foam-fiber mixture will have a volume about three times the volume of the original mixture.

The mixture is rapidly poured into a sheet mold having an inclined diffusion plate. After the addition of the mixture, the plate is removed from the mold, and a strong vacuum is applied to reduce the foam-fiber height. After most of the visible foam disappears, the vacuum is discontinued and the resulting sheet removed from the mold and passed, along with a forming wire, over a slit couch to remove excess foam and water.

The sheet is then dried in a drying oven to remove the moisture.

Example 3

Acquisition Times for a Representative Reticulated Absorbent Composite

In this example, the acquisition time for a representative reticulated absorbent composite formed in accordance with the present invention (Composite A) is compared to a commercially available diaper (Diaper A, Kimberly-Clark).

The tests were conducted on commercially available diapers (Kimberly-Clark) from which the core and surge management layer were removed and the surrounds used. The test diapers were prepared by inserting the absorbent composite into the diaper.

The aqueous solution used in the tests is a synthetic urine available from National Scientific under the trade name RICCA. The synthetic urine is a saline solution containing 135 meq./L sodium, 8.6 meq./L calcium, 7.7 meq./L magnesium, 1.94% urea by weight (based on total weight), plus other ingredients.

A sample of the absorbent structure was prepared for the test by determining the center of the structure's core, measuring 1 inch to the front for liquid application location, and marking the location with an "X". Once the sample was prepared, the test was conducted by first placing the sample on a plastic base (4¾ inch×19¼ inch) and then placing a funnel acquisition plate (4 inch×4 inch plastic plate) on top of the sample with the plate's hole positioned over the "X". A donut weight (1400 g) was then placed on top of the funnel acquisition plate to which was then attached a funnel (4 inch diameter). Liquid acquisition was then determined by pouring 100 mL synthetic urine into the funnel and measuring the time from when liquid was first introduced into the funnel to the time that liquid disappeared from the bottom of the funnel into the sample. The measured time is the acquisition time for the first liquid insult. After waiting one minute, a second 100 mL portion was added to the funnel and the acquisition time for the second insult was measured. After waiting an additional one minute, the acquisition was repeated for a third time to provide an acquisition time for the third insult. The acquisition times reported in seconds for each of the three successive 100 mL liquid insults for Diaper A and Composite A are summarized in Table 1.

TABLE 1

Acquisition Time Comparison

| | Acquisition Time (sec) | |
|---|---|---|
| Insult | Diaper A | Composite A |
| 1 | 45 | 10 |
| 2 | 60 | 11 |
| 3 | 75 | 10 |

As shown in Table 1, liquid is more rapidly acquired by the absorbent composite than for the commercially available diaper containing an air-laid storage core. The results show that the air-laid core does not acquire liquid nearly as rapidly as the reticulated composite. The commercial diaper also exhibited characteristic diminution of acquisition rate on successive liquid insults. In contrast, the composite formed in accordance with the invention maintained a relatively constant acquisition time as the composite continued to absorb liquid on successive insult. Significantly, the absorbent composite exhibits an acquisition time for the third insult that is substantially less (about fourfold) than that of the commercially available diaper for initial insult. The results reflect the greater wicking ability and capillary network for the wet-laid composite compared to a conventional air-laid storage core in general, and the enhanced performance of the reticulated absorbent composite in particular.

Example 4

Acquisition Rate and Rewet for Representative Reticulated Absorbent Composites

In this example, the acquisition time and rewet of representative reticulated absorbent composites formed in accordance with the present invention (designated Composites A1–A4) are compared to a commercially available diaper (Diaper A, Kimberly-Clark). Composites A1–A4 differ by the method by which the composites were dried.

Certain properties of the tested composites, including the amount of superabsorbent material (weight percent SAP) in the composite and basis weight for each of the composites, are summarized in Table 2.

The tests were conducted on commercially available diapers (Kimberly-Clark) from which the cores were removed and used as surrounds. The test diapers were prepared by inserting the tested composites into the diapers.

The acquisition time and rewet are determined in accordance with the multiple-dose rewet test described below.

Briefly, the multiple-dose rewet test measures the amount of synthetic urine released from an absorbent structure after each of three liquid applications, and the time required for each of the three liquid doses to wick into the product.

The aqueous solution used in the tests was a synthetic urine available from National Scientific under the trade name RICCA, and as described above in Example 1.

A preweighed sample of the absorbent structure was prepared for the test by determining the center of the structure's core, measuring 1 inch to the front for liquid application location, and marking the location with an "X". A liquid application funnel (minimum 100 mL capacity, 5–7 mL/s flow rate) was placed 4 inches above the surface of the sample at the "X". Once the sample was prepared, the test was conducted as follows. The sample was flattened, nonwoven side up, onto a tabletop under the liquid application funnel. The funnel was filled with a dose (100 mL) of synthetic urine. A dosing ring ($5/32$ inch stainless steel, 2 inch ID×3 inch height) was placed onto the "X" marked on the samples. A first dose of synthetic urine was applied within the dosing ring. Using a stopwatch, the liquid acquisition time was recorded in seconds from the time the funnel valve was opened until the liquid wicked into the product from the bottom of the dosing ring. After a twenty-minute wait period, rewet was determined. During the twenty-minute wait period after the first dose was applied, a stack of filter papers (19–22 g, Whatman #3, 11.0 cm or equivalent, that had been exposed to room humidity for minimum of 2 hours before testing) was weighed. The stack of preweighed filter papers was placed on the center of the wetted area. A cylindrical weight (8.9 cm diameter, 9.8 lb.) was placed on top of these filter papers. After two minutes the weight was removed, the filter papers were weighed and the weight change recorded. The procedure was repeated two more times. A second dose of synthetic urine was added to the diaper, and the acquisition time was determined, filter papers were placed on the sample for two minutes, and the weight change determined. For the second dose, the weight of the dry filter papers was 29–32 g, and for the third dose, the weight of the filter papers was 39–42 g. The dry papers from the prior dosage were supplemented with additional dry filter papers.

Liquid acquisition time is reported as the length of time (seconds) necessary for the liquid to be absorbed into the product for each of the three doses. The results are summarized in Table 2.

Rewet is reported as the amount of liquid (grams) absorbed back into the filter papers after each liquid dose (i.e., difference between the weight of wet filter papers and the weight of dry filter papers). The results are also summarized in Table 2.

TABLE 2

Acquisition Time and Rewet Comparison

| Composite | SAP % (w/w) | Basis Weight (gsm) | Acquisition Time (sec) | | | Rewet (g) | | |
|---|---|---|---|---|---|---|---|---|
| | | | Insult 1 | Insult 2 | Insult 3 | Insult 1 | Insult 2 | Insult 3 |
| A1 | 49.4 | 568 | 16 | 19 | 26 | 0.1 | 0.4 | 2.4 |
| A2 | 38.3 | 648 | 17 | 19 | 22 | 0.1 | 0.7 | 2.5 |

TABLE 2-continued

Acquisition Time and Rewet Comparison

| Composite | SAP % (w/w) | Basis Weight (gsm) | Acquisition Time (sec) | | | Rewet (g) | | |
|---|---|---|---|---|---|---|---|---|
| | | | Insult 1 | Insult 2 | Insult 3 | Insult 1 | Insult 2 | Insult 3 |
| A3 | 35.9 | 687 | 29 | 26 | 27 | 0.2 | 0.2 | 0.7 |
| A4 | 38.8 | 672 | 17 | 18 | 21 | 0.1 | 0.3 | 0.9 |
| Commercial air-laid core | 40.0 | 625 | 34 | 35 | 39 | 0.1 | 4.0 | 12.6 |

As indicated in Table 2, the acquisition times for representative composites formed in accordance with the invention (Composites A1–A4) were significantly less than for the commercially available core.

The rewet of the representative composites (Composites A1–A4) is significantly less than for the other cores. While the composites exhibited relatively low rewet initially, after the third insult the commercially available core showed substantial rewet. In contrast, Composites A continued to exhibit low rewet.

Example 5

Horizontal and Vertical Wicking for a Representative Reticulated Absorbent Composite In this example, the wicking characteristics of a representative reticulated absorbent composite (Composite A) are compared to a commercially available diaper storage core (Diaper B, Procter & Gamble).

The horizontal wicking test measures the time required for liquid to horizontally wick preselected distances. The test was performed by placing a sample composite on a horizontal surface with one end in contact with a liquid bath and measuring the time required for liquid to wick preselected distances. Briefly, a sample composite strip (40 cm×10 cm) was cut from a pulp sheet or other source. If the sheet has a machine direction, the cut was made such that the 40 cm length of the strip was parallel to the machine direction. Starting at one end of the 10 cm width of the strip, a first line was marked at 4.5 cm from the strip edge and then consecutive lines at 5 cm intervals were marked along the entire length of the strip (i.e., 0 cm, 5 cm, 10 cm, 15 cm, 20 cm, 25 cm, 30 cm, and 35 cm). A horizontal wicking apparatus having a center trough with level horizontal wings extending away from opposing sides of the trough was prepared. The nonsupported edge of each wing was positioned to be flush with the inside edge of the trough. On each wing's end was placed a plastic extension to support each wing in a level and horizontal position. The trough was then filled with synthetic urine. The sample composite strip was then gently bent at the 4.5 cm mark to form an approximately 45° angle in the strip. The strip was then placed on the wing such that the strip lay horizontally and the bent end of the strip extended into and contacted the liquid in the trough. Liquid wicking was timed beginning from when the liquid reached the first line marked on the composite 5 cm from the 4.5 cm bend. The wicking time was then recorded at 5 cm intervals when 50 percent of the liquid front reached the marked interval (e.g., 5 cm, 10 cm). The liquid level in the trough was maintained at a relatively constant level throughout the test by replenishing with additional synthetic urine. The horizontal wicking results are summarized in Table 3.

TABLE 3

Horizontal Wicking Comparison

| | Wicking Time (sec) | |
|---|---|---|
| Distance (cm) | Diaper B | Composite A |
| 5 | 48 | 15 |
| 10 | 150 | 52 |
| 15 | 290 | 134 |
| 20 | 458 | 285 |
| 25 | 783 | 540 |
| 30 | 1703 | 1117 |
| 35 | — | 1425 |

The results tabulated above indicate that horizontal wicking is enhanced for the absorbent composite formed in accordance with the invention compared to a conventional air-laid core. The wicking time for Composite A is about 50 percent of that for the conventional diaper core. Thus, the horizontal wicking for Composite A is about 1.5 to about 3 times that of a commercially available storage core.

The vertical wicking test measures the time required for liquid to vertically wick preselected distances. The test was performed by vertically suspending a sample composite with one end of the composite in contact with a liquid bath and measuring the time required for liquid to wick preselected distances. Prior to the test, sample composites (10 cm×22 cm) were cut and marked with consecutive lines 1 cm, 11 cm, 16 cm, and 21 cm from one of the strip's edges. Preferably, samples were preconditioned for 12 hours at 50 percent relative humidity and 23° C. and then stored in sample bags until testing. The sample composite was oriented lengthwise vertically and clamped from its top edge at the 1 cm mark, allowing its bottom edge to contact a bath containing synthetic urine. Timing was commenced once the strip was contacted with the liquid. The time required for 5 percent of the wicking front to reach 5 cm, 10 cm, 15 cm, and 20 cm was then recorded. The vertical wicking results are summarized in Table 4.

TABLE 4

Vertical Wicking Comparison

| | Wicking Time (sec) | |
|---|---|---|
| Distance (cm) | Diaper B | Composite A |
| 5 | 20 | 6 |
| 10 | Fell Apart | 54 |
| 15 | — | 513 |
| 20 | — | 3780 |

As for the horizontal wicking results, Composite A had significantly greater vertical wicking compared to the commercial core. The results also show that the composite formed in accordance with the invention has significantly greater wet tensile strength compared to the conventional air-laid composite.

Example 6

Liquid Distribution for a Representative Reticulated Absorbent Composite

In this example, the distribution of liquid in a reticulated absorbent composite (Composite A) is compared to that of two commercially available diapers (Diapers A and B above). The test measures the capacity of a diaper core to distribute acquired liquid. Perfect distribution would have 0% deviation from average. Ideal liquid distribution would result in equal distribution of the applied liquid in each of the four distribution zones (i.e., about 25% liquid in each zone).

Liquid distribution is determined by weighing different zones of a sample that has been subjected to the multiple-dose rewet test described above in Example 4. Basically, after the last rewet, the wings of the diaper are removed and then cut into four equal length distribution zones. Each zone is then weighed to determine the weight of liquid contained in each zone.

The liquid distribution results for a representative reticulated absorbent composite approach ideality. The results indicate that while the representative commercial storage cores accumulate liquid near the site of insult, liquid is efficiently and effectively distributed throughout the reticulated absorbent storage core.

Example 7

Wet and Dry Tensile Strength for a Reticulated Absorbent Composite

In this example, the measurement of wet and dry tensile strength of a representative absorbent composite is described.

A dry pad tensile integrity test is performed on a 4 inch by 4 inch square test pad by clamping a dry test pad along two opposing sides. About 3 inches of pad length is left visible between the clamps. The sample is pulled vertically in an Instron testing machine and the tensile strength measured is reported in N/m. The tensile strength is converted to tensile index, Nm/g, by dividing the tensile strength by the basis weight g/m².

A wet tensile integrity test is performed by taking a sample composite that has been immersed in synthetic urine for 10 minutes and then allowed to drain for 5 minutes and placing the sample in a horizontal jig. Opposite ends of the sample are clamped and then pulled horizontally on the Instron testing machine. The wet tensile strength, N/m, is converted to tensile index, Nm/g, by dividing the tensile strength by the basis weight g/m².

Typically, increasing the amount of Kymene® from 2 to 100 pounds per ton of fiber may increase the dry tensile strength from about 0.15 Nm/g to 0.66 Nm/g and the wet tensile from about 1.5 Nm/g to about 2.4 Nm/g.

Example 8

Taber Stiffness for Representative Reticulated Absorbent Composites

The stiffness of representative reticulated absorbent composites formed in accordance with the present invention was determined by the Taber Stiffness method. Representative composites were formed by wet-laid and foam methods. These composites included matrix fibers (48 percent by weight, southern pine commercially available from Weyerhaeuser Co. under the designation NB416), resilient fibers (12 percent by weights polymaleic acid crosslinked fibers), and absorbent material (40 percent by weight, superabsorbent material commercially available from Stockhausen). One of the wet-laid and one of the foam-formed composites further included a wet strength agent (about 0.5 percent by weight, polyamide-epichlorohydrin resin commercially available from Hercules under the designation Kymene®).

The stiffness of the foam-formed composites was significantly lower than the similarly constituted wet-laid composites. The results also indicate that, for the wet-laid composites, the inclusion of a wet strength agent increases the composite's stiffness.

Example 9

Reticulated Absorbent Composite Formation: Representative Wet-laid Method

This example illustrates a representative wet-laid method for forming a reticulated composite using a Rotoformer papermaking machine.

Briefly, slurries of absorbent material and fibers in water were introduced into the Rotoformer's headbox. The fibrous slurry was introduced to the headbox in the conventional manner. The absorbent slurry was introduced through the use of a dispersion unit consisting of a set of spargers. The spargers were fed from a header fed by the absorbent slurry supply. The dispersion unit is mounted on the Rotoformer headbox with the spargers inserted into the headbox fiber stock such that the flow of the absorbent slurry is against the fiber stock flow. Such a reversed flow for the absorbent slurry is believed to provide more effective mixing of the absorbent material and the fibers than would occur for absorbent material flow in the same direction as the fiber stock.

Absorbent material is introduced into the Rotoformer headbox as a slurry in water. One method that provides suitable results for introducing absorbent material into the headbox is a mixing system that includes a funnel attached directly to the inlet of a pump into which chilled water is fed at a controlled rate. The funnel receives water and dry absorbent material delivered from absorbent material supply by auger metering and forms a pond that contains absorbent material and water. The absorbent slurry is preferably pumped from the funnel to the headbox at approximately the same rate as water is delivered to the funnel. Such a system minimizes the exposure of the absorbent to the water. In practice, the absorbent slurry is delivered from the mixing system to the headbox through a 10 to 50 foot conduit in less than about 10 seconds.

In a typical formation run, fiber stock flow to the Rotoformer headbox was about 90 gpm (gallon/min) and absorbent slurry (1–2.6% solids) flow was about 10 gpm. Prior to initiation of fiber stock flow to the headbox and the introduction of absorbent slurry to the dispersion unit, water was flowed into the dispersion unit to the headbox to prevent fibers from plugging the spargers. Once the target basis weight of fiber was reached, the absorbent auger metering system was initiated and absorbent slurry was introduced into the headbox. For the runs made in accordance with the method described above, the target fiber basis weight was about 370 gsm (g/m²) and the production speed was about 10 fpm (ft/min). The relatively slow production speed was a consequence of the relatively limited drying capability of the machine's flatbed dryer.

The headbox contents including fibers and absorbent were deposited on a forming wire and dewatered to provide a wet composite. The wet composite was then dried to a moisture content of from about 9 to about 15 weight percent based on total composite weight to form a representative reticulated absorbent composite.

Absorbent composites having a variety of basis weights can be prepared from the composite formed as described above by pre- or post-drying densification methods known to those in the art.

Examples 10–15 illustrate the formation of representative reticulated absorbent composites using the method described above.

Example 10

A representative composite was formed as described in Example 9. The composite included about 60% by weight fibers and about 40% by weight absorbent material based on the total weight of composite. The fiber stock was a mixture of 80% by weight standard wood pulp fibers (once-dried southern pine commercially available from Weyerhaeuser Company under the designation FR416) and 20% weight crosslinked pulp fibers. The absorbent material was a crosslinked polyacrylate commercially available from Stockhausen under the designation SXM 77, which was screened using 300 micron mesh to eliminate fines prior to use. The composite also included about 25 pounds wet strength agent (a polyacrylamide-epichlorohydrin resin commercially available from Hercules under the designation Kymene® 557LX) per ton of fibers.

Target density of the absorbent composite was accomplished by calendering using a single nip with no applied load.

Performance data for the representative composite formed as described above (Composite B) is presented in Tables 5 and 6 in Example 16.

Example 11

A representative composite was formed as described in Example 10 except that the composite was calendered at 25 fpm.

Performance data for the representative composite formed as described above (Composite C) is presented in Tables 5 and 6 in Example 16.

Example 12

A representative composite was formed as described in Example 11 except that the amount of wet strength agent in the composite was reduced to 12.5 pounds per ton fiber and the standard wood pulp fibers were never-dried FR416 fibers.

Performance data for the representative composite formed as described above (Composite D) is presented in Tables 5 and 6 in Example 16.

Example 13

A representative composite was formed as described in Example 12 except that the composite was not densified.

Performance data for the representative composite formed as described above (Composite E) is presented in Tables 5 and 6 in Example 16.

Example 14

A representative composite was formed as described in Example 12 except that the wood pulp fibers were once-dried FR416 fibers.

Performance data for the representative composite formed as described above (Composite F) is presented in Tables 5 and 6 in Example 16.

Example 15

A representative composite was formed as described in Example 12 except that the amount of fibers in the composite was increased to about 80% by weight and the amount of absorbent present in the composite was decreased to about 20% by weight of the total composite.

Performance data for the representative composite formed as described above (Composite G) is presented in Tables 5 and 6 in Example 16.

Example 16

The performance of representative composites (Composites B–D) prepared as described in Examples 10–15 is summarized in Tables 5 and 6. The liquid wicking, absorbent capacity, wet and dry tensile strength, and wet strength of the representative composites are compared to a conventional handsheet in Table 5. The conventional handsheet had a basis weight and density comparable to the representative composites and included 60 percent by weight fibers (25 percent crosslinked fibers and 75 percent standard wood pulp fibers), 40 percent by weight superabsorbent material, and 12.5 pounds Kymene per ton fibers. The results presented in Table 5 are the average of three measurements except for the tensile values, which average four measurements. In the table, "MD" refers to the composites' machine direction and "CD" refers to the cross-machine direction. The wicking values were obtained by the methods described in Example 5 and the wet and dry tensile values were obtained by the method described in Example 7. The wet strength value was calculated and is defined as the ratio of wet tensile to dry tensile values. The mass flow rate value (g/min/g) was determined by measuring the weight gain of a portion of a composite (22 cm×5 cm) divided by the lesser of the time required for the liquid to wick 15 cm or 15 minutes, divided by the weight of the original sample.

TABLE 5

Performance Characteristics

| Composite | Wicking | | | | | | Wet Tensile | | Dry Tensile | | Wet Strength | |
|---|---|---|---|---|---|---|---|---|---|---|---|---|
| | Time to 10 cm (sec) | Time to 15 cm (sec) | Final Wick (cm) (45 min max) | 5 Min. (Vert.) Cap. (g/g) | Mass Flow Rate (g/min/g) | Capacity 15 Minute Free Swell Cap. (g/g) | MD (g/in) | CD (g/in) | MD (g/in) | CD (g/in) | MD (%) | CD (%) |
| B | 45 | 234 | 23 | 7.6 | 1.9 | 20 | 1585 | 1222 | >4800 | 4385 | <32 | 28 |
| C | 47 | 221 | 24 | 8.3 | 2.3 | 19 | 1317 | 1241 | >4800 | 4277 | <27 | 29 |
| D | 59 | >400 | 18 | 9.3 | <1.4 | 24 | 673 | 488 | 2940 | 2455 | 23 | 20 |
| E | 160 | >400 | 19 | 9.4 | <1.4 | 22 | 1091 | 764 | >4800 | 3771 | <23 | 20 |
| F | 38 | 144 | 25 | 7.7 | 3.2 | 15 | 1654 | 1291 | >5200 | 5100 | <31 | <25 |
| G | 52 | 245 | 22 | 8.4 | 2.1 | 20 | 1686 | 980 | >5200 | 4800 | <32 | <21 |
| handsheet | 159 | >300 | 16 | 10.9 | 2.2 | 31 | 226 | | | | | |

The absorbent capacity of several of the representative composites is summarized in Table 6. In this capacity test, portions of the representative composites (i.e., 10 cm squares) were immersed in a 1% saline solution. The samples were allowed to absorb liquid and swell for 10 minutes. The difference in the weight of the composite before and after the 10 minute swell is the capacity that is reported as cc/g.

TABLE 6

Absorbent capacity

| Composite | Capacity (cc/g) |
|---|---|
| B | 16.9 |
| C | 16.9 |
| D | 20.4 |
| E | 21.5 |

Example 17

Method for Determining Fluid Wicking for Representative Composites

The absorbent properties of representative composites can be determined by measuring unrestrained vertical wicking height, which is indicative of the composite's ability to wick and distribute fluid.

Unrestrained vertical wicking height at 15 minutes was measured for representative composites as described below.

Material:
Synthetic urine for wicking—"Blood Bank" 0.9% Saline Solution

Samples:
Size: 6.5 cm(CD)×25 cm(MD), marked with both permanent and water permeable lines at 1, 11, 16, and 21 cm along MD.

Method:
1) Perform % Solids on sample material and record.
2) Cut Sample and record (as is) weight and dry caliper.
3) Clamp sample at 1 cm from top.
4) Dip into liquid up to the 1 cm line.
5) Immediately start timing.
6) At the end of 5, 10, and 15 minutes, record the Wicking Height by measuring down from the next highest line. Report the wicking height to the nearest 0.5 cm.
7) At 15 minutes raise sample out of fluid and while still clamped, cut sample at the 1 cm and 15 cm height lines. Discard the 1 cm section.
8) Weigh wet 15 cm long sample and record.
9) Unclamp remaining sample and add to balance in order to record entire pad wet weight.
10) Report Total Wick Height at 15 minutes.
11) Report As-is and O.D. basis Entire Pad Capacity(g/g) by calculating:

$$\text{Entire Pad Capacity(g/g)} = \frac{\text{Wet Wt.} - (\text{As Is or } O.D. \text{ Wt.}) *}{\text{As-Is or } O.D. \text{ Wt.} *}$$

15) Calculate the Wicked Pad Capacity if needed:

$$\text{Wicked Pad Capacity} = \text{Entire Pad Capacity} \times \frac{24}{\text{Wicking Ht at 15 min}}$$

Unrestrained vertical wicking height for representative composites is described in the following examples.

Example 18

Performance Characteristics of Representative Composites Having Fibrous Bands The performance characteristics of representative composites prepared as described above are summarized in Table 7. The unrestrained vertical wicking height and total fluid absorbed at 30 minutes and the uptake rate and flux at 12 cm are compared for composites formed in accordance with the present invention and for commercially available air-laid cores. In Table 7, Composite I is a reticulated absorbent composite formed in accordance with the present invention having a composition that includes about 58% by weight absorbent material, 32% by weight crosslinked fibers, and 8% by weight matrix fibers based on the total weight of the composition. Composites J and K are composites that include two fibrous bands. For these composites, the fibrous matrix included 69% by weight absorbent material, 24% by weight crosslinked fibers, and 6% by weight matrix fibers based on the total weight of the matrix. Composite J had fibrous bands composed of crosslinked and matrix fibers in which the ratio of crosslinked to matrix fibers was 1:4.

Composite K had a crosslinked to matrix fiber ratio of 1:1.

TABLE 7

Representative Composite Unrestrained Vertical Wicking Parameters

| | Unrestrained Vertical Wicking | | | |
|---|---|---|---|---|
| Composite | Height (cm) | Total Fluid Absorbed (g) | Uptake Rate (g/g/min) | Flux (g/cm$^2$/min) |
| I | 12.3 | 47.2 | 1.0 | 2.2 |
| J | 15.5 | 49.0 | 2.5 | 5.7 |
| K | 15.6 | 52.0 | 3.0 | 5.8 |
| Airlaid core | 7.5* | 27.5* | — | — |

*integrity loss after 6 min.

As shown in Table 7, composites formed in accordance with the present invention vastly outperformed the commercially available airlaid core. Composites J and K, which included fibrous bands, had liquid wicking and distribution characteristics that were enhanced compared to Composite I, a composite lacking the fibrous bands.

Example 19

Performance Characteristics of a Representative Composite Having Two Fibrous Bands The performance characteristics for a representative composite having two fibrous bands (Composite L) were compared to a similarly constituted composite lacking fibrous bands (Control). The control composite had a basis weight of 700 gsm and included 50 percent by weight superabsorbent material; 25 percent by weight crosslinked cellulosic fibers; 25 percent by weight fluff pulp fibers (refined southern pine) based on the total weight of the composite. The composite having fibrous bands was constructed from the control composite and fibrous strips. The components were adhered together to provide the composite (see, for example, FIG. 31). The composite had a length of 25 cm, width 5 cm, and included two fibrous strips having a width of 0.75 cm.

Figure 32:
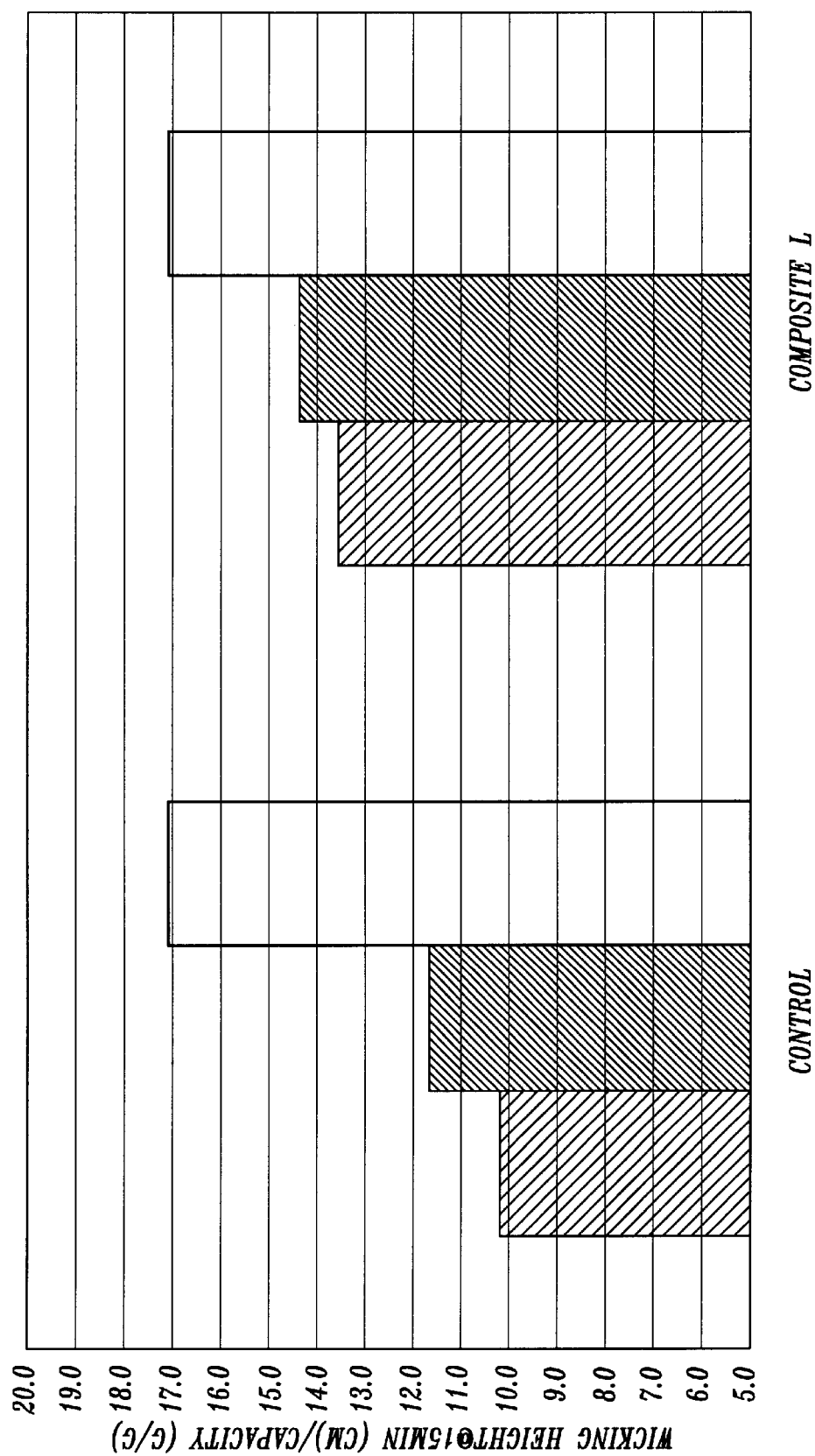
FIG. 32 is a graph comparing the wicking height at 15 minutes, capacity at 15 cm, and wetted zone capacity for representative composites formed in accordance with the present invention.

Wicking height at 15 minutes, capacity at 15 cm, and wetted zone capacity for the composites are compared graphically in FIG. 32. As shown in FIG. 32, wicking height and capacity at 15 minutes for the Composite L were increased relative to the control composite.

The properties and characteristics of Composite L and the control are summarized in Table 8.

TABLE 8

Unrestrained Vertical Wicking Performance.

| Composite | Basis Weight (gsm) | Density (g/cm$^3$) | Bulk (cm$^3$/g) | Total Fluid Wicked (g) | Wet Zone (g/g) cap OD | 15 cm g/g cap OD | Height at 15 min. |
|---|---|---|---|---|---|---|---|
| Control | 700 | 0.144 | 6.93 | 80.90 | 17.16 | 11.80 | 10.4 |
| L | 810 | 0.165 | 6.05 | 120.37 | 16.63 | 14.58 | 13.8 |

Example 20

Method for Determining Flexibility and Softness for Representative Composites

Composite flexibility and softness are factors for determining the suitability of composites for incorporation into personal care absorbent products. Composite flexibility can be indicated by composite edgewise ring crush, which is a measure of the force required to compress the composite as described below. For a composite to be incorporated into a personal care absorbent product, suitable ring crush values range from about 400 to about 1600 gram/inch. Composite softness can be indicated by a variety of parameters including composite edgewise compression. Edgewise compression (EC) is the force required to compress the composite corrected by the composite's basis weight as described below. For a composite to be suitably incorporated into a personal care absorbent product, the composite has a ring crush value in the range from about 400–1600 g and a basis weight in the range from about 250 to about 650 gsm.

The flexibility and softness of representative reticulated absorbent composites formed by wetlaid and foam-forming methods in accordance with the present invention were determined by measuring composite edgewise ring crush and edgewise compression.

The flexibility and softness of representative composites was determined by an edgewise ring crush method. In the method, a length of the composite (typically about 12 inches) is formed into a cylinder and its ends stapled together to provide cylinder having a height equal to the composite's width (typically about 2.5 inches). Edgewise ring crush is measured by adding mass to the top of the composite ring sufficient to reduce the composite cylinder's height by one-half. The more flexible the composite, the less weight required to reduce the height in the measurement. The edgewise ring crush is measured and reported as a mass (g). Edgewise compression (EC) is the ring crush reported in units of g/gsm in the tables below.

The following is a description of the ring crush method.
Samples: 6.35 cm (2.5 in)×30.5 cm (12 in)
Triplicate analysis (A, B, C)
Method:
1) Cut triplicate of sample size, lengthwise in the composite machine direction (MD).
2) Condition samples for 2 hours at 50% relative humidity or ambient conditions.
3) With the wire side on the outside, form the individual samples into loops so the two narrow ends meet without any overlap. Using four staples, attached the ends together at the top, bottom, and twice in the middle. The top and bottom staples should be 0.3–0.5 cm from the edge and the middle staples should be less than 2 cm from each other and the respective top or bottom staple. Finally, ensure that each staple penetrates fiber only areas.
4) Set the bottom platen on a smooth, level surface.
5) Place the sample, edgewise and in the center, between the top and bottom platens.
6) Gently place a 100-g weight on the center of the top platen (or 500-weight) and wait 3 seconds.
7) Then, gently stack 3 more 100-g weights at 3-second intervals.
8) If the ring collapses 50% or more of it's original height within a 3-second interval, then record the total amount of weight necessary to do so, i.e., add the weight of the top platen and the other combined weights.
9) If the combined weight doesn't crush the sample, then carefully remove the four 100-g weights.
10) Gently add a(nother) 500-g weight and weight 3 seconds.
11) If the ring collapses 50% or more of it's original height within a 3-second interval, then record the total amount of weight necessary to do so, i.e., add the weight of the top platen and weight(s).

12) Repeat step 6 through 11, increasing the number of 500-g weights by one for each cycle.

13) Repeat steps 5 through 11 for the other replicates.

14) Record the average weight for the replicates in g•f rounded to the nearest 10 g.

Calculations:

Average ring crush weight=(Weight A+Weight B+Weight C)/3

The ring crush values determined as described above for representative composites formed in accordance with the present invention are summarized in Example 21.

The softness of representative reticulated absorbent composites formed in accordance with the present invention can be indicated by edgewise compression. Edgewise compression is discussed in *The Handbook of Physical and Mechanical Testing of Paper and Paperboard*, Richard E. Mark, Dekker 1983 (Vol. 1). Edgewise compression was determined by correcting edgewise ring crush, determined as described above, for composite basis weight. The edgewise compression (EC) values for representative composites formed in accordance with the present invention are summarized in Example 21.

Example 21

Performance Characteristics of Representative Foam-Formed Composites Having Fibrous Bands The performance characteristics of representative foam-formed composites having fibrous bands (Composites M, N, O) were compared to similarly constituted foam-formed composites lacking fibrous bands (Control A and B). The composites were prepared on a twin-wire former as described above.

Fluff pulp fibers for the composites were unrefined softwood fibers (southern pine, 745 CSF), and refined fibers were refined softwood (southern pine, 200 CSF). The superabsorbent polymer was a lightly crosslinked polyacrylate (SR1001). All composites included a wet strength agent (KYMENE), 0.45 percent by weight based on the total weight of the composite.

Control A included 58 percent by weight superabsorbent material and 42 percent by weight fibrous material based on the total weight of the composite. The fibrous material included 67 percent by weight crosslinked fibers and 33 percent by weight fluff pulp fibers based on the total weight of fibers.

Control B included 50 percent by weight superabsorbent material and 50 percent by weight fibrous material based on the total weight of the composite. The fibrous material included 67 percent by weight crosslinked fibers and 33 percent by weight fluff pulp fibers based on the total weight of fibers. Control B further included the fibrous material making up the fibrous bands in Composites M, N, and O.

Composites M–O included two fibrous bands (50 gsm) in a fibrous base. The fibrous base included 50 percent by weight superabsorbent material and 50 percent by weight fibrous material based on the total weight of the composite. The fibrous material include 67 percent by weight crosslinked fibers and 33 percent by weight fluff pulp fibers based on the total weight of fibers.

For Composite M, the fibrous bands included 50 percent by weight crosslinked fibers and 50 percent by weight refined fibers based on the total weight of fibers in the bands.

For Composite N, the fibrous bands included 80 percent by weight crosslinked fibers and 20 percent by weight refined fibers based on the total weight of fibers in the bands.

For Composite O, the fibrous bands included 50 percent by weight crosslinked fibers and 50 percent by weight fluff pulp fibers based on the total weight of fibers in the bands.

The saturation capacity (Sat Cap), unrestrained vertical wicking (URVW) height, ring crush, and tensile of Controls A and B and Composites M, N, and O are summarized in Table 9.

TABLE 9

Representative Composite Characteristics

| Composite | Sat Cap (g/g) OD | URVW Height at 15 min. | Ring Crush (g) | Tensile (g/inch) |
|---|---|---|---|---|
| Control A | 19.65 | 9.75 | 350.00 | 258.50 |
| Control B | 19.25 | 10.00 | 500.00 | 310.20 |
| M | 17.36 | 14.50 | 900.00 | 1008.15 |
| N | 20.87 | 14.00 | 600.00 | 1861.20 |
| O | 19.20 | 14.50 | 675.00 | 878.90 |

As shown in Table 9, wicking for the composites having fibrous bands is increased compared to the control composites. The fibrous bands also enhance composite tensile significantly.

Figure 33:
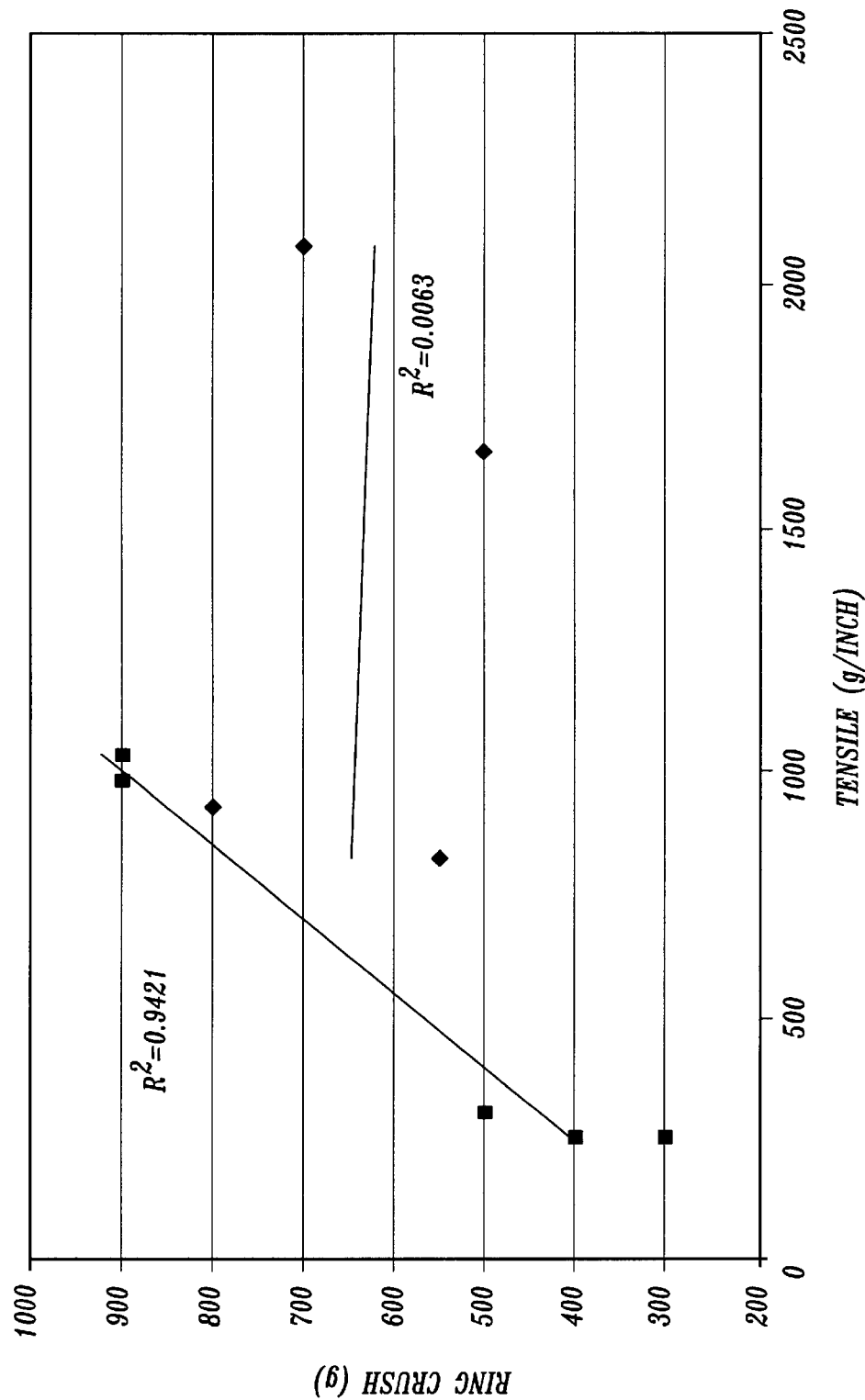
FIG. 33 is a graph correlating composite ring crush and tensile strength for representative composites formed in accordance with the present invention.

Ring crush and tensile strength for control and representative composites are correlated graphically in FIG. 33. As shown in FIG. 33, ring crush increases dramatically with increasing tensile strength for the control composite. In contrast, ring crush remains substantially constant with increasing tensile strength for the representative composite having fibrous bands. This correlation demonstrates that higher tensile strengths can be achieved in these composites without significantly increasing ring crush (i.e., decreasing softness).

Figure 34:
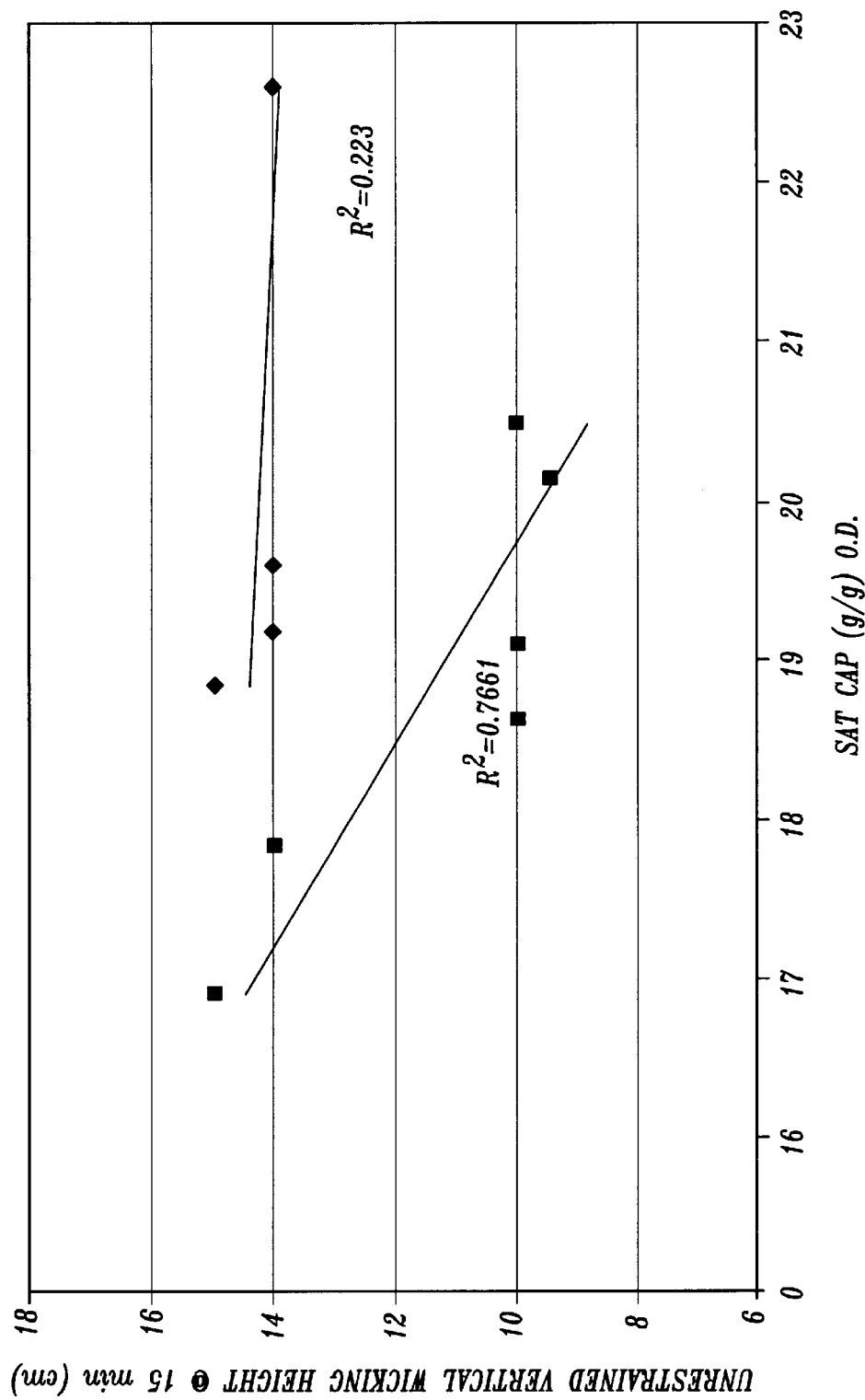
FIG. 34 is a graph correlating composite unrestrained vertical wicking height and saturation capacity for representative composites formed in accordance with the present invention.

Unrestrained vertical wicking height and saturation capacity for control and representative composites are correlated graphically in FIG. 34. As shown in FIG. 34, wicking decreases dramatically with increasing saturation capacity for the control composite. In contrast, wicking remains substantially constant with increasing saturation capacity for the representative composite having fibrous bands. This correlation demonstrates that greater wicking and fluid distribution can be achieved for these composites without decreasing saturation capacity.

Figure 35:
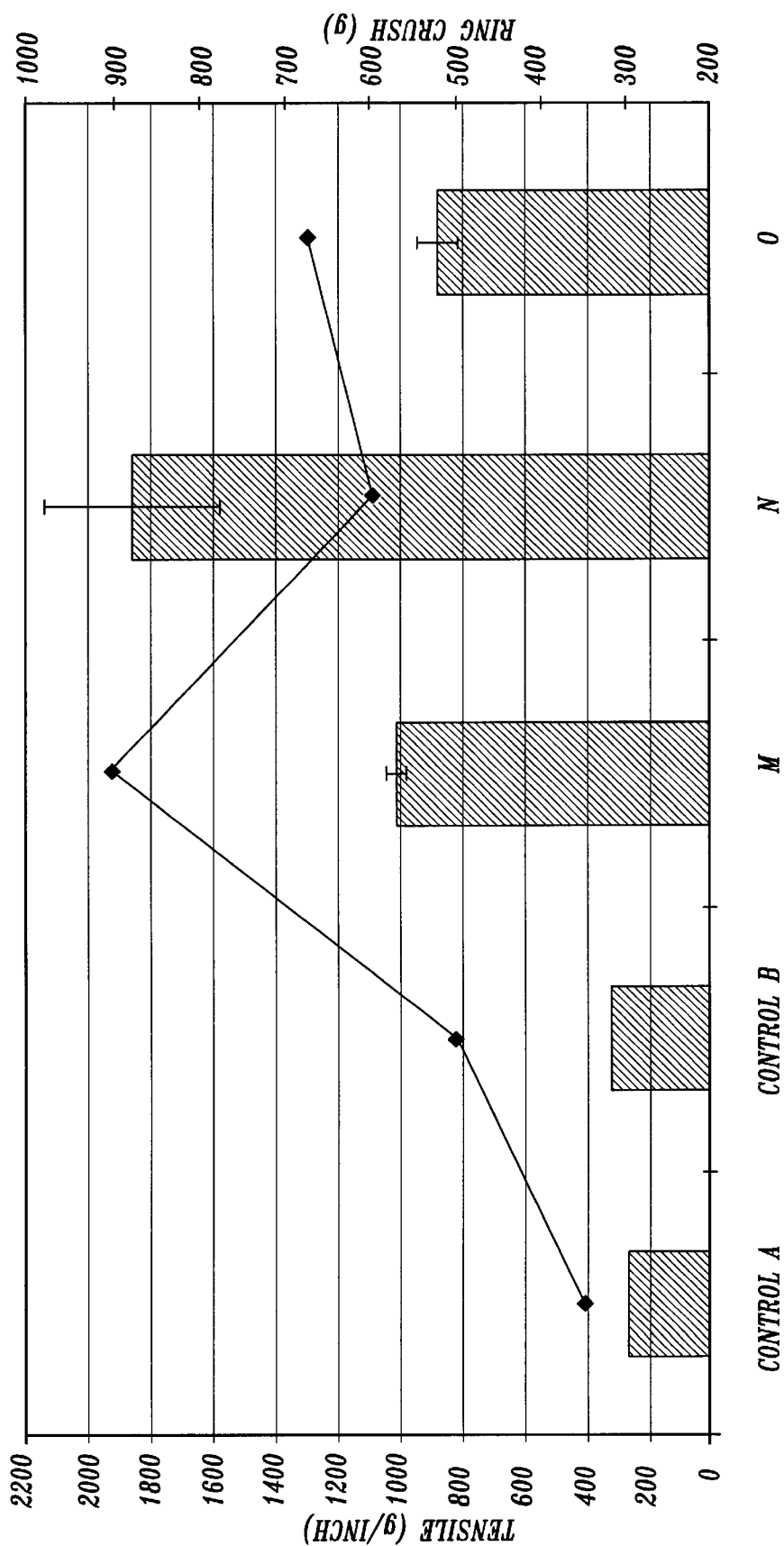
FIG. 35 is a graph comparing composite ring crush and tensile strength for representative composites formed in accordance with the present invention.

Ring crush and tensile strength for control and representative composites are compared graphically in FIG. 35. Composites M, N, and O all show increased tensile compared to the controls.

Figure 36:
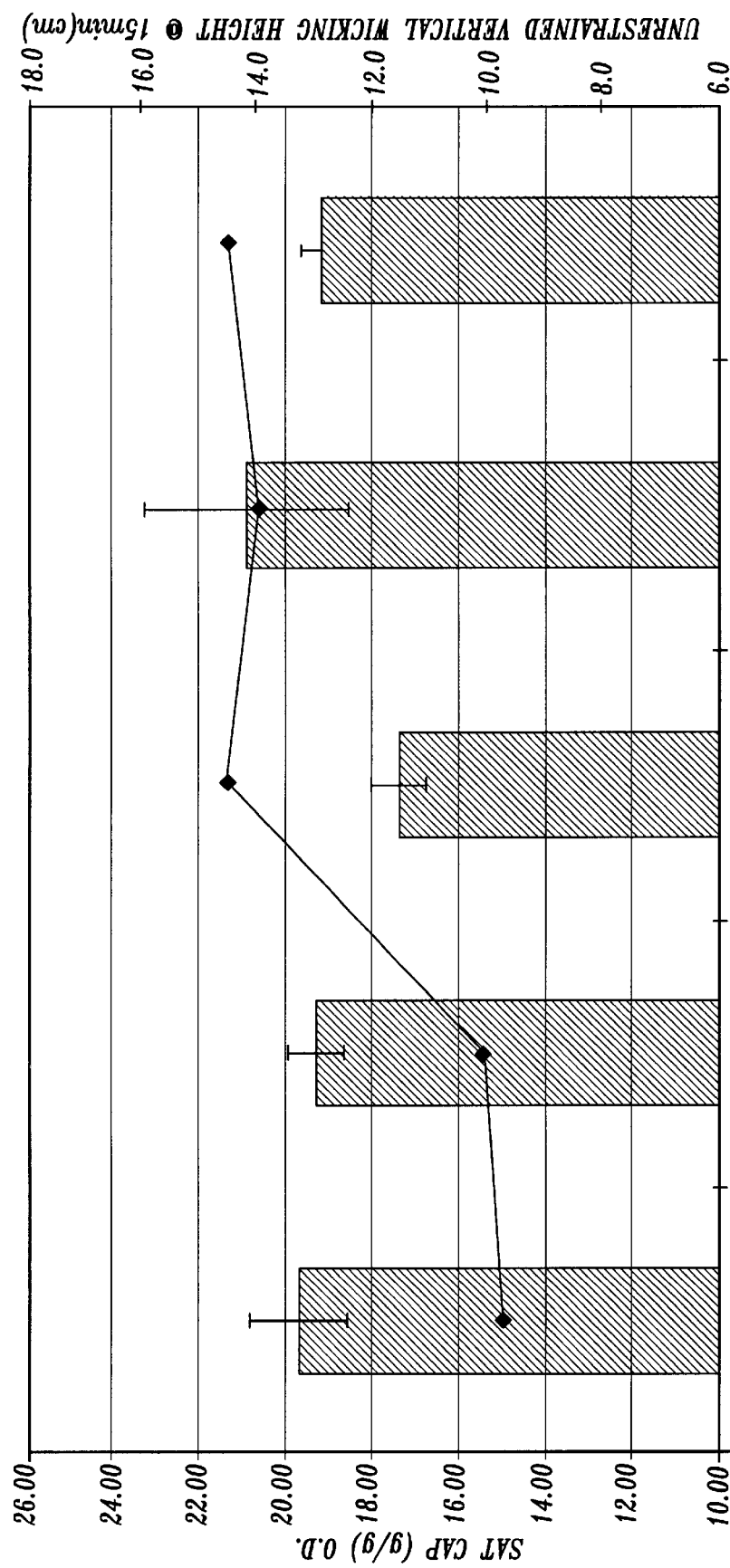
FIG. 36 is a graph comparing composite unrestrained vertical wicking height and saturation capacity for representative composites formed in accordance with the present invention.

Unrestrained vertical wicking height and saturation capacity for control and representative composites are compared graphically in FIG. 36. Composites M, N, and O all show increased wicking compared to the controls.

While the preferred embodiment of the invention has been illustrated and described, it will be appreciated that various changes can be made therein without departing from the spirit and scope of this invention.

What is claimed is:

1. An absorbent composite, comprising one or more fibrous bands in a fibrous base, wherein the base comprises a fibrous matrix and superabsorbent material, wherein the composite has a length, wherein each band is continuous along the composite's entire length, and wherein the bands are substantially free of superabsorbent material.

2. The composite of claim 1 wherein the bands are substantially parallel.

3. The composite of claim 1 wherein the fibrous matrix comprises fibers selected from the group consisting of resilient fibers, matrix fibers, and mixtures thereof.

4. The composite of claim 3 wherein the resilient fibers are selected from the group consisting of chemically stiffened fibers, anfractuous fibers, chemithermomechanical pulp fibers, prehydrolyzed kraft pulp fibers, synthetic fibers, and mixtures thereof.

5. The composite of claim 4 wherein the chemically stiffened fibers comprise crosslinked cellulosic fibers.

6. The composite of claim 5 wherein the crosslinked cellulosic fibers are crosslinked with a crosslinking agent selected from the group consisting of urea-based and polycarboxylic acid crosslinking agents.

7. The composite of claim 4 wherein the synthetic fibers are selected from the group consisting of polyolefin, polyester, polyamide, and thermobondable bicomponent fibers.

8. The composite of claim 7 wherein the polyester fibers are polyethylene terephthalate fibers.

9. The composite of claim 3 wherein the matrix fibers comprise cellulosic fibers.

10. The composite of claim 9 wherein the cellulosic fibers comprise fibers selected from the group consisting of wood pulp fibers, cotton linters, cotton fibers, hemp fibers, and mixtures thereof.

11. The composite of claim 3 wherein the resilient fibers are present in the base in an amount from about 10 to about 60 percent by weight of the total composite.

12. The composite of claim 3 wherein the matrix fibers are present in the base in an amount from about 10 to about 50 percent by weight of the total composite.

13. The composite of claim 1 wherein the superabsorbent material is selected from the group consisting of superabsorbent particles and superabsorbent fibers.

14. The composite of claim 1 wherein the superabsorbent material is present in an amount from about 0.1 to about 80 percent by weight of the total composite.

15. The composite of claim 1 wherein the superabsorbent material is present in about 40 percent by weight of the total composite.

16. The composite of claim 1 wherein the superabsorbent material absorbs from about 5 to about 100 times its weight in 0.9 percent saline solution.

17. The composite of claim 1 further comprising a wet strength agent.

18. The composite of claim 17 wherein the wet strength agent is a resin selected from the group consisting of polyamide-epichlorohydrin and polyacrylamide resins.

19. The composite of claim 17 wherein the wet strength agent is present in the composite in an amount from about 0.01 to about 2 percent by weight of the total composite.

20. The composite of claim 17 wherein the wet strength agent is present in the composite in about 0.25 percent by weight of the total composite.

21. The composite of claim 1 having a basis weight of from about 50 to about 1000 g/m$^2$.

22. The composite of claim 1 having a density of from about 0.02 to about 0.7 g/cm$^3$.

23. The composite of claim 1 wherein the one or more fibrous bands comprise fibers selected from the group consisting of resilient fibers, matrix fibers, and mixtures thereof.

24. The composite of claim 23 wherein the resilient fibers are selected from the group consisting of chemically stiffened fibers, anfractuous fibers, chemithermomechanical pulp fibers, prehydrolyzed kraft pulp fibers, synthetic fibers, and mixtures thereof.

25. The composite of claim 24 wherein the chemically stiffened fibers comprise crosslinked cellulosic fibers.

26. The composite of claim 25 wherein the crosslinked cellulosic fibers are crosslinked with a crosslinking agent selected from the group consisting of urea-based and polycarboxylic acid crosslinking agents.

27. The composite of claim 23 wherein the matrix fibers comprise cellulosic fibers.

28. The composite of claim 27 wherein the cellulosic fibers comprise fibers selected from the group consisting of wood pulp fibers, cotton linters, cotton fibers, hemp fibers, and mixtures thereof.

29. The composite of claim 27 wherein the cellulosic fibers comprise fluff pulp fibers.

30. The composite of claim 27 wherein the cellulosic fibers comprise refined pulp fibers.

31. The composite of claim 23 wherein the resilient fibers are present in the composite in an amount from about 15 to about 90 percent by weight of the total composite.

32. The composite of claim 23 wherein the matrix fibers are present in the composite in an amount from about 10 to about 85 percent by weight of the total composite.

33. An absorbent article comprising an absorbent composite comprising one or more fibrous bands in a fibrous base, wherein the base comprises a fibrous matrix and superabsorbent material, wherein the composite has a length, wherein each band is continuous along the composite's entire length, and wherein the bands are substantially free of superabsorbent material.

34. An absorbent article comprising:

liquid pervious facing sheet;

a storage layer comprising an absorbent composite comprising one or more fibrous bands in a fibrous base, wherein the base comprises a fibrous matrix and superabsorbent material, wherein the composite has a length, wherein each band is continuous along the composite's entire length, and wherein the bands are substantially free of superabsorbent material; and a liquid impervious backing sheet.

35. The absorbent article of claim 34, wherein the article is a feminine care product.

36. The absorbent article of claim 35 wherein the top sheet is joined to the backing sheet.

37. An absorbent article comprising:

a liquid pervious facing sheet;

an acquisition layer for rapidly acquiring and distributing liquid;

a storage layer comprising an absorbent composite comprising one or more fibrous bands in a fibrous base, wherein the base comprises a fibrous matrix and superabsorbent material, wherein the composite has a length, wherein each band is continuous along the composite's entire length, and wherein the bands are substantially free of superabsorbent material; and a liquid impervious backing sheet.

38. The absorbent article of claim 37 wherein the article is a diaper.

39. The absorbent article of claim 38 further comprising leg gathers.

40. An absorbent article comprising:

a liquid pervious facing sheet;

an acquisition layer for rapidly acquiring and distributing liquid;

a storage layer comprising an absorbent composite comprising one or more fibrous bands in a fibrous base, wherein the base comprises a fibrous matrix and superabsorbent material, wherein the composite has a length, wherein each band is continuous along the composite's entire length, and wherein the bands are substantially free of superabsorbent material;

an intermediate layer interposed between the acquisition layer and the storage layer; and a liquid impervious backing sheet.

41. The absorbent article of claim 40 wherein the intermediate layer is selected from the group consisting of a liquid pervious tissue and a distribution layer.

* * * * *